(12) United States Patent
Witman et al.

(10) Patent No.: US 6,531,305 B1
(45) Date of Patent: Mar. 11, 2003

(54) SPERM ASSOCIATED PROTEIN KINASE POLYPEPTIDES, CORRESPONDING NUCLEIC ACIDS, AND METHODS OF USE

(75) Inventors: George B. Witman, Grafton, MA (US); Jovenal T. San Agustin, Worcester, MA (US); John D. Leszyk, Sutton, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 09/394,455

(22) Filed: Sep. 10, 1999

Related U.S. Application Data
(60) Provisional application No. 60/099,771, filed on Sep. 10, 1998.

(51) Int. Cl.[7] .............................. C12N 9/12; C12N 1/20; C12N 15/00; C12N 5/00; C07H 21/04
(52) U.S. Cl. ................. 435/194; 435/252.3; 435/320.1; 435/325; 435/6; 536/23.7; 536/23.2
(58) Field of Search .............................. 435/194, 252.3, 435/320.1, 325; 536/23.2, 23.1, 23.7

(56) References Cited

PUBLICATIONS

Latza et al., Eur. J. Immunol., 1994, 24, 677–683.*
Horwitz et al., "Characterization and Localization . . Epididymal Sperm," *The Journal fo Biological Chemistry*, 259:832–838, (1984).
Kotani et al., "PKA and MPF—Activated Polo–like . . . Mitosis Progression," *Molecular Cell*, 1:371–380 (1980).
Lee et al., "Testicular Protein Kinased," *The Journal of Biological Chemistry* 251:914–921 (1976).
Øyen et al., "Subunits of Cyclic Adenosine 3, 5–Monophosphate–Dependent Protein Kinase Show Differential and Distinct Expression Patterns during Germ Cell Differentiation: Alternative Polyadenylation in Germ Cells Gives Rise to Unique Smaller–Sized mRNA Species," *Biology of Reproduction* 43:46–54 (1990).
Pariset et al., "Differential Expression and Subcellular Localization for Subunits of cAMP–Dependent Protein Kinase During Ram Spermatogenesis," *Journal of Cell Biology* 109:1195–1205 (1989).
San Agustin et al., "Role of cAMP in the . . . Ram Spermatozoa," *Cell Motility and the Cytoskeleton* 27:206–218 (1994).
Van Patten et al., "Specific Testicular Cellular Localization and Hormonal Regulation of the PKIα and PKIβ Isoforms of the Inhibitor Protein of the cAMP–dependent Protein Kinase," *The Journal of Biological Chemistry* 272:20021–20029 (1997).
Wooten et al., "Characterization of cAMP–Dependent Protein Kinase and Its Endogenous Substrate Proteins in Ram Testicular, Cauda Epididymal, and Ejaculated Spermatozoa," *Gamete Research* 16:57–68 (1987).

* cited by examiner

Primary Examiner—Rebecca E. Prouty
Assistant Examiner—Maryam Monshipouri
(74) *Attorney, Agent, or Firm*—Fish & Richardson P.C.

(57) ABSTRACT

The invention relates to polypeptides that are sperm-specific forms of the catalytic subunit of cAMP-dependent protein kinases, referred to herein as "$C_s$ polypeptides," nucleic acid molecules encoding $C_s$ polypeptides, and uses thereof. $C_s$ is found in sperm cells and is related to the cAMP dependent protein kinase Cα1.

12 Claims, 14 Drawing Sheets

MGNAAAAKKGSEQES/VKEFLAKAKEDFLKKWESPAQNTAHLDQFERIKTLGTGSFGRVMLVKHK
ETGNHYAMKILDKQKVVKLKQIEHTLNEKRILQAVNFPFLVKLEFSFKDNSNLYMVMEYVPGGEM
FSHLRRIGRFSEPHARFYAAQIVLTFEYLHSLDLIYRDLKPENLLIDQQGYIQVTDFGFAKRVKG
RTWTLCGTPEYLAPEIILSKGYNKAVDWWALGVLIYEMAAGYPPFFADQPIQIYEKIVSGKVRFP
SHFSSDLKDLLRNLLQVDLTKRFGNLKNGVNDIKNHKWFATTDWIAIYQRKVEAPFIPKFKGPGD
TSNFDDYEEEEIRVSINEKCGKEFSEF (SEQ ID NO:4)

FIG. 1A

```
   1  cagtgngctc  cgggccgccg  gccgcagcca  gcacccgccg  cgccgcagct  ccgggaccgg
  61  ccccggccgc  cgccgccgcg  atgggcaacg  ccgccgccgc  caagaagggc  agcgagcagg
 121  agagc/gtgaa agaattctta  gccaaagcca  aagaagattt  tcttaaaaaa  tgggaaagtc
 181  ccgctcagaa  cacagcccac  ttggatcagt  ttgaacgaat  caagaccctc  ggcacgggct
 241  ccttcgggcg  ggtgatgctg  gtgaaacaca  aggagaccgg  gaaccactat  gccatgaaga
 301  tcctcgacaa  acagaaggtg  gtgaaactga  aacagatcga  acacaccctg  aatgaaaagc
 361  gcatcctgca  agctgtcaac  tttccgttcc  tcgtcaaact  cgagttctcc  ttcaaggaca
 421  actcaaactt  atacatggtc  atggagtacg  tgcccggcgg  ggagatgttc  tcacacctac
 481  ggcggatcgg  aaggttcagt  gagcccatg   cccgtttcta  cgcggcccag  atcgtcctga
 541  cctttgagta  tctgcactcg  ctggatctca  tctacaggga  cctgaagccg  gagaatctgc
 601  tcattgacca  gcagggctac  attcaggtga  cagacttcgg  tttcgccaag  cgcgtgaagg
 661  gccgcacttg  gaccttgtgc  ggcacccctg  agtacctggc  ccctgagatt  atcctgagca
 721  aaggctacaa  caaggccgtg  gactggtggg  ccctgggggt  tcttatctat  gaaatggccg
 781  ctggctaccc  gcccttcttc  gcagaccagc  ccatccagat  ctatgagaag  atcgtctctg
 841  ggaaggtgcg  cttcccttcc  cacttcagct  ctgacttgaa  ggacctgctg  cggaacctcc
 901  tgcaggtaga  tctcaccaag  cgctttggga  acctcaagaa  tggggtcaac  gatatcaaga
 961  accacaagtg  gtttgccaca  actgactgga  ttgccatcta  ccagaggaag  gtggaagctc
1021  ccttcatacc  aaagtttaaa  ggccctgggg  atacgagtaa  ctttgacgac  tatgaggaag
1081  aagaaatccg  ggtctccatc  aatgagaagt  gtggcaagga  gttttctgag  ttttaggggc
1141  atgcctgtgc  ccccatgggt  tttcttttt   ctttttttctt ttttttggtc  gggggggtgg
1201  gagggttgga  ttgaacagcc  agagggcccc  agagttcctt  gcatctaatt  tcacccccac
1261  cccaccctcc  agggttaggg  ggagcaggaa  gcccagataa  tcagagggac  agaaacacca
1321  gctgctcccc  ctcatcccct  tcaccctcct  gccccctctc  ccacttttcc  cttcctcttt
1381  ccccacagcc  cccagcccc   tcagccctcc  cagcccactt  ctgcctgttt  taaacgagtt
1441  tctcaactcc  agtcagacca  ggtcttgctg  gtgtatccag  ggacagggta  tggaaagagg
1501  ggctcacgct  taactccagc  ccccacccac  acccccatcc  cacccaacca  caggccccac
1561  ttgctaaggg  caaatgaacg  aagcgccaac  cttccttttcg gagtaatcct  gcctgggaag
1621  gagagatttt  tagtgacatg  ttcagtgggt  tgcttgctag  aatttttttta aaaaaacaac
1681  aatttaaaat  cttatttaag  ttccaccagt  gcctccctcc  ctccttcctc  tactcccacc
1741  cctcccatgt  cccccccattc ctcaaatcca  ttttaaagag  aagcagactg  actttggaaa
1801  gggaggcgct  ggggtttgaa  cctccccgct  gctaatctcc  cctgggcccc  tccccgggga
1861  atcctctctg  ccaatcctgc  gagggtctag  gccccattag  gaagcctccg  ctctcttttt
1921  ccccaacaga  cctgtcttca  cccttgggct  ttgaaagcca  gacaaagcag  ctgcccctct
1981  ccctgccaaa  gaggagtcat  cccccaaaaa  gacagagggg  gagcccaag   cccaagtctt
2041  tcctcccagc  agcgtttccc  cccaactcct  taatttatt   ctccgctaga  ttttaacgtc
2101  cagccttccc  tcagctgagt  ggggagggca  tccctgcaaa  agggaacaga  agaggccaag
2161  tcccccaag   ccacggcccg  gggttcaagg  ctagagctgc  tggggagggg  ctgcctgttt
2221  tactcaccca  ccagcttccg  cctccccat   cctgggcgcc  cctcctccag  cttagctgtc
2281  agctgtccat  cacctctccc  ccactttctc  atttgtgctt  ttttctctcg  taatagaaaa
2341  gtggggagcc  gctggggagc  cacccccattc atcccgtat   ttcccccctct cataacttct
2401  ccccatccca  ggaggagttc  tcaggcctgg  ggtggggccc  cgggtgggtg  cggggcgat
2461  tcaacctgtg  tgctgcgaag  gacgagactt  cctcttgaac  agtgtgctgt  tgtaaacata
2521  tttgaaaact  attaccaata  aagtttgtt   (SEQ ID NO:5)
```

FIG. 1B

```
  1                            M  A  S  N  P  N  D  V  K  E  F    11
-29   TCCGGGTGCTTTGAGAGGAAGACTGATGATGGCTTCCAACCCCAACGATGTGAAAGAGT   31
                                   TACCGAAGGTTGGGGTTGCTACACTTTCTCA
      ---------+---------+---------+---------+---------+---------+-  31

12      L  A  K  A  K  E  D  F  L  K  K  W  E  N  P  A  Q  N  T  A   31
 32   TCTTAGCCAAAGCCAAAGAAGATTTTCTTAAAAAATGGGAAAATCCTGCTCAGAACACAG   91
      AGAATCGGTTTCGGTTTCTTCTAAAAGAATTTTTTACCCTTTTAGGACGAGTCTTGTGTC
 32   ---------+---------+---------+---------+---------+---------+-  91

32      H  L  D  Q  F  E  R  I  K  T  L  G  T  G  S  F  G  R  V  M   51
 92   CCCACTTGGATCAGTTTGAACGAATTAAGACCCTGGGCACGGGCTCCTTCGGGCGGGTGA  151
      GGGTGAACCTAGTCAAACTTGCTTAATTCTGGGACCCGTGCCCGAGGAAGCCCGCCCACT
 92   ---------+---------+---------+---------+---------+---------+- 151

52      L  V  K  H  T  E  T  G  N  H  Y  A  M  K  I  L  D  K  Q  K   71
152   TGCTGGTGAAGCACACGGAGACCGGGAACCACTACGCCATGAAGATCCTCGACAAACAGA  211
      ACGACCACTTCGTGTGCCTCTGGCCCTTGGTGATGCGGTACTTCTAGGAGCTGTTTGTCT
152   ---------+---------+---------+---------+---------+---------+- 211

72      V  V  K  L  K  Q  I  E  H  T  L  N  E  K  R  I  L  Q  A  V   91
212   AGGTGGTGAAGCTGAAACAGATTGAGCACACCCTGAACGAGAAGCGCATCCTGCAGGCGG  271
      TCCACCACTTCGACTTTGTCTAACTCGTGTGGGACTTGCTCTTCGCGTAGGACGTCCGCC
212   ---------+---------+---------+---------+---------+---------+- 271

92      N  F  P  F  L  V  K  L  E  F  S  F  K  D  N  S  N  L  Y  M  111
272   TCAACTTTCCGTTCCTTGTCAAACTCGAGTTCTCCTTCAAGGACAACTCAAATTTATACA  331
      AGTTGAAAGGCAAGGAACAGTTTGAGCTCAAGAGGAAGTTCCTGTTGAGTTTAAATATGT
272   ---------+---------+---------+---------+---------+---------+- 331

112      V  M  E  Y  V  P  G  G  E  M  F  S  H  L  R  R  I  G  R  F  131
332   TGGTCATGGAGTACGTGCCCGGTGGGGAGATGTTCTCACACCTGCGACGGATCGGGAGGT  391
      ACCAGTACCTCATGCACGGGCCACCCCTCTACAAGAGTGTGGACGCTGCCTAGCCCTCCA
332   ---------+---------+---------+---------+---------+---------+- 391

132      S  E  P  H  A  R  F  Y  A  A  Q  I  V  L  T  F  E  Y  L  H  151
392   TCAGTGAGCCCCACGCGCGCTTCTACGCCGCCCAGATTGTCCTGACCTTTGAGTACCTGC  451
      AGTCACTCGGGGTGCGCGCGAAGATGCGGCGGGTCTAACAGGACTGGAAACTCATGGACG
392   ---------+---------+---------+---------+---------+---------+- 451

152      S  L  D  L  I  Y  R  D  L  K  P  E  N  L  L  I  D  Q  Q  G  171
452   ACTCGCTTGATCTCATCTACCGGGACCTGAAGCCGGAGAACCTCCTCATTGACCAGCAGG  511
      TGAGCGAACTAGAGTAGATGGCCCTGGACTTCGGCCTCTTGGAGGAGTAACTGGTCGTCC
452   ---------+---------+---------+---------+---------+---------+- 511
```

FIG. 2A

```
172      Y  I  Q  V  T  D  F  G  F  A  K  R  V  K  G  R  T  W  T  L    191
512  GCTACATTCAGGTGACAGACTTCGGTTTCGCCAAGCGTGTGAAAGGCCGCACCTGGACCT      571
     CGATGTAAGTCCACTGTCTGAAGCCAAAGCGGTTCGCACACTTTCCGGCGTGGACCTGGA
512  ---------+---------+---------+---------+---------+---------+-    571

192      C  G  T  P  E  Y  L  A  P  E  I  I  L  S  K  G  Y  N  K  A    211
572  TGTGTGGGACCCCCGAGTACCTGGCCCCCGAGATCATCCTGAGTAAAGGCTACAACAAAG      631
     ACACACCCTGGGGGCTCATGGACCGGGGGCTCTAGTAGGACTCATTTCCGATGTTGTTTC
572  ---------+---------+---------+---------+---------+---------+-    631

212      V  D  W  A  L  G  V  L  I  Y  E  M  A  A  G  Y  P  P  F       231
632  CTGTGGACTGGTGGGCCCTGGGGGTCCTCATCTATGAAATGGCCGCAGGCTACCCGCCCT      691
     GACACCTGACCACCCGGGACCCCCAGGAGTAGATACTTTACCGGCGTCCGATGGGCGGGA
632  ---------+---------+---------+---------+---------+---------+-    691

232   F  A  D  Q  P  I  Q  I  Y  E  K  I  V  S  G  K  V  R  F  P       251
692  TCTTCGCCGACCAGCCCATCCAGATCTACGAGAAGATTGTCTCTGGGAAGGTGCGGTTTC      751
     AGAAGCGGCTGGTCGGGTAGGTCTAGATGCTCTTCTAACAGAGACCCTTCCACGCCAAAG
692  ---------+---------+---------+---------+---------+---------+-    751

252    S  H  F  S  S  D  L  K  D  L  L  R  N  L  L  Q  V  D  L  T      271
752  CATCCCACTTCAGCTCTGACTTGAAGGATCTGCTGCGCAACCTCCTACAAGTGGACCTCA      811
     GTAGGGTGAAGTCGAGACTGAACTTCCTAGACGACGCGTTGGAGGATGTTCACCTGGAGT
752  ---------+---------+---------+---------+---------+---------+-    811

272       K  R  F  G  N  L  K  N  G  V  N  D  I  K  N  H  K  W  F  A   291
812  CCAAGCGCTTTGGGAACCTCAAGAATGGGGTCAATGATATAAAGAACCACAAGTGGTTTG      871
     GGTTCGCGAAACCCTTGGAGTTCTTACCCCAGTTACTATATTTCTTGGTGTTCACCAAAC
812  ---------+---------+---------+---------+---------+---------+-    871

292   T  T  D  W  I  A  I  Y  Q  R  K  V  E  A  P  F  I  P  K  F       311
872  CCACAACTGACTGGATTGCCATCTACCAGAGAAAGGTGGAAGCTCCCTTCATACCAAAGT      931
     GGTGTTGACTGACCTAACGGTAGATGGTCTCTTTCCACCTTCGAGGGAAGTATGGTTTCA
872  ---------+---------+---------+---------+---------+---------+-    931

312    K  G  P  G  D  T  S  N  F  D  D  Y  E  E  E  E  I  R  V  S      331
932  TTAAAGGCCCTGGGGACACAAGTAACTTTGACGACTATGAGGAGGAAGAGATCCGAGTCT      991
     AATTTCCGGGACCCCTGTGTTCATTGAAACTGCTGATACTCCTCCTTCTCTAGGCTCAGA
932  ---------+---------+---------+---------+---------+---------+-    991

332     I  N  E  K  C  G  K  E  F  S  E  F    (SEQ ID NO: 15)          343
992  CCATCAATGAGAAGTGTGGCAAGGAGTTTTCTGAGTTCTAGGGGTGTGACTGTGCCCCCA      1051
     GGTAGTTACTCTTCACACCGTTCCTCAAAAGACTCAAG
     ---------+---------+---------+---------+---------+---------+-

1052 TGGGTTTTCTTTCTTTCCTTTTTTTTTTTGGTGGGGGGGGTGGGAGGGTTGGATTGAACA      1111
     ---------+---------+---------+---------+---------+---------+-
```

FIG. 2B

```
1112  GCCAGAGGGCCCCAGAGTTCCTTGCATCTAATTTAACCCGCCCAGCCCCACCCTCCAGGG  1171
      --------+---------+---------+---------+---------+---------+-

1172  TAGGGGGAGCAGGAAGTCCAGGTATTTGGGGCAAAACACCAGCTGCTCCCCCTCACCCCC  1231
      --------+---------+---------+---------+---------+---------+-

1232  TTTGCCCTCCTGCCCACCCCTACCCACTGCTTTTGCCTTCCTTCCACAGCCCCCCACCCC  1291
      --------+---------+---------+---------+---------+---------+-

1292  AGCCGACTTCTGCCTGTTTTAAACGAATTTCTCGGTTCTTCCCTTCTTCAGGGCAGACCA  1351
      --------+---------+---------+---------+---------+---------+-

1352  GGTCTCCCTGGTTTCAGGGACAGGGTGTGGCAAGAGGGGCCCAAACTTAACTACAGCCAC  1411
      --------+---------+---------+---------+---------+---------+-

1412  CCCTCCCCCCCCCAAAAAAAAAAACCCGACAGGCACCACTCTCTAACGGTGAATGAATGAA  1471
      --------+---------+---------+---------+---------+---------+-

1472  AAGCCAACCTTGCCTTCAGAATAATCCTGCCAGGGAAGGAGAGATTTTAGTGACTCGTTC  1531
      --------+---------+---------+---------+---------+---------+-

1532  AGTGGGCCACTTGCTGTAATTTTTTAAAAAAATACAATTTACAATCTTATTTAAGTTCC   1590
      --------+---------+---------+---------+---------+---------+
```

(SEQ ID NO: 14)  FIG. 2C

PARTIAL SEQUENCE OF HUMAN C$_S$ cDNA (clone 8)

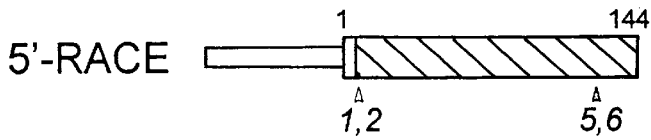

-163 CCCAGTGGCCTCTGGGTTGGGTTTCTCTTCCTGCTCCCACCCCACGGCTCCCTAGCTCCC
     CCTGCAGGCAGGGTTCTGGGGACAGACAGCCGAACAGACACGGCAGGTCTCATGAGCCTT

```
                                                          1
                                                   M  A  S  N  S  S    6
-43  CCCAGCCACCGTAGTGCCGGTGCCCTGAGAACAGGACTGAGTGATGGCTTCCAACTCCAG

D  V  K  E  F  L  A  K  A  K  E  D  F  L  K  K  W  E  S  P   26
 19  CGATGTGAAAGAATTCTTAGCCAAAGCCAAAGAAGATTTTCTTAAAAAATGGGAAAGTCC
          1,2

A  Q  N  T  A  H  L  D  Q  F  E  R  I  K  T  L  G  T  G  S   46
 79  CGCTCAGAACACAGCCCACTTGGATCAGTTTGAACGAATCAAGACCCTCGGCACGGGCTC

F  G  R  V  M  L  V  K  H  K  E  T  G  N  H  Y  A  M  K  I   66
139  CTTCGGGCGGGTGATGCTGGTGAAACACAAGGAGACCGGGAACCACTATGCCATGAAGAT

L  D  K  Q  K  V  V  K  L  K  Q  I  E  H  T  L  N  E  K  R   86
199  CCTCGACAAACAGAAGGTGGTGAAACTGAAACAGATCGAACACACCCTGAATGAAAAGCG

I  L  Q  A  V  N  F  P  F  L  V  K  L  E  F  S  F  K  D  N  106
259  CATCCTGCAAGCTGTCAACTTTCCGTTCCTCGTCAAACTCGAGTTCTCCTTCAAGGACAA

S  N  L  Y  M  V  M  E  Y  V  P  G  G  E  M  F  S  H  L  R  126
319  CTCAAACTTATACATGGTCATGGAGTACGTGCCCGGCGGGGAGATGTTCTCACACCTACG

144
      R  I  G  R  F  S  E  P  H  A  R  F  Y  A  A  Q  I  V   (SEQ ID NO: 43)
379  GCGGATCGGAAGGTTCAGTGAGCCCCATGCCCGTTTCTACGCGGCCCAGATCGT  (SEQ ID NO: 42)
                      5,6
```

FIG. 3

Predicted Full-Length C$_s$ Human Coding Sequence

```
CCCAGTGGCCTCTGGGTTGGGTTTCTCTTCCTGCTCCCACCCCACGGCTCCCTAGCTCCCCTGC
AGGCAGGGTTCTGGGGACAGACAGCCGAACAGACACGGCAGGTCTCATGAGCCTTCCCAGCCACC
GTAGTGCCGGTGCCCTGAGAACAGGACTGAGTGATGGCTTCCAACTCCAGCGATgtgaaagaatt
cttagccaaagccaaagaagatttcttaaaaaatgggaaagtcccgctcagaacacagcccact
tggatcagtttgaacgaatcaagaccctcggcacgggctccttcgggcgggtgatgctggtgaaa
cacaaggagaccgggaaccactatgccatgaagatcctcgacaaacagaaggtggtgaaactgaa
acagatcgaacacaccctgaatgaaaagcgcatcctgcaagctgtcaactttccgttcctcgtca
aactcgagttctccttcaaggacaactcaaacttatacatggtcatggagtacgtgcccggcggg
gagatgttctcacacctacggcggatcggaaggttcagtgagcccatgcccgtttctacgcggc
ccagatcgtcctgacctttgagtatctgcactcgctggatctcatctacagggacctgaagccgg
agaatctgctcattgaccagcagggctacattcaggtgacagacttcggtttcgccaagcgcgtg
aagggccgcacttggaccttgtgcggcacccctgagtacctggcccctgagattatcctgagcaa
aggctacaacaaggccgtggactggtgggccctggggttcttatctatgaaatggccgctggct
acccgcccttcttcgcagaccagcccatccagatctatgagaagatcgtctctgggaaggtgcgc
ttcccttcccacttcagctctgacttgaaggacctgctgcggaacctcctgcaggtagatctcac
caagcgctttgggaacctcaagaatggggtcaacgatatcaagaaccacaagtggtttgccacaa
ctgactggattgccatctaccagaggaaggtggaagctcccttcataccaaagtttaaaggccct
ggggatacgagtaactttgacgactatgaggaagaagaaatccgggtctccatcaatgagaagtg
tggcaaggagttttctgagttttagggcatgcctgtgcccccatgggttttcttttttctttt
tctttttttttggtcgggggggtgggagggttggattgaacagccagagggccccagagttccttg
catctaatttcaccccacccccacccctccagggttaggggggagcaggaagcccagataatcagag
ggacagaaacaccagctgctcccctcatccccttcaccctcctgcccctctcccactttccc
ttcctctttccccacagccccccagcccctcagccctcccagcccacttctgcctgttttaaacg
agtttctcaactccagtcagaccaggtcttgctggtgtatccagggacagggtatggaaagaggg
gctcacgcttaactccagccccccacccacacccccatcccacccaaccacaggccccacttgcta
agggcaaatgaacgaagcgccaaccttcctttcggagtaatcctgcctgggaaggagagattttt
agtgacatgttcagtgggttgcttgctagaatttttttaaaaaaacaacaatttaaaatcttatt
taagttccaccagtgcctccctccctccttcctctactcccacccctcccatgtcccccattcc
tcaaatccatttttaaagagaagcagactgactttggaaagggaggcgctgggtttgaacctccc
cgctgctaatctcccctgggcccctccccggggaatcctctctgccaatcctgcgagggtctagg
cccctttaggaagcctccgctctcttttccccaacagacctgtcttcaccttgggctttgaaa
gccagacaaagcagctgcccctctccctgccaaagaggagtcatccccaaaaagacagagggg
agccccaagcccaagtctttcctcccagcagcgtttccccccaactccttaatttttattctccgc
tagattttaacgtccagccttccctcagctgagtggggagggcatccctgcaaaagggaacagaa
gaggccaagtcccccaagccacggcccgggttcaaggctagagctgctggggaggggctgcct
gttttactcacccaccagcttccgcctccccatcctgggcgcccctcctccagcttagctgtca
gctgtccatcacctctcccccactttctcatttgtgcttttctctcgtaatagaaaagtgggg
agccgctggggagccaccccattcatcccgtatttccccctctcataacttctccccatcccag
gaggagttctcaggcctggggtggggccccgggtgggtgcggggcgattcaacctgtgtgctgc
gaaggacgagacttcctcttgaacagtgtgctgttgtaaacatatttgaaaactattaccaataa
agtttgtt  (SEQ ID NO:35)
```

FIG. 4A

Predicted Full-Length Human $C_s$ Amino Acid Sequence

MASNSSDVKEFLAKAKEDFLKKWESPAQNTAHLDQFERIKTLGTGSFGRVMLVKHKETGNHYAMK
ILDKQKVVKLKQIEHTLNEKRILQAVNFPFLVKLEFSFKDNSNLYMVMEYVPGGEMFSHLRRIGR
FSEPHARFYAAQIVLTFEYLHSLDLIYRDLKPENLLIDQQGYIQVTDFGFAKRVKGRTWTLCGTP
EYLAPEIILSKGYNKAVDWWALGVLIYEMAAGYPPFFADQPIQIYEKIVSGKVRFPSHFSSDLKD
LLRNLLQVDLTKRFGNLKNGVNDIKNHKWFATTDWIAIYQRKVEAPFIPKFKGPGDTSNFDDYEE
EEIRVSINEKCGKEFSEF (SEQ ID NO:34)

FIG. 4B

PARTIAL SEQUENCE OF MURINE C$_S$ cDNA (clone 7)

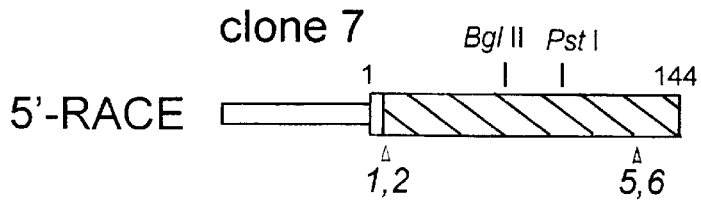

```
-190  GGGTTCTATCTGCCCCTACCCTGCACCCATTAGTCTGCAGGTTGAGTTTCTCTTCCTGTT
      CCCACCCTATCACTCCCTGGCTCCCTCTACAGGCAGGGCTCCCCCCCAGGACTGGCAGCC
      AAACTGCTGCAGCAGATCTTATGAGGCTTCCGAGCCACCGTAATGCTAGTGCCCTGAGAA

1
         M   A   S   S   S   N   D   V   K   E   F   L   A   K   A   K   E    17
-10   AGACTGAGTGATGGCTTCCAGCTCCAACGATGTGAAAGAGTTCCTAGCCAAAGCCAAGGA
                                        ▲
                                       1,2
         D   F   L   K   K   W   E   T   P   S   Q   N   T   A   Q   L   D   Q   F   D    37
 51   AGATTTCCTGAAAAAATGGGAGACCCCTTCTCAGAATACAGCCCAGTTGGATCAGTTTGA

R   I   K   T   L   G   T   G   S   F   G   R   V   M   L   V   K   H   K   E    57
111   TAGAATCAAGACCCTTGGCACCGGCTCCTTTGGGCGAGTGATGCTGGTGAAGCACAAGGA

S   G   N   H   Y   A   M   K   I   L   D   K   Q   K   V   V   K   L   K   Q    77
171   GAGTGGGAACCACTACGCCATGAAGATCTTAGACAAGCAGAAGGTGGTGAAGCTAAAGCA

I   E   H   T   L   N   E   K   R   I   L   Q   A   V   N   F   P   F   L   V    97
231   GATCGAGCACACTCTGAATGAGAAGCGCATCCTGCAGGCCGTCAACTTCCCGTTCCTGGT

K   L   E   F   S   F   K   D   N   S   N   L   Y   M   V   M   E   Y   V   A   117
291   CAAACTTGAATTCTCCTTCAAGGACAACTCAAACCTGTACATGGTCATGGAGTATGTAGC

G   G   E   M   F   S   H   L   R   R   I   G   R   F   S   E   P   H   A   R   137
351   TGGTGGCGAGATGTTCTCCCACCTACGGCGGATTGGAAGGTTCAGCGAGCCCCATGCCCG
                                                               ▲
                                                              5,6
                    144
         F   Y   A   A   Q   I   V    (SEQ ID NO: 45)
411   TTTCTACGCGGCGCAGATCGT    (SEQ ID NO: 44)
```

FIG. 5

```
-190  GGGTTCTATCTGCCCCTACCCTGCACCCATTAGTCTGCAGGTTGAGTTTCTCTTCCTGTT  -129
      ----------+---------+---------+---------+---------+---------+

-130  CCCACCCTATCACTCCCTGGCTCCCTCTACAGGCAGGGCTCCCCCCCAGGACTGGCAGCC  -69
      ----------+---------+---------+---------+---------+---------+

-70   AAACTGCTGCAGCAGATCTTATGAGGCTTCCGAGCCACCGTAATGCTAGTGCCCTGAGAA  -11
      ----------+---------+---------+---------+---------+---------+

1             M  A  S  S  S  N  D  V  K  E  F  L  A  K  A  K  E    17
 -10  AGACTGAGTGATGGCTTCCAGCTCCAACGATGTGAAAGAGTTCCTAGCCAAAGCCAAGGA   50
      TCTGACTCACTACCGAAGGTCGAGGTTGCTACACTTTCTCAAGGATCGGTTTCGGTTCCT
  51  ----------+---------+---------+---------+---------+---------+  110

18  D  F  L  K  K  W  E  D  P  S  Q  N  T  A  Q  L  D  Q  F  D      37
  51  AGATTTCCTGAAAAAATGGGAAGACCCCTCTCAGAATACAGCCCAGTTGGATCAGTTTGA  110
      TCTAAAGGACTTTTTTACCCTTCTGGGGAGAGTCTTATGTCGGGTCAACCTAGTCAAACT
  51  ----------+---------+---------+---------+---------+---------+  110

38  R  I  K  T  L  G  T  G  S  F  G  R  V  M  L  V  K  H  K  E      57
 111  TAGAATCAAGACCCTTGGCACCGGCTCCTTTGGGCGAGTGATGCTGGTGAAGCACAAGGA  170
      ATCTTAGTTCTGGGAACCGTGGCCGAGGAAACCCGCTCACTACGACCACTTCGTGTTCCT
 111  ----------+---------+---------+---------+---------+---------+  170

58  S  G  N  H  Y  A  M  K  I  L  D  K  Q  K  V  V  K  L  K  Q      77
 171  GAGTGGGAACCACTACGCCATGAAGATCTTAGACAAGCAGAAGGTGGTGAAGCTAAAGCA  230
      CTCACCCTTGGTGATGCGGTACTTCTAGAATCTGTTCGTCTTCCACCACTTCGATTTCGT
 171  ----------+---------+---------+---------+---------+---------+  230

78  I  E  H  T  L  N  E  K  R  I  L  Q  A  V  N  F  P  F  L  V      97
 231  GATCGAGCACACTCTGAATGAGAAGCGCATCCTGCAGGCCGTCAACTTCCCGTTCCTGGT  290
      CTAGCTCGTGTGAGACTTACTCTTCGCGTAGGACGTCCGGCAGTTGAAGGGCAAGGACCA
 231  ----------+---------+---------+---------+---------+---------+  290

98  K  L  E  F  S  F  K  D  N  S  N  L  Y  M  V  M  E  Y  V  A     117
 291  CAAACTTGAATTCTCCTTCAAGGACAACTCAAACCTGTACATGGTCATGGAGTATGTAGC  350
      GTTTGAACTTAAGAGGAAGTTCCTGTTGAGTTTGGACATGTACCAGTACCTCATACATCG
 291  ----------+---------+---------+---------+---------+---------+  350

118  G  G  E  M  F  S  H  L  R  R  I  G  R  F  S  E  P  H  A  R     137
 351  TGGTGGCGAGATGTTCTCCCACCTACGGCGGATTGGAAGGTTCAGCGAGCCCCATGCCCG  410
      ACCACCGCTCTACAAGAGGGTGGATGCCGCCTAACCTTCCAAGTCGCTCGGGGTACGGGC
 351  ----------+---------+---------+---------+---------+---------+  410
```

FIG. 6A

```
138  F   Y   A   A   Q   I   V   L   T   F   E   Y   L   H   S   L   D   L   I   Y    157
411  TTTCTACGCGGCGCAGATCGTCCTGACCTTTGAGTATCTGCACTCCCTGGACCTCATCTA                      470
     AAAGATGCGCCGCGTCTAGCAGGACTGGAAACTCATAGACGTGAGGGACCTGGAGTAGAT
411  ---------+---------+---------+---------+---------+---------+                      470

158  R   D   L   K   P   E   N   L   L   I   D   Q   Q   G   Y   I   Q   V   T   D    177
471  CCGGGACCTGAAGCCCGAGAATCTTCTCATCGACCAGCAGGGCTATATTCAGGTGACAGA                      530
     GGCCCTGGACTTCGGGCTCTTAGAAGAGTAGCTGGTCGTCCCGATATAAGTCCACTGTCT
471  ---------+---------+---------+---------+---------+---------+                      530

178  F   G   F   A   K   R   V   K   G   R   T   W   T   L   C   G   T   P   E   Y    197
531  CTTCGGTTTTGCCAAGCGTGTGAAAGGCCGTACTTGGACCTTGTGTGGGACCCCTGAGTA                      590
     GAAGCCAAAACGGTTCGCACACTTTCCGGCATGAACCTGGAACACACCCTGGGGACTCAT
531  ---------+---------+---------+---------+---------+---------+                      590

198  L   A   P   E   I   I   L   S   K   G   Y   N   K   A   V   D   W   W   A   L    217
591  CTTGGCCCCCGAGATTATCCTGAGCAAAGGCTACAACAAGGCTGTGGACTGGTGGGCTCT                      650
     GAACCGGGGGCTCTAATAGGACTCGTTTCCGATGTTGTTCCGACACCTGACCACCCGAGA
591  ---------+---------+---------+---------+---------+---------+                      650

218  G   V   L   I   Y   E   M   A   A   G   Y   P   P   F   F   A   D   Q   P   I    237
651  CGGAGTCCTCATCTACGAGATGGCTGCTGGTTACCCACCCTTCTTCGCTGACCAGCCTAT                      710
     GCCTCAGGAGTAGATGCTCTACCGACGACCAATGGGTGGGAAGAAGCGACTGGTCGGATA
651  ---------+---------+---------+---------+---------+---------+                      710

238  Q   I   Y   E   K   I   V   S   G   K   V   R   F   P   S   H   F   S   S   D    257
711  CCAGATCTATGAGAAAATCGTCTCTGGGAAGGTGCGGTTCCCATCCCACTTCAGCTCTGA                      770
     GGTCTAGATACTCTTTTAGCAGAGACCCTTCCACGCCAAGGGTAGGGTGAAGTCGAGACT
711  ---------+---------+---------+---------+---------+---------+                      770

258  L   K   D   L   L   R   N   L   L   Q   V   D   L   T   K   R   F   G   N   L    277
771  CTTGAAGGACCTGCTGCGGAACCTTCTGCAAGTGGATCTAACCAAGCGCTTTGGAAACCT                      830
     GAACTTCCTGGACGACGCCTTGGAAGACGTTCACCTAGATTGGTTCGCGAAACCTTTGGA
771  ---------+---------+---------+---------+---------+---------+                      830

278  K   D   G   V   N   D   I   K   N   H   K   W   F   A   T   T   D   W   I   A    297
831  CAAGGACGGGGTCAATGACATCAAGAACCACAAGTGGTTTGCCACGACTGACTGGATTGC                      890
     GTTCCTGCCCCAGTTACTGTAGTTCTTGGTGTTCACCAAACGGTGCTGACTGACCTAACG
831  ---------+---------+---------+---------+---------+---------+                      890

298  I   Y   Q   R   K   V   E   A   P   F   I   P   K   F   K   G   P   G   D   T    317
891  CATCTATCAGAGAAAGGTGGAAGCTCCCTTCATACCAAAGTTTAAAGGCCCTGGGGACAC                      950
     GTAGATAGTCTCTTTCCACCTTCGAGGGAAGTATGGTTTCAAATTTCCGGGACCCCTGTG
891  ---------+---------+---------+---------+---------+---------+                      950
```

FIG. 6B

```
318  S  N  F  D  D  Y  E  E  E  E  I  R  V  S  I  N  E  K  C  G   337
951  GAGTAACTTTGACGACTATGAGGAGGAAGAGATCCGGGTCTCCATCAATGAGAAGTGTGG  1010
     CTCATTGAAACTGCTGATACTCCTCCTTCTCTAGGCCCAGAGGTAGTTACTCTTCACACC
951  ----------+---------+---------+---------+---------+---------+  1010

338  K  E  F  T  E  F    (SEQ ID NO: 38)                            343
1011 CAAGGAGTTTACTGAGTTTTAGGGGTGTGCTTGTGCCCCTTGGGTTCTCTTTCATTTTTT  1070
     GTTCCTCAAATGACTCAAA
1011 ----------+---------+---------+---------+---------+---------+

1071 CTTTTTCTTTCTATTTTTTTTCCGGTTGGGGGTGGGAGGGTTGGATCGGAACAGCCAGAG  1130
     ----------+---------+---------+---------+---------+---------+

1131 GGCCCTAGAGTTCCATGCATCTAATTTAACATCCACTCCACACCCCCAGGGTTAAGGAGA  1190
     ----------+---------+---------+---------+---------+---------+

1191 GCAGGAAAGCGCTTCCAGATTACTGGGGAAGGGCAACATCAGCTGCTCCCCCTATCCCTT  1250
     ----------+---------+---------+---------+---------+---------+

1251 GTTGTCCACCCTTCCCTTCCTGTTTTAATGAATTTCTTAGCTCCAGCCATACCCAATCTT  1310
     ----------+---------+---------+---------+---------+---------+

1311 GCTGGTGTATCCAGGGGCAGGGTACGGAAAGAGGGCCCCAAATTCAGCCTCCTTCCCGAC  1370
     ----------+---------+---------+---------+---------+---------+

1371 CCTAGCACTGGATACTAAGGATGAACGAACAGTAACGCCAACCTTCCCTTCCATGCAGCC  1430
     ----------+---------+---------+---------+---------+---------+

1431 CTACCTGGAAAGGGAGATTTTATGACCTGTACAGAGGGCTGCTTGCCAGTGGGTTTTTTT  1490
     ----------+---------+---------+---------+---------+---------+

1491 TTTCATTTAAATTAAGTTCCACCAGTGCCTCCCACCCTCCAAATTGTCCCACCCTCCCCA  1550
     ----------+---------+---------+---------+---------+---------+

1551 AACACCCTCCTCACTCCCTAAATCAATTCTGATGAGACCTGGGTAGCCAACTGACCCTGT  1610
     ----------+---------+---------+---------+---------+---------+

1611 CAAGGAAGGAACTGGGCTTGGAATCTCGCCCTGAGCTGCTAGCTCCCGGCCCCCCTTTCC  1670
     ----------+---------+---------+---------+---------+---------+

1671 AGTGGTCTCATGCCAATTTGTCCTGTGCATCAGCCCCCTTAAGAAGCCTCCCCATCCTGG  1730
     ----------+---------+---------+---------+---------+---------+
```

FIG. 6C

1731  CGCCTCGCTTCTAGCTTAGCTGTCAGCTGTCCATCACCTCTTGCCGTGCGTCCCACTCA  1790

1791  CTGCAACCCCAAGTCTCTGATTGTGCTTTTTCTCTCAATAGAAAGGTGGGAGCTGCTGGGG  1850

1851  AAATTACCCCCATTTATCCCTGTGTTTATCCCTCGTCGTAACTTCTCCCAAAAGGAGGAG  1910

1911  CTCTCAGGCCTGGGGTGGGGGCCCCGGGTGGACGAGAGGGGTCGTCAACCTGTGTGCTTCAA  1970

1971  AGGATGAGACTTCCTCTCTTGAACAGTGTGCTGTGTGTAAACATATATTTGAAAAC  2021

(SEQ ID NO: 39)

FIG. 6D

COMPARISON OF MURINE, OVINE, AND HUMAN C$_S$ EXON 1s

NUCLEOTIDE SEQUENCE

```
                                                      [-                                                 -]
mC_s  -29  TAATGCTAGTGCCCTGAGAAGACTGAGTG ATG GCT TCC AGC TCC AAC GAT G   (SEQ ID NO: 55)
oC_s  -29  TCCGGGTGCTTTGAGAGAAGACTGAGTG ATG GCT TCC AAC CCC AAC GAT G     (SEQ ID NO: 20)
hC_s  -29  TGCCGGTGCCCTGAGAACAGGACTGAGTG ATG GCT TCC AAC TCC AGC GAT G    (SEQ ID NO: 56)
                                         [—————— oC_s (-11) ——————]
```

FIG. 7A

AMINO ACID SEQUENCE

```
         1                          7
mC_s     M  A  S  S  N  D           (SEQ ID NO: 40)
oC_s     M  A  S  N  P  N  D        (SEQ ID NO: 8)
hC_s     M  A  S  N  S  S  D        (SEQ ID NO: 36)
```

FIG. 7B

```
                            SEQUENCE LISTING

<160> NUMBER OF SEQ ID NOS:  56

<210> SEQ ID NO 1
<211> LENGTH: 6
<212> TYPE: PRT
<213> ORGANISM: Artificial Sequence
<220> FEATURE:
<221> NAME/KEY: VARIANT
<222> LOCATION: (1)...(6)
<223> OTHER INFORMATION: Xaa = Any Amino Acid
<223> OTHER INFORMATION: Synthetically generated protein

<400> SEQUENCE: 1

Xaa Ser Xaa Xaa Xaa Asp
  1               5

<210> SEQ ID NO 2
<211> LENGTH: 336
<212> TYPE: PRT
<213> ORGANISM: Homo sapiens

<400> SEQUENCE: 2

Val Lys Glu Phe Leu Ala Lys Ala Lys Glu Asp Phe Leu Lys Lys Trp
  1               5                  10                  15

Glu Ser Pro Ala Gln Asn Thr Ala His Leu Asp Gln Phe Glu Arg Ile
                 20                  25                  30

Lys Thr Leu Gly Thr Gly Ser Phe Gly Arg Val Met Leu Val Lys His
             35                  40                  45

Lys Glu Thr Gly Asn His Tyr Ala Met Lys Ile Leu Asp Lys Gln Lys
         50                  55                  60

Val Val Lys Leu Lys Gln Ile Glu His Thr Leu Asn Glu Lys Arg Ile
 65                  70                  75                  80

Leu Gln Ala Val Asn Phe Pro Phe Leu Val Lys Leu Glu Phe Ser Phe
                 85                  90                  95

Lys Asp Asn Ser Asn Leu Tyr Met Val Met Glu Tyr Val Pro Gly Gly
                100                 105                 110

Glu Met Phe Ser His Leu Arg Arg Ile Gly Arg Phe Ser Glu Pro His
            115                 120                 125

Ala Arg Phe Tyr Ala Ala Gln Ile Val Leu Thr Phe Glu Tyr Leu His
        130                 135                 140

Ser Leu Asp Leu Ile Tyr Arg Asp Leu Lys Pro Glu Asn Leu Leu Ile
145                 150                 155                 160

Asp Gln Gln Gly Tyr Ile Gln Val Thr Asp Phe Gly Phe Ala Lys Arg
                165                 170                 175

Val Lys Gly Arg Thr Trp Thr Leu Cys Gly Thr Pro Glu Tyr Leu Ala
            180                 185                 190

Pro Glu Ile Ile Leu Ser Lys Gly Tyr Asn Lys Ala Val Asp Trp Trp
        195                 200                 205

Ala Leu Gly Val Leu Ile Tyr Glu Met Ala Ala Gly Tyr Pro Pro Phe
    210                 215                 220

Phe Ala Asp Gln Pro Ile Gln Ile Tyr Glu Lys Ile Val Ser Gly Lys
225                 230                 235                 240
```

-continued

```
Val Arg Phe Pro Ser His Phe Ser Ser Asp Leu Lys Asp Leu Leu Arg
            245                 250                 255

Asn Leu Leu Gln Val Asp Leu Thr Lys Arg Phe Gly Asn Leu Lys Asn
            260                 265                 270

Gly Val Asn Asp Ile Lys Asn His Lys Trp Phe Ala Thr Thr Asp Trp
            275                 280                 285

Ile Ala Ile Tyr Gln Arg Lys Val Glu Ala Pro Phe Ile Pro Lys Phe
    290                 295                 300

Lys Gly Pro Gly Asp Thr Ser Asn Phe Asp Asp Tyr Glu Glu Glu Glu
305                 310                 315                 320

Ile Arg Val Ser Ile Asn Glu Lys Cys Gly Lys Glu Phe Ser Glu Phe
                325                 330                 335
```

<210> SEQ ID NO 3
<211> LENGTH: 1008
<212> TYPE: DNA
<213> ORGANISM: Homo sapiens
<220> FEATURE:
<221> NAME/KEY: CDS
<222> LOCATION: (1)...(1008)

<400> SEQUENCE: 3

```
gtg aaa gaa ttc tta gcc aaa gcc aaa gaa gat ttt ctt aaa aaa tgg      48
Val Lys Glu Phe Leu Ala Lys Ala Lys Glu Asp Phe Leu Lys Lys Trp
  1               5                  10                  15 gaa agt ccc gct cag aac aca gcc cac ttg gat cag ttt gaa cga atc      96
Glu Ser Pro Ala Gln Asn Thr Ala His Leu Asp Gln Phe Glu Arg Ile
                 20                  25                  30 aag acc ctc ggc acg ggc tcc ttc ggg cgg gtg atg ctg gtg aaa cac     144
Lys Thr Leu Gly Thr Gly Ser Phe Gly Arg Val Met Leu Val Lys His
             35                  40                  45 aag gag acc ggg aac cac tat gcc atg aag atc ctc gac aaa cag aag     192
Lys Glu Thr Gly Asn His Tyr Ala Met Lys Ile Leu Asp Lys Gln Lys
         50                  55                  60 gtg gtg aaa ctg aaa cag atc gaa cac acc ctg aat gaa aag cgc atc     240
Val Val Lys Leu Lys Gln Ile Glu His Thr Leu Asn Glu Lys Arg Ile
 65                  70                  75                  80 ctg caa gct gtc aac ttt ccg ttc ctc gtc aaa ctc gag ttc tcc ttc     288
Leu Gln Ala Val Asn Phe Pro Phe Leu Val Lys Leu Glu Phe Ser Phe
                 85                  90                  95 aag gac aac tca aac tta tac atg gtc atg gag tac gtg ccc ggc ggg     336
Lys Asp Asn Ser Asn Leu Tyr Met Val Met Glu Tyr Val Pro Gly Gly
                100                 105                 110 gag atg ttc tca cac cta cgg cgg atc gga agg ttc agt gag ccc cat     384
Glu Met Phe Ser His Leu Arg Arg Ile Gly Arg Phe Ser Glu Pro His
            115                 120                 125 gcc cgt ttc tac gcg gcc cag atc gtc ctg acc ttt gag tat ctg cac     432
Ala Arg Phe Tyr Ala Ala Gln Ile Val Leu Thr Phe Glu Tyr Leu His
        130                 135                 140 tcg ctg gat ctc atc tac agg gac ctg aag ccg gag aat ctg ctc att     480
Ser Leu Asp Leu Ile Tyr Arg Asp Leu Lys Pro Glu Asn Leu Leu Ile
145                 150                 155                 160 gac cag cag ggc tac att cag gtg aca gac ttc ggt ttc gcc aag cgc     528
Asp Gln Gln Gly Tyr Ile Gln Val Thr Asp Phe Gly Phe Ala Lys Arg
                165                 170                 175 gtg aag ggc cgc act tgg acc ttg tgc ggc acc cct gag tac ctg gcc     576
Val Lys Gly Arg Thr Trp Thr Leu Cys Gly Thr Pro Glu Tyr Leu Ala
            180                 185                 190
```

-continued

| | | |
|---|---|---|
| cct gag att atc ctg agc aaa ggc tac aac aag gcc gtg gac tgg tgg<br>Pro Glu Ile Ile Leu Ser Lys Gly Tyr Asn Lys Ala Val Asp Trp Trp<br>195                              200                           205 | | 624 |
| gcc ctg ggg gtt ctt atc tat gaa atg gcc gct ggc tac ccg ccc ttc<br>Ala Leu Gly Val Leu Ile Tyr Glu Met Ala Ala Gly Tyr Pro Pro Phe<br>210                              215                           220 | | 672 |
| ttc gca gac cag ccc atc cag atc tat gag aag atc gtc tct ggg aag<br>Phe Ala Asp Gln Pro Ile Gln Ile Tyr Glu Lys Ile Val Ser Gly Lys<br>225                              230                           235                    240 | | 720 |
| gtg cgc ttc cct tcc cac ttc agc tct gac ttg aag gac ctg ctg cgg<br>Val Arg Phe Pro Ser His Phe Ser Ser Asp Leu Lys Asp Leu Leu Arg<br>                        245                           250                           255 | | 768 |
| aac ctc ctg cag gta gat ctc acc aag cgc ttt ggg aac ctc aag aat<br>Asn Leu Leu Gln Val Asp Leu Thr Lys Arg Phe Gly Asn Leu Lys Asn<br>            260                           265                           270 | | 816 |
| ggg gtc aac gat atc aag aac cac aag tgg ttt gcc aca act gac tgg<br>Gly Val Asn Asp Ile Lys Asn His Lys Trp Phe Ala Thr Thr Asp Trp<br>            275                           280                           285 | | 864 |
| att gcc atc tac cag agg aag gtg gaa gct ccc ttc ata cca aag ttt<br>Ile Ala Ile Tyr Gln Arg Lys Val Glu Ala Pro Phe Ile Pro Lys Phe<br>290                              295                           300 | | 912 |
| aaa ggc cct ggg gat acg agt aac ttt gac gac tat gag gaa gaa gaa<br>Lys Gly Pro Gly Asp Thr Ser Asn Phe Asp Asp Tyr Glu Glu Glu Glu<br>305                              310                           315                    320 | | 960 |
| atc cgg gtc tcc atc aat gag aag tgt ggc aag gag ttt tct gag ttt<br>Ile Arg Val Ser Ile Asn Glu Lys Cys Gly Lys Glu Phe Ser Glu Phe<br>                        325                           330                           335 | | 1008 |

<210> SEQ ID NO 4
<211> LENGTH: 351
<212> TYPE: PRT
<213> ORGANISM: Homo sapiens

<400> SEQUENCE: 4

Met Gly Asn Ala Ala Ala Ala Lys Lys Gly Ser Glu Gln Glu Ser Val
1               5                   10                  15

Lys Glu Phe Leu Ala Lys Ala Lys Glu Asp Phe Leu Lys Lys Trp Glu
            20                  25                  30

Ser Pro Ala Gln Asn Thr Ala His Leu Asp Gln Phe Glu Arg Ile Lys
        35                  40                  45

Thr Leu Gly Thr Gly Ser Phe Gly Arg Val Met Leu Val Lys His Lys
    50                  55                  60

Glu Thr Gly Asn His Tyr Ala Met Lys Ile Leu Asp Lys Gln Lys Val
65                  70                  75                  80

Val Lys Leu Lys Gln Ile Glu His Thr Leu Asn Glu Lys Arg Ile Leu
                85                  90                  95

Gln Ala Val Asn Phe Pro Phe Leu Val Lys Leu Glu Phe Ser Phe Lys
            100                 105                 110

Asp Asn Ser Asn Leu Tyr Met Val Met Glu Tyr Val Pro Gly Gly Glu
        115                 120                 125

Met Phe Ser His Leu Arg Arg Ile Gly Arg Phe Ser Glu Pro His Ala
    130                 135                 140

Arg Phe Tyr Ala Ala Gln Ile Val Leu Thr Phe Glu Tyr Leu His Ser
145                 150                 155                 160

Leu Asp Leu Ile Tyr Arg Asp Leu Lys Pro Glu Asn Leu Leu Ile Asp
                165                 170                 175

Gln Gln Gly Tyr Ile Gln Val Thr Asp Phe Gly Phe Ala Lys Arg Val
            180                 185                 190

-continued

```
Lys Gly Arg Thr Trp Thr Leu Cys Gly Thr Pro Glu Tyr Leu Ala Pro
            195                 200                 205

Glu Ile Ile Leu Ser Lys Gly Tyr Asn Lys Ala Val Asp Trp Trp Ala
    210                 215                 220

Leu Gly Val Leu Ile Tyr Glu Met Ala Ala Gly Tyr Pro Pro Phe Phe
225                 230                 235                 240

Ala Asp Gln Pro Ile Gln Ile Tyr Glu Lys Ile Val Ser Gly Lys Val
                245                 250                 255

Arg Phe Pro Ser His Phe Ser Ser Asp Leu Lys Asp Leu Leu Arg Asn
                260                 265                 270

Leu Leu Gln Val Asp Leu Thr Lys Arg Phe Gly Asn Leu Lys Asn Gly
            275                 280                 285

Val Asn Asp Ile Lys Asn His Lys Trp Phe Ala Thr Thr Asp Trp Ile
    290                 295                 300

Ala Ile Tyr Gln Arg Lys Val Glu Ala Pro Phe Ile Pro Lys Phe Lys
305                 310                 315                 320

Gly Pro Gly Asp Thr Ser Asn Phe Asp Asp Tyr Glu Glu Glu Ile
                325                 330                 335

Arg Val Ser Ile Asn Glu Lys Cys Gly Lys Glu Phe Ser Glu Phe
            340                 345                 350

<210> SEQ ID NO 5
<211> LENGTH: 2549
<212> TYPE: DNA
<213> ORGANISM: Homo sapiens
<220> FEATURE:
<221> NAME/KEY: CDS
<222> LOCATION: (81)...(1133)
<221> NAME/KEY: misc_feature
<222> LOCATION: (1)...(2549)
<223> OTHER INFORMATION: n = A,T,C or G

<400> SEQUENCE: 5
cagtgngctc cgggccgccg ccgcagcca gcacccgccg cgccgcagct ccgggaccgg      60
ccccggccgc cgccgccgcg atg ggc aac gcc gcc gcc gcc aag aag ggc agc    113
                      Met Gly Asn Ala Ala Ala Ala Lys Lys Gly Ser
                       1               5                  10 gag cag gag agc gtg aaa gaa ttc tta gcc aaa gcc aaa gaa gat ttt      161
Glu Gln Glu Ser Val Lys Glu Phe Leu Ala Lys Ala Lys Glu Asp Phe
            15                  20                  25 ctt aaa aaa tgg gaa agt ccc gct cag aac aca gcc cac ttg gat cag      209
Leu Lys Lys Trp Glu Ser Pro Ala Gln Asn Thr Ala His Leu Asp Gln
        30                  35                  40 ttt gaa cga atc aag acc ctc ggc acg ggc tcc ttc ggg cgg gtg atg      257
Phe Glu Arg Ile Lys Thr Leu Gly Thr Gly Ser Phe Gly Arg Val Met
    45                  50                  55 ctg gtg aaa cac aag gag acc ggg aac cac tat gcc atg aag atc ctc      305
Leu Val Lys His Lys Glu Thr Gly Asn His Tyr Ala Met Lys Ile Leu
60                  65                  70                  75 gac aaa cag aag gtg gtg aaa ctg aaa cag atc gaa cac acc ctg aat      353
Asp Lys Gln Lys Val Val Lys Leu Lys Gln Ile Glu His Thr Leu Asn
                80                  85                  90 gaa aag cgc atc ctg caa gct gtc aac ttt ccg ttc ctc gtc aaa ctc      401
Glu Lys Arg Ile Leu Gln Ala Val Asn Phe Pro Phe Leu Val Lys Leu
            95                 100                 105 gag ttc tcc ttc aag gac aac tca aac tta tac atg gtc atg gag tac      449
Glu Phe Ser Phe Lys Asp Asn Ser Asn Leu Tyr Met Val Met Glu Tyr
        110                 115                 120
```

-continued

| | |
|---|---|
| gtg ccc ggc ggg gag atg ttc tca cac cta cgg cgg atc gga agg ttc<br>Val Pro Gly Gly Glu Met Phe Ser His Leu Arg Arg Ile Gly Arg Phe<br>125                             130                     135 | 497 |
| agt gag ccc cat gcc cgt ttc tac gcg gcc cag atc gtc ctg acc ttt<br>Ser Glu Pro His Ala Arg Phe Tyr Ala Ala Gln Ile Val Leu Thr Phe<br>140                         145                        150                 155 | 545 |
| gag tat ctg cac tcg ctg gat ctc atc tac agg gac ctg aag ccg gag<br>Glu Tyr Leu His Ser Leu Asp Leu Ile Tyr Arg Asp Leu Lys Pro Glu<br>                     160                        165                     170 | 593 |
| aat ctg ctc att gac cag cag ggc tac att cag gtg aca gac ttc ggt<br>Asn Leu Leu Ile Asp Gln Gln Gly Tyr Ile Gln Val Thr Asp Phe Gly<br>175                         180                        185 | 641 |
| ttc gcc aag cgc gtg aag ggc cgc act tgg acc ttg tgc ggc acc cct<br>Phe Ala Lys Arg Val Lys Gly Arg Thr Trp Thr Leu Cys Gly Thr Pro<br>       190                     195                       200 | 689 |
| gag tac ctg gcc cct gag att atc ctg agc aaa ggc tac aac aag gcc<br>Glu Tyr Leu Ala Pro Glu Ile Ile Leu Ser Lys Gly Tyr Asn Lys Ala<br>205                         210                        215 | 737 |
| gtg gac tgg tgg gcc ctg ggg gtt ctt atc tat gaa atg gcc gct ggc<br>Val Asp Trp Trp Ala Leu Gly Val Leu Ile Tyr Glu Met Ala Ala Gly<br>220                         225                        230                 235 | 785 |
| tac ccg ccc ttc ttc gca gac cag ccc atc cag atc tat gag aag atc<br>Tyr Pro Pro Phe Phe Ala Asp Gln Pro Ile Gln Ile Tyr Glu Lys Ile<br>                     240                        245                     250 | 833 |
| gtc tct ggg aag gtg cgc ttc cct tcc cac ttc agc tct gac ttg aag<br>Val Ser Gly Lys Val Arg Phe Pro Ser His Phe Ser Ser Asp Leu Lys<br>255                         260                        265 | 881 |
| gac ctg ctg cgg aac ctc ctg cag gta gat ctc acc aag cgc ttt ggg<br>Asp Leu Leu Arg Asn Leu Leu Gln Val Asp Leu Thr Lys Arg Phe Gly<br>       270                     275                       280 | 929 |
| aac ctc aag aat ggg gtc aac gat atc aag aac cac aag tgg ttt gcc<br>Asn Leu Lys Asn Gly Val Asn Asp Ile Lys Asn His Lys Trp Phe Ala<br>285                         290                        295 | 977 |
| aca act gac tgg att gcc atc tac cag agg aag gtg gaa gct ccc ttc<br>Thr Thr Asp Trp Ile Ala Ile Tyr Gln Arg Lys Val Glu Ala Pro Phe<br>300                         305                        310                 315 | 1025 |
| ata cca aag ttt aaa ggc cct ggg gat acg agt aac ttt gac gac tat<br>Ile Pro Lys Phe Lys Gly Pro Gly Asp Thr Ser Asn Phe Asp Asp Tyr<br>                     320                        325                     330 | 1073 |
| gag gaa gaa gaa atc cgg gtc tcc atc aat gag aag tgt ggc aag gag<br>Glu Glu Glu Glu Ile Arg Val Ser Ile Asn Glu Lys Cys Gly Lys Glu<br>335                         340                        345 | 1121 |
| ttt tct gag ttt tagggcatg cctgtgcccc catgggtttt cttttttctt<br>Phe Ser Glu Phe<br>       350 | 1173 |
| tttctttttt tttggtcggg ggggtgggag ggttggattg aacagccaga gggccccaga | 1233 |
| gttccttgca tctaatttca cccccacccc accctccagg gttaggggga gcaggaagcc | 1293 |
| cagataatca gagggacaga aacaccagct gctcccccte atccccttca ccctcctgcc | 1353 |
| ccctctccca ctttteccett cctctttccc cacagccccc cagcccctca gcctcccag | 1413 |
| cccacttctg cctgttttaa acgagtttct caactccagt cagaccaggt cttgctggtg | 1473 |
| tatccaggga cagggtatgg aaagagggc tcacgcttaa ctccagcccc cacccacacc | 1533 |
| cccatcccac ccaaccacag gccccacttg ctaagggcaa atgaacgaag cgccaacctt | 1593 |
| cctttcggag taatcctgcc tgggaaggag agatttttag tgacatgttc agtgggttgc | 1653 |
| ttgctagaat ttttttaaaa aaacaacaat ttaaatctt atttaagttc caccagtgcc | 1713 |
| tccctccctc cttcctctac tcccacccct cccatgtccc cccattcctc aaatccattt | 1773 |

-continued

```
taaagagaag cagactgact ttggaaaggg aggcgctggg gtttgaacct ccccgctgct    1833
aatctcccct gggcccctcc ccggggaatc ctctctgcca atcctgcgag ggtctaggcc    1893
cctttaggaa gcctccgctc tcttttccc  caacagacct gtcttcaccc ttgggctttg    1953
aaagccagac aaagcagctg cccctctccc tgccaaagag gagtcatccc ccaaaaagac    2013 agaggggag  cccaagccc  aagtctttcc tcccagcagc gtttccccc  aactccttaa    2073 ttttattctc cgctagattt taacgtccag ccttccctca gctgagtggg gagggcatcc    2133
ctgcaaaagg gaacagaaga ggccaagtcc cccaagcca  cggcccgggg ttcaaggcta    2193
gagctgctgg ggagggctg  cctgttttac tcacccacca gcttccgcct ccccatcct    2253 gggcgcccct cctccagctt agctgtcagc tgtccatcac ctctccccca ctttctcatt    2313 tgtgctttt  tctctcgtaa tagaaaagtg gggagccgct ggggagccac cccattcatc    2373
cccgtatttc cccctctcat aacttctccc catcccagga ggagttctca ggcctggggt    2433
ggggccccgg gtgggtgcgg gggcgattca acctgtgtgc tgcgaaggac gagacttcct    2493
cttgaacagt gtgctgttgt aaacatattt gaaaactatt accaataaag tttgtt        2549
```

```
<210> SEQ ID NO 6
<211> LENGTH: 6
<212> TYPE: PRT
<213> ORGANISM: Ovine

<400> SEQUENCE: 6

Ala Ser Asn Pro Asn Asp
  1               5

<210> SEQ ID NO 7
<211> LENGTH: 6
<212> TYPE: PRT
<213> ORGANISM: Ovine

<400> SEQUENCE: 7

Pro Ser Ser Ser Asn Asp
  1               5

<210> SEQ ID NO 8
<211> LENGTH: 7
<212> TYPE: PRT
<213> ORGANISM: Ovine

<400> SEQUENCE: 8

Met Ala Ser Asn Pro Asn Asp
  1               5

<210> SEQ ID NO 9
<211> LENGTH: 7
<212> TYPE: PRT
<213> ORGANISM: Ovine

<400> SEQUENCE: 9

Met Pro Ser Ser Ser Asn Asp
  1               5

<210> SEQ ID NO 10
<211> LENGTH: 18
<212> TYPE: DNA
<213> ORGANISM: Ovine

<400> SEQUENCE: 10
gcttccaacc ccaacgat                                                  18
```

```
<210> SEQ ID NO 11
<211> LENGTH: 18
<212> TYPE: DNA
<213> ORGANISM: Ovine

<400> SEQUENCE: 11
ccttccagct ccaatgat                                                      18

<210> SEQ ID NO 12
<211> LENGTH: 21
<212> TYPE: DNA
<213> ORGANISM: Ovine

<400> SEQUENCE: 12
atggcttcca accccaacga t                                                  21

<210> SEQ ID NO 13
<211> LENGTH: 21
<212> TYPE: DNA
<213> ORGANISM: Ovine

<400> SEQUENCE: 13
atgccttcca gctccaatga t                                                  21

<210> SEQ ID NO 14
<211> LENGTH: 1619
<212> TYPE: DNA
<213> ORGANISM: Ovine
<220> FEATURE:
<221> NAME/KEY: CDS
<222> LOCATION: (30)...(1058)

<400> SEQUENCE: 14
tccgggtgct tgagaggaa gactgagtg atg gct tcc aac ccc aac gat gtg           53
                               Met Ala Ser Asn Pro Asn Asp Val
                                 1               5 aaa gag ttc tta gcc aaa gcc aaa gaa gat ttt ctt aaa aaa tgg gaa         101
Lys Glu Phe Leu Ala Lys Ala Lys Glu Asp Phe Leu Lys Lys Trp Glu
 10              15                  20 aat cct gct cag aac aca gcc cac ttg gat cag ttt gaa cga att aag         149
Asn Pro Ala Gln Asn Thr Ala His Leu Asp Gln Phe Glu Arg Ile Lys
 25                  30                  35                  40 acc ctg ggc acg ggc tcc ttc ggg cgg gtg atg ctg gtg aag cac acg         197
Thr Leu Gly Thr Gly Ser Phe Gly Arg Val Met Leu Val Lys His Thr
                 45                  50                  55 gag acc ggg aac cac tac gcc atg aag atc ctc gac aaa cag aag gtg         245
Glu Thr Gly Asn His Tyr Ala Met Lys Ile Leu Asp Lys Gln Lys Val
             60                  65                  70 gtg aag ctg aaa cag att gag cac acc ctg aac gag aag cgc atc ctg         293
Val Lys Leu Lys Gln Ile Glu His Thr Leu Asn Glu Lys Arg Ile Leu
         75                  80                  85 cag gcg gtc aac ttt ccg ttc ctt gtc aaa ctc gag ttc tcc ttc aag         341
Gln Ala Val Asn Phe Pro Phe Leu Val Lys Leu Glu Phe Ser Phe Lys
     90                  95                 100 gac aac tca aat tta tac atg gtc atg gag tac gtg ccc ggt ggg gag         389
Asp Asn Ser Asn Leu Tyr Met Val Met Glu Tyr Val Pro Gly Gly Glu
105                 110                 115                 120 atg ttc tca cac ctg cga cgg atc ggg agg ttc agt gag ccc cac gcg         437
Met Phe Ser His Leu Arg Arg Ile Gly Arg Phe Ser Glu Pro His Ala
                125                 130                 135 cgc ttc tac gcc gcc cag att gtc ctg acc ttt gag tac ctg cac tcg         485
Arg Phe Tyr Ala Ala Gln Ile Val Leu Thr Phe Glu Tyr Leu His Ser
            140                 145                 150
```

```
ctt gat ctc atc tac cgg gac ctg aag ccg gag aac ctc ctc att gac     533
Leu Asp Leu Ile Tyr Arg Asp Leu Lys Pro Glu Asn Leu Leu Ile Asp
        155                 160                 165 cag cag ggc tac att cag gtg aca gac ttc ggt ttc gcc aag cgt gtg     581
Gln Gln Gly Tyr Ile Gln Val Thr Asp Phe Gly Phe Ala Lys Arg Val
170                 175                 180 aaa ggc cgc acc tgg acc ttg tgt ggg acc ccc gag tac ctg gcc ccc     629
Lys Gly Arg Thr Trp Thr Leu Cys Gly Thr Pro Glu Tyr Leu Ala Pro
185                 190                 195                 200 gag atc atc ctg agt aaa ggc tac aac aaa gct gtg gac tgg tgg gcc     677
Glu Ile Ile Leu Ser Lys Gly Tyr Asn Lys Ala Val Asp Trp Trp Ala
        205                 210                 215 ctg ggg gtc ctc atc tat gaa atg gcc gca ggc tac ccg ccc ttc ttc     725
Leu Gly Val Leu Ile Tyr Glu Met Ala Ala Gly Tyr Pro Pro Phe Phe
        220                 225                 230 gcc gac cag ccc atc cag atc tac gag aag att gtc tct ggg aag gtg     773
Ala Asp Gln Pro Ile Gln Ile Tyr Glu Lys Ile Val Ser Gly Lys Val
        235                 240                 245 cgg ttt cca tcc cac ttc agc tct gac ttg aag gat ctg ctg cgc aac     821
Arg Phe Pro Ser His Phe Ser Ser Asp Leu Lys Asp Leu Leu Arg Asn
        250                 255                 260 ctc cta caa gtg gac ctc acc aag cgc ttt ggg aac ctc aag aat ggg     869
Leu Leu Gln Val Asp Leu Thr Lys Arg Phe Gly Asn Leu Lys Asn Gly
265                 270                 275                 280 gtc aat gat ata aag aac cac aag tgg ttt gcc aca act gac tgg att     917
Val Asn Asp Ile Lys Asn His Lys Trp Phe Ala Thr Thr Asp Trp Ile
        285                 290                 295 gcc atc tac cag aga aag gtg gaa gct ccc ttc ata cca aag ttt aaa     965
Ala Ile Tyr Gln Arg Lys Val Glu Ala Pro Phe Ile Pro Lys Phe Lys
        300                 305                 310 ggc cct ggg gac aca agt aac ttt gac gac tat gag gag gaa gag atc    1013
Gly Pro Gly Asp Thr Ser Asn Phe Asp Asp Tyr Glu Glu Glu Glu Ile
        315                 320                 325 cga gtc tcc atc aat gag aag tgt ggc aag gag ttt tct gag ttc        1058
Arg Val Ser Ile Asn Glu Lys Cys Gly Lys Glu Phe Ser Glu Phe
        330                 335                 340 tagggtgtg actgtgcccc catgggtttt ctttctttcc ttttttttt tggtgggggg    1118 ggtgggaggg ttggattgaa cagccagagg gccccagagt tccttgcatc taatttaacc   1178
cgcccagccc caccctccag ggtaggggga gcaggaagtc caggtatttg gggcaaaaca   1238
ccagctgctc cccctcaccc cctttgccct cctgccacc cctacccact gcttttgcct    1298
tccttccaca gccccccacc ccagccgact tctgcctgtt ttaaacgaat ttctcggttc   1358
ttcccttctt cagggcagac caggtctccc tggtttcagg acagggtgt ggcaagaggg    1418 gcccaaactt aactacagcc acccctcccc cccaaaaa aaaaacccga caggcaccac    1478
tctctaacgg tgaatgaatg aaaagccaac cttgccttca gaataatcct gccagggaag   1538
gagagatttt agtgactcgt tcagtgggcc acttgctgta attttttaaa aaatacaat    1598 ttacaatctt atttaagttc c                                            1619

<210> SEQ ID NO 15
<211> LENGTH: 343
<212> TYPE: PRT
<213> ORGANISM: Ovine

<400> SEQUENCE: 15

Met Ala Ser Asn Pro Asn Asp Val Lys Glu Phe Leu Ala Lys Ala Lys
1               5                   10                  15
```

-continued

```
Glu Asp Phe Leu Lys Lys Trp Glu Asn Pro Ala Gln Asn Thr Ala His
            20                  25                  30

Leu Asp Gln Phe Glu Arg Ile Lys Thr Leu Gly Thr Gly Ser Phe Gly
        35                  40                  45

Arg Val Met Leu Val Lys His Thr Glu Thr Gly Asn His Tyr Ala Met
    50                  55                  60

Lys Ile Leu Asp Lys Gln Lys Val Val Lys Leu Lys Gln Ile Glu His
65                  70                  75                  80

Thr Leu Asn Glu Lys Arg Ile Leu Gln Ala Val Asn Phe Pro Phe Leu
                85                  90                  95

Val Lys Leu Glu Phe Ser Phe Lys Asp Asn Ser Asn Leu Tyr Met Val
            100                 105                 110

Met Glu Tyr Val Pro Gly Gly Glu Met Phe Ser His Leu Arg Arg Ile
        115                 120                 125

Gly Arg Phe Ser Glu Pro His Ala Arg Phe Tyr Ala Ala Gln Ile Val
    130                 135                 140

Leu Thr Phe Glu Tyr Leu His Ser Leu Asp Leu Ile Tyr Arg Asp Leu
145                 150                 155                 160

Lys Pro Glu Asn Leu Leu Ile Asp Gln Gln Gly Tyr Ile Gln Val Thr
                165                 170                 175

Asp Phe Gly Phe Ala Lys Arg Val Lys Gly Arg Thr Trp Thr Leu Cys
            180                 185                 190

Gly Thr Pro Glu Tyr Leu Ala Pro Glu Ile Ile Leu Ser Lys Gly Tyr
        195                 200                 205

Asn Lys Ala Val Asp Trp Trp Ala Leu Gly Val Leu Ile Tyr Glu Met
    210                 215                 220

Ala Ala Gly Tyr Pro Pro Phe Phe Ala Asp Gln Pro Ile Gln Ile Tyr
225                 230                 235                 240

Glu Lys Ile Val Ser Gly Lys Val Arg Phe Pro Ser His Phe Ser Ser
                245                 250                 255

Asp Leu Lys Asp Leu Leu Arg Asn Leu Leu Gln Val Asp Leu Thr Lys
            260                 265                 270

Arg Phe Gly Asn Leu Lys Asn Gly Val Asn Asp Ile Lys Asn His Lys
        275                 280                 285

Trp Phe Ala Thr Thr Asp Trp Ile Ala Ile Tyr Gln Arg Lys Val Glu
    290                 295                 300

Ala Pro Phe Ile Pro Lys Phe Lys Gly Pro Gly Asp Thr Ser Asn Phe
305                 310                 315                 320

Asp Asp Tyr Glu Glu Glu Glu Ile Arg Val Ser Ile Asn Glu Lys Cys
                325                 330                 335

Gly Lys Glu Phe Ser Glu Phe
            340
```

<210> SEQ ID NO 16
<211> LENGTH: 18
<212> TYPE: DNA
<213> ORGANISM: Ovine

<400> SEQUENCE: 16
cgaaggttgg ggttgcta                                                18

<210> SEQ ID NO 17
<211> LENGTH: 18
<212> TYPE: DNA
<213> ORGANISM: Ovine

```
<400> SEQUENCE: 17
ggaaggtcga ggttacta                                                   18

<210> SEQ ID NO 18
<211> LENGTH: 21
<212> TYPE: DNA
<213> ORGANISM: Ovine

<400> SEQUENCE: 18
taccgaaggt tggggttgct a                                               21

<210> SEQ ID NO 19
<211> LENGTH: 21
<212> TYPE: DNA
<213> ORGANISM: Ovine

<400> SEQUENCE: 19
tacggaaggt cgaggttact a                                               21

<210> SEQ ID NO 20
<211> LENGTH: 51
<212> TYPE: DNA
<213> ORGANISM: Ovine

<400> SEQUENCE: 20
tccgggtgct ttgagaggaa gactgagtga tggcttccaa ccccaacgat g              51

<210> SEQ ID NO 21
<211> LENGTH: 25
<212> TYPE: DNA
<213> ORGANISM: Ovine

<400> SEQUENCE: 21
tccgggtgct ttgagaggaa gactg                                           25

<210> SEQ ID NO 22
<211> LENGTH: 42
<212> TYPE: DNA
<213> ORGANISM: Ovine

<400> SEQUENCE: 22
tttgagagga agactgagtg atggcttcca accccaacga tg                        42

<210> SEQ ID NO 23
<211> LENGTH: 20
<212> TYPE: DNA
<213> ORGANISM: Ovine

<400> SEQUENCE: 23
gagtgatggc ttccaacccc                                                 20

<210> SEQ ID NO 24
<211> LENGTH: 7
<212> TYPE: PRT
<213> ORGANISM: Artificial Sequence
<220> FEATURE:
<223> OTHER INFORMATION: Synthetically generated protein
<221> NAME/KEY: VARIANT
<222> LOCATION: (1)...(7)
<223> OTHER INFORMATION: Xaa = Any Amino Acid

<400> SEQUENCE: 24

Met Xaa Ser Xaa Xaa Asn Asp
 1               5
```

```
<210> SEQ ID NO 25
<211> LENGTH: 10
<212> TYPE: DNA
<213> ORGANISM: Ovine

<400> SEQUENCE: 25
agacugagug                                                            10

<210> SEQ ID NO 26
<211> LENGTH: 10
<212> TYPE: DNA
<213> ORGANISM: Ovine

<400> SEQUENCE: 26
ugagugaugg                                                            10

<210> SEQ ID NO 27
<211> LENGTH: 10
<212> TYPE: DNA
<213> ORGANISM: Ovine

<400> SEQUENCE: 27
cgggugcuuu                                                            10

<210> SEQ ID NO 28
<211> LENGTH: 10
<212> TYPE: DNA
<213> ORGANISM: Ovine

<400> SEQUENCE: 28
gugauggcuu                                                            10

<210> SEQ ID NO 29
<211> LENGTH: 8
<212> TYPE: PRT
<213> ORGANISM: Ovine

<400> SEQUENCE: 29

Asp Val Lys Glu Phe Leu Ala Lys
 1               5

<210> SEQ ID NO 30
<211> LENGTH: 14
<212> TYPE: PRT
<213> ORGANISM: Artificial Sequence
<220> FEATURE:
<223> OTHER INFORMATION: Acetylated synthetically generated protein
<221> NAME/KEY: VARIANT
<222> LOCATION: (1)...(14)
<223> OTHER INFORMATION: Xaa = Any Amino Acid

<400> SEQUENCE: 30

Xaa Ser Ala Asn Pro Asn Asp Val Gln Glu Phe Leu Ala Lys
 1               5                  10

<210> SEQ ID NO 31
<211> LENGTH: 14
<212> TYPE: PRT
<213> ORGANISM: Artificial Sequence
<220> FEATURE:
<223> OTHER INFORMATION: Acetylated synthetically generated protein
<221> NAME/KEY: VARIANT
<222> LOCATION: (1)...(14)
<223> OTHER INFORMATION: Xaa = Any Amino Acid
```

-continued

```
<400> SEQUENCE: 31

Xaa Ala Ser Asn Pro Asn Asp Val Lys Glu Phe Leu Ala Lys
 1               5                  10

<210> SEQ ID NO 32
<211> LENGTH: 15
<212> TYPE: PRT
<213> ORGANISM: Artificial Sequence
<220> FEATURE:
<223> OTHER INFORMATION: Acetylated synthetically generated protein
<221> NAME/KEY: VARIANT
<222> LOCATION: (1)...(15)
<223> OTHER INFORMATION: Xaa = Any Amino Acid

<400> SEQUENCE: 32

Xaa Ala Ser Gly Gly Pro Asn Asp Val Lys Glu Phe Leu Ala Lys
 1               5                  10                  15

<210> SEQ ID NO 33
<211> LENGTH: 15
<212> TYPE: PRT
<213> ORGANISM: Artificial Sequence
<220> FEATURE:
<223> OTHER INFORMATION: Acetylated synthetically generated protein
<221> NAME/KEY: VARIANT
<222> LOCATION: (1)...(15)
<223> OTHER INFORMATION: Xaa = Any Amino Acid

<400> SEQUENCE: 33

Xaa Ala Ser Asn Pro Gly Gly Asp Val Lys Glu Phe Leu Ala Lys
 1               5                  10                  15

<210> SEQ ID NO 34
<211> LENGTH: 343
<212> TYPE: PRT
<213> ORGANISM: Homo sapiens

<400> SEQUENCE: 34

Met Ala Ser Asn Ser Ser Asp Val Lys Glu Phe Leu Ala Lys Ala Lys
 1               5                  10                  15

Glu Asp Phe Leu Lys Lys Trp Glu Ser Pro Ala Gln Asn Thr Ala His
                20                  25                  30

Leu Asp Gln Phe Glu Arg Ile Lys Thr Leu Gly Thr Gly Ser Phe Gly
            35                  40                  45

Arg Val Met Leu Val Lys His Lys Glu Thr Gly Asn His Tyr Ala Met
        50                  55                  60

Lys Ile Leu Asp Lys Gln Lys Val Val Lys Leu Lys Gln Ile Glu His
 65                  70                  75                  80

Thr Leu Asn Glu Lys Arg Ile Leu Gln Ala Val Asn Phe Pro Phe Leu
                85                  90                  95

Val Lys Leu Glu Phe Ser Phe Lys Asp Asn Ser Asn Leu Tyr Met Val
                100                 105                 110

Met Glu Tyr Val Pro Gly Gly Glu Met Phe Ser His Leu Arg Arg Ile
            115                 120                 125

Gly Arg Phe Ser Glu Pro His Ala Arg Phe Tyr Ala Ala Gln Ile Val
        130                 135                 140

Leu Thr Phe Glu Tyr Leu His Ser Leu Asp Leu Ile Tyr Arg Asp Leu
145                 150                 155                 160

Lys Pro Glu Asn Leu Leu Ile Asp Gln Gln Gly Tyr Ile Gln Val Thr
                165                 170                 175
```

```
Asp Phe Gly Phe Ala Lys Arg Val Lys Gly Arg Thr Trp Thr Leu Cys
            180                 185                 190

Gly Thr Pro Glu Tyr Leu Ala Pro Glu Ile Ile Leu Ser Lys Gly Tyr
            195                 200                 205

Asn Lys Ala Val Asp Trp Trp Ala Leu Gly Val Leu Ile Tyr Glu Met
            210                 215                 220

Ala Ala Gly Tyr Pro Pro Phe Ala Asp Gln Pro Ile Gln Ile Tyr
225                 230                 235                 240

Glu Lys Ile Val Ser Gly Lys Val Arg Phe Pro Ser His Phe Ser Ser
            245                 250                 255

Asp Leu Lys Asp Leu Leu Arg Asn Leu Leu Gln Val Asp Leu Thr Lys
            260                 265                 270

Arg Phe Gly Asn Leu Lys Asn Gly Val Asn Asp Ile Lys Asn His Lys
            275                 280                 285

Trp Phe Ala Thr Thr Asp Trp Ile Ala Ile Tyr Gln Arg Lys Val Glu
            290                 295                 300

Ala Pro Phe Ile Pro Lys Phe Lys Gly Pro Gly Asp Thr Ser Asn Phe
305                 310                 315                 320

Asp Asp Tyr Glu Glu Glu Ile Arg Val Ser Ile Asn Glu Lys Cys
            325                 330                 335

Gly Lys Glu Phe Ser Glu Phe
            340

<210> SEQ ID NO 35
<211> LENGTH: 2608
<212> TYPE: DNA
<213> ORGANISM: Homo sapiens
<220> FEATURE:
<221> NAME/KEY: CDS
<222> LOCATION: (164)...(1192)

<400> SEQUENCE: 35
cccagtggcc tctgggttgg gtttctcttc ctgctcccac cccacggctc cctagctccc        60
cctgcaggca gggttctggg gacagacagc cgaacagaca cggcaggtct catgagcctt       120
cccagccacc gtagtgccgg tgccctgaga acaggactga gtg atg gct tcc aac        175
                                              Met Ala Ser Asn
                                                1 tcc agc gat gtg aaa gaa ttc tta gcc aaa gcc aaa gaa gat ttt ctt        223
Ser Ser Asp Val Lys Glu Phe Leu Ala Lys Ala Lys Glu Asp Phe Leu
  5                  10                  15                  20 aaa aaa tgg gaa agt ccc gct cag aac aca gcc cac ttg gat cag ttt        271
Lys Lys Trp Glu Ser Pro Ala Gln Asn Thr Ala His Leu Asp Gln Phe
                 25                  30                  35 gaa cga atc aag acc ctc ggc acg ggc tcc ttc ggg cgg gtg atg ctg        319
Glu Arg Ile Lys Thr Leu Gly Thr Gly Ser Phe Gly Arg Val Met Leu
             40                  45                  50 gtg aaa cac aag gag acc ggg aac cac tat gcc atg aag atc ctc gac        367
Val Lys His Lys Glu Thr Gly Asn His Tyr Ala Met Lys Ile Leu Asp
         55                  60                  65 aaa cag aag gtg gtg aaa ctg aaa cag atc gaa cac acc ctg aat gaa        415
Lys Gln Lys Val Val Lys Leu Lys Gln Ile Glu His Thr Leu Asn Glu
     70                  75                  80 aag cgc atc ctg caa gct gtc aac ttt ccg ttc ctc gtc aaa ctc gag        463
Lys Arg Ile Leu Gln Ala Val Asn Phe Pro Phe Leu Val Lys Leu Glu
 85                  90                  95                 100 ttc tcc ttc aag gac aac tca aac tta tac atg gtc atg gag tac gtg        511
Phe Ser Phe Lys Asp Asn Ser Asn Leu Tyr Met Val Met Glu Tyr Val
                105                 110                 115
```

-continued

| | | | | | | | | | | | | | | | |
|---|---|---|---|---|---|---|---|---|---|---|---|---|---|---|---|
| ccc | ggc | ggg | gag | atg | ttc | tca | cac | cta | cgg | cgg | atc | gga | agg | ttc | agt | 559
| Pro | Gly | Gly | Glu | Met | Phe | Ser | His | Leu | Arg | Arg | Ile | Gly | Arg | Phe | Ser |
| | | 120 | | | | | 125 | | | | | 130 | | | |
| gag | ccc | cat | gcc | cgt | ttc | tac | gcg | gcc | cag | atc | gtc | ctg | acc | ttt | gag | 607
| Glu | Pro | His | Ala | Arg | Phe | Tyr | Ala | Ala | Gln | Ile | Val | Leu | Thr | Phe | Glu |
| | | 135 | | | | | 140 | | | | | 145 | | | |
| tat | ctg | cac | tcg | ctg | gat | ctc | atc | tac | agg | gac | ctg | aag | ccg | gag | aat | 655
| Tyr | Leu | His | Ser | Leu | Asp | Leu | Ile | Tyr | Arg | Asp | Leu | Lys | Pro | Glu | Asn |
| | 150 | | | | | 155 | | | | | 160 | | | | |
| ctc | ctc | att | gac | cag | cag | ggc | tac | att | cag | gtg | aca | gac | ttc | ggt | ttc | 703
| Leu | Leu | Ile | Asp | Gln | Gln | Gly | Tyr | Ile | Gln | Val | Thr | Asp | Phe | Gly | Phe |
| 165 | | | | | 170 | | | | | 175 | | | | | 180 |
| gcc | aag | cgc | gtg | aag | ggc | cgc | act | tgg | acc | ttg | tgc | ggc | acc | cct | gag | 751
| Ala | Lys | Arg | Val | Lys | Gly | Arg | Thr | Trp | Thr | Leu | Cys | Gly | Thr | Pro | Glu |
| | | | 185 | | | | | 190 | | | | | 195 | | |
| tac | ctg | gcc | cct | gag | att | atc | ctg | agc | aaa | ggc | tac | aac | aag | gcc | gtg | 799
| Tyr | Leu | Ala | Pro | Glu | Ile | Ile | Leu | Ser | Lys | Gly | Tyr | Asn | Lys | Ala | Val |
| | | | 200 | | | | | 205 | | | | | 210 | | |
| gac | tgg | tgg | gcc | ctg | ggg | gtt | ctt | atc | tat | gaa | atg | gcc | gct | ggc | tac | 847
| Asp | Trp | Trp | Ala | Leu | Gly | Val | Leu | Ile | Tyr | Glu | Met | Ala | Ala | Gly | Tyr |
| | | 215 | | | | | 220 | | | | | 225 | | | |
| ccg | ccc | ttc | ttc | gca | gac | cag | ccc | atc | cag | atc | tat | gag | aag | atc | gtc | 895
| Pro | Pro | Phe | Phe | Ala | Asp | Gln | Pro | Ile | Gln | Ile | Tyr | Glu | Lys | Ile | Val |
| | 230 | | | | | 235 | | | | | 240 | | | | |
| tct | ggg | aag | gtg | cgc | ttc | cct | tcc | cac | ttc | agc | tct | gac | ttg | aag | gac | 943
| Ser | Gly | Lys | Val | Arg | Phe | Pro | Ser | His | Phe | Ser | Ser | Asp | Leu | Lys | Asp |
| 245 | | | | | 250 | | | | | 255 | | | | | 260 |
| ctg | ctg | cgg | aac | ctc | ctg | cag | gta | gat | ctc | acc | aag | cgc | ttt | ggg | aac | 991
| Leu | Leu | Arg | Asn | Leu | Leu | Gln | Val | Asp | Leu | Thr | Lys | Arg | Phe | Gly | Asn |
| | | | | 265 | | | | | 270 | | | | | 275 | |
| ctc | aag | aat | ggg | gtc | aac | gat | atc | aag | aac | cac | aag | tgg | ttt | gcc | aca | 1039
| Leu | Lys | Asn | Gly | Val | Asn | Asp | Ile | Lys | Asn | His | Lys | Trp | Phe | Ala | Thr |
| | | | 280 | | | | | 285 | | | | | 290 | | |
| act | gac | tgg | att | gcc | atc | tac | cag | agg | aag | gtg | gaa | gct | ccc | ttc | ata | 1087
| Thr | Asp | Trp | Ile | Ala | Ile | Tyr | Gln | Arg | Lys | Val | Glu | Ala | Pro | Phe | Ile |
| | | | 295 | | | | | 300 | | | | | 305 | | |
| cca | aag | ttt | aaa | ggc | cct | ggg | gat | acg | agt | aac | ttt | gac | gac | tat | gag | 1135
| Pro | Lys | Phe | Lys | Gly | Pro | Gly | Asp | Thr | Ser | Asn | Phe | Asp | Asp | Tyr | Glu |
| | 310 | | | | | 315 | | | | | 320 | | | | |
| gaa | gaa | gaa | atc | cgg | gtc | tcc | atc | aat | gag | aag | tgt | ggc | aag | gag | ttt | 1183
| Glu | Glu | Glu | Ile | Arg | Val | Ser | Ile | Asn | Glu | Lys | Cys | Gly | Lys | Glu | Phe |
| 325 | | | | | 330 | | | | | 335 | | | | | 340 |

| | | | | |
|---|---|---|---|---|
| tct | gag | ttt | tagggcatg | cctgtgcccc catgggtttt cttttttctt | 1232
| Ser | Glu | Phe | | | tttcttttt tttggtcggg ggggtgggag ggttggattg aacagccaga gggccccaga 1292 gttccttgca tctaatttca cccccacccc accctccagg gttagggga gcaggaagcc 1352 cagataatca gagggacaga aacaccagct gctccccctc atccccttca ccctcctgcc 1412 ccctctccca cttttccctt cctctttccc cacagcccc cagcccctca gccctcccag 1472 cccacttctg cctgttttaa acgactttct caactccagt cagaccaggt cttgctggtg 1532 tatccaggga cagggtatgg aaagaggggc tcacgcttaa ctccagcccc cacccacacc 1592 cccatcccac ccaaccacag gccccacttg ctaagggcaa atgaacgaag cgccaacctt 1652 cctttcggag taatcctgcc tgggaaggag agatttttag tgacatgttc agtgggttgc 1712 ttgctagaat ttttttaaaa aaacaacaat ttaaatcttt atttaagttc caccagtgcc 1772 tccctccctc cttcctctac tcccaccccct cccatgtccc cccattcctc aaatccattt 1832

-continued

```
taaagagaag cagactgact ttggaaaggg aggcgctggg gtttgaacct ccccgctgct    1892
aatctcccct gggcccctcc ccggggaatc ctctctgcca atcctgcgag ggtctaggcc    1952
cctttaggaa gcctccgctc tctttttccc caacagacct gtcttcaccc ttgggctttg    2012
aaagccagac aaagcagctg cccctctccc tgccaaagag gagtcatccc ccaaaaagac    2072 agaggggag  cccaagccc  aagtctttcc  tcccagcagc  gtttccccc  aactccttaa    2132 ttttattctc cgctagattt taacgtccag ccttccctca gctgagtggg gagggcatcc    2192
ctgcaaaagg gaacagaaga ggccaagtcc cccaagcca cggcccgggg ttcaaggcta     2252
gagctgctgg ggagggctg  cctgttttac tcacccacca gcttccgcct ccccatcct    2312 gggcgcccct cctccagctt agctgtcagc tgtccatcac ctctcccca ctttctcatt    2372 tgtgctttt  tctctcgtaa tagaaaagtg gggagccgct ggggagccac cccattcatc    2432
cccgtatttc cccctctcat aacttctccc catcccagga ggagttctca ggcctggggt    2492
ggggccccgg gtgggtgcgg gggcgattca acctgtgtgc tgcgaaggac gagacttcct    2552
cttgaacagt gtgctgttgt aaacatattt gaaaactatt accaataaag tttgtt        2608
```

<210> SEQ ID NO 36
<211> LENGTH: 7
<212> TYPE: PRT
<213> ORGANISM: Homo sapiens

<400> SEQUENCE: 36

Met Ala Ser Asn Ser Ser Asp
 1               5

<210> SEQ ID NO 37
<211> LENGTH: 21
<212> TYPE: DNA
<213> ORGANISM: Homo sapiens

<400> SEQUENCE: 37
atggcttcca actccagcga t                                              21

<210> SEQ ID NO 38
<211> LENGTH: 343
<212> TYPE: PRT
<213> ORGANISM: Mus musculus

<400> SEQUENCE: 38

Met Ala Ser Ser Asn Asp Val Lys Glu Phe Leu Ala Lys Ala Lys
 1               5                  10                  15

Glu Asp Phe Leu Lys Lys Trp Glu Asp Pro Ser Gln Asn Thr Ala Gln
                20                  25                  30

Leu Asp Gln Phe Asp Arg Ile Lys Thr Leu Gly Thr Gly Ser Phe Gly
            35                  40                  45

Arg Val Met Leu Val Lys His Lys Glu Ser Gly Asn His Tyr Ala Met
        50                  55                  60

Lys Ile Leu Asp Lys Gln Lys Val Val Lys Leu Lys Gln Ile Glu His
    65                  70                  75                  80

Thr Leu Asn Glu Lys Arg Ile Leu Gln Ala Val Asn Phe Pro Phe Leu
                85                  90                  95

Val Lys Leu Glu Phe Ser Phe Lys Asp Asn Ser Asn Leu Tyr Met Val
                100                 105                 110

Met Glu Tyr Val Ala Gly Gly Glu Met Phe Ser His Leu Arg Arg Ile
            115                 120                 125

```
Gly Arg Phe Ser Glu Pro His Ala Arg Phe Tyr Ala Ala Gln Ile Val
    130                 135                 140

Leu Thr Phe Glu Tyr Leu His Ser Leu Asp Leu Ile Tyr Arg Asp Leu
145                 150                 155                 160

Lys Pro Glu Asn Leu Leu Ile Asp Gln Gln Gly Tyr Ile Gln Val Thr
                165                 170                 175

Asp Phe Gly Phe Ala Lys Arg Val Lys Gly Arg Thr Trp Thr Leu Cys
            180                 185                 190

Gly Thr Pro Glu Tyr Leu Ala Pro Glu Ile Ile Leu Ser Lys Gly Tyr
        195                 200                 205

Asn Lys Ala Val Asp Trp Trp Ala Leu Gly Val Leu Ile Tyr Glu Met
    210                 215                 220

Ala Ala Gly Tyr Pro Pro Phe Phe Ala Asp Gln Pro Ile Gln Ile Tyr
225                 230                 235                 240

Glu Lys Ile Val Ser Gly Lys Val Arg Phe Pro Ser His Phe Ser Ser
                245                 250                 255

Asp Leu Lys Asp Leu Leu Arg Asn Leu Leu Gln Val Asp Leu Thr Lys
            260                 265                 270

Arg Phe Gly Asn Leu Lys Asp Gly Val Asn Asp Ile Lys Asn His Lys
        275                 280                 285

Trp Phe Ala Thr Thr Asp Trp Ile Ala Ile Tyr Gln Arg Lys Val Glu
    290                 295                 300

Ala Pro Phe Ile Pro Lys Phe Lys Gly Pro Gly Asp Thr Ser Asn Phe
305                 310                 315                 320

Asp Asp Tyr Glu Glu Glu Glu Ile Arg Val Ser Ile Asn Glu Lys Cys
                325                 330                 335

Gly Lys Glu Phe Thr Glu Phe
            340
```

```
<210> SEQ ID NO 39
<211> LENGTH: 2211
<212> TYPE: DNA
<213> ORGANISM: Mus musculus
<220> FEATURE:
<221> NAME/KEY: CDS
<222> LOCATION: (191)...(1219)

<400> SEQUENCE: 39
```

```
gggttctatc tgcccctacc ctgcacccat tagtctgcag gttgagtttc tcttcctgtt     60
cccaccctat cactccctgg ctccctctac aggcagggct ccccccaggg actggcagcc    120
aaactgctgc agcagatctt atgaggcttc cgagccaccg taatgctagt gccctgagaa    180
agactgagtg atg gct tcc agc tcc aac gat gtg aaa gag ttc cta gcc       229
            Met Ala Ser Ser Ser Asn Asp Val Lys Glu Phe Leu Ala
                1               5                   10 aaa gcc aag gaa gat ttc ctg aaa aaa tgg gaa gac ccc tct cag aat      277
Lys Ala Lys Glu Asp Phe Leu Lys Lys Trp Glu Asp Pro Ser Gln Asn
        15                  20                  25 aca gcc cag ttg gat cag ttt gat aga atc aag acc ctt ggc acc ggc      325
Thr Ala Gln Leu Asp Gln Phe Asp Arg Ile Lys Thr Leu Gly Thr Gly
 30                  35                  40                  45 tcc ttt ggg cga gtg atg ctg gtg aag cac aag gag agt ggg aac cac      373
Ser Phe Gly Arg Val Met Leu Val Lys His Lys Glu Ser Gly Asn His
                50                  55                  60 tac gcc atg aag atc tta gac aag cag aag gtg gtg aag cta aag cag      421
Tyr Ala Met Lys Ile Leu Asp Lys Gln Lys Val Val Lys Leu Lys Gln
            65                  70                  75
```

```
atc gag cac act ctg aat gag aag cgc atc ctg cag gcc gtc aac ttc    469
Ile Glu His Thr Leu Asn Glu Lys Arg Ile Leu Gln Ala Val Asn Phe
         80                  85                  90 ccg ttc ctg gtc aaa ctt gaa ttc tcc ttc aag gac aac tca aac ctg    517
Pro Phe Leu Val Lys Leu Glu Phe Ser Phe Lys Asp Asn Ser Asn Leu
 95                 100                 105 tac atg gtc atg gag tat gta gct ggt ggc gag atg ttc tcc cac cta    565
Tyr Met Val Met Glu Tyr Val Ala Gly Gly Glu Met Phe Ser His Leu
110                 115                 120                 125 cgg cgg att gga agg ttc agc gag ccc cat gcc cgt ttc tac gcg gcg    613
Arg Arg Ile Gly Arg Phe Ser Glu Pro His Ala Arg Phe Tyr Ala Ala
                130                 135                 140 cag atc gtc ctg acc ttt gag tat ctg cac tcc ctg gac ctc atc tac    661
Gln Ile Val Leu Thr Phe Glu Tyr Leu His Ser Leu Asp Leu Ile Tyr
            145                 150                 155 cgg gac ctg aag ccc gag aat ctt ctc atc gac cag cag ggc tat att    709
Arg Asp Leu Lys Pro Glu Asn Leu Leu Ile Asp Gln Gln Gly Tyr Ile
        160                 165                 170 cag gtg aca gac ttc ggt ttt gcc aag cgt gtg aaa ggc cgt act tgg    757
Gln Val Thr Asp Phe Gly Phe Ala Lys Arg Val Lys Gly Arg Thr Trp
    175                 180                 185 acc ttg tgt ggg acc cct gag tac ttg gcc ccc gag att atc ctg agc    805
Thr Leu Cys Gly Thr Pro Glu Tyr Leu Ala Pro Glu Ile Ile Leu Ser
190                 195                 200                 205 aaa ggc tac aac aag gct gtg gac tgg tgg gct ctc gga gtc ctc atc    853
Lys Gly Tyr Asn Lys Ala Val Asp Trp Trp Ala Leu Gly Val Leu Ile
                210                 215                 220 tac gag atg gct gct ggt tac cca ccc ttc ttc gct gac cag cct atc    901
Tyr Glu Met Ala Ala Gly Tyr Pro Pro Phe Phe Ala Asp Gln Pro Ile
            225                 230                 235 cag atc tat gag aaa atc gtc tct ggg aag gtg cgg ttc cca tcc cac    949
Gln Ile Tyr Glu Lys Ile Val Ser Gly Lys Val Arg Phe Pro Ser His
        240                 245                 250 ttc agc tct gac ttg aag gac ctg ctg cgg aac ctt ctg caa gtg gat    997
Phe Ser Ser Asp Leu Lys Asp Leu Leu Arg Asn Leu Leu Gln Val Asp
    255                 260                 265 cta acc aag cgc ttt gga aac ctc aag gac ggg gtc aat gac atc aag   1045
Leu Thr Lys Arg Phe Gly Asn Leu Lys Asp Gly Val Asn Asp Ile Lys
270                 275                 280                 285 aac cac aag tgg ttt gcc acg act gac tgg att gcc atc tat cag aga   1093
Asn His Lys Trp Phe Ala Thr Thr Asp Trp Ile Ala Ile Tyr Gln Arg
                290                 295                 300 aag gtg gaa gct ccc ttc ata cca aag ttt aaa ggc cct ggg gac acg   1141
Lys Val Glu Ala Pro Phe Ile Pro Lys Phe Lys Gly Pro Gly Asp Thr
            305                 310                 315 agt aac ttt gac gac tat gag gag gaa gag atc cgg gtc tcc atc aat   1189
Ser Asn Phe Asp Asp Tyr Glu Glu Glu Glu Ile Arg Val Ser Ile Asn
        320                 325                 330 gag aag tgt ggc aag gag ttt act gag ttt tagggctgtg cttgtgcccc     1239
Glu Lys Cys Gly Lys Glu Phe Thr Glu Phe
335                 340 ttgggttctc tttcattttt tcttttttctt tctattttt ttccggttgg gggtgggagg  1299
gttggatcgg aacagccaga gggccctaga gttccatgca tctaatttaa catccactcc  1359
acacccccag ggttaaggag agcaggaaag cgcttccaga ttactgggga agggcaacat  1419
cagctgctcc cccatccct tgttgtccac ccttcccttc ctgttttaat gaatttctta  1479
gctccagcca tacccaatct tgctggtgta tccagggca gggtacggaa agagggcccc   1539
aaattcagcc tccttcccga ccctagcact ggatactaag gatgaacgaa cagtaacgcc  1599
```

-continued

```
aaccttccct tccatgcagc cctacctgga aagggagatt ttatgacctg tacagagggc    1659
tgcttgccag tgggtttttt ttttcattta aattaagttc caccagtgcc tcccaccctc    1719
caaattgtcc caccctcccc aaacaccctc ctcactccct aaatcaattc tgatgagacc    1779
tgggtagcca actgaccctg tcaaggaagg aactgggctt ggaatctcgc cctgagctgc    1839
tagctcccgg ccccctttc cagtggtctc atgccaattt gtcctgtgca tcagccccct     1899
taagaagcct ccccatcctg gcgcctcgct tctagcttag ctgtcagctg tccatcacct    1959
cttgccgtgc gtccccactc actgcaaccc caagtctgat tgtgcttttt ctctcaatag    2019
aaaggtgggg agctgctggg gaaattaccc catttatccc tgtgtttatc cctcgtcgta    2079
acttctccca aaaaggagga gctctcaggc ctgggtgggg gccccgggtg gacgaggggg    2139
tcgtcaacct gtgtgcttca aggatgaga cttcctcttg aacagtgtgc tgttgtaaac     2199
atatttgaaa ac                                                        2211
```

<210> SEQ ID NO 40
<211> LENGTH: 7
<212> TYPE: PRT
<213> ORGANISM: Mus musculus

<400> SEQUENCE: 40

```
Met Ala Ser Ser Ser Asn Asp
 1               5
```

<210> SEQ ID NO 41
<211> LENGTH: 21
<212> TYPE: DNA
<213> ORGANISM: Mus musculus

<400> SEQUENCE: 41

```
atggcttcca gctccaacga t                                              21
```

<210> SEQ ID NO 42
<211> LENGTH: 595
<212> TYPE: DNA
<213> ORGANISM: Homo sapiens
<220> FEATURE:
<221> NAME/KEY: CDS
<222> LOCATION: (164)...(595)
<221> NAME/KEY: misc_feature
<222> LOCATION: (1)...(595)
<223> OTHER INFORMATION: n = A,T,C or G

<400> SEQUENCE: 42

```
cccagtggcc tctggttgg gtttctcttc ctgctcccac cccacggctc cctagctccc      60
cctgcaggca gggttctggg acagacagc cgaacagaca cggcaggtct catgagcctt     120
cccagccacc gtagtgccgg tgccctgaga acaggactga gtg atg gct tcc aac     175
                                             Met Ala Ser Asn
                                              1 tcc agc gat gtg aaa gaa ttc tta gcc aaa gcc aaa gaa gat ttt ctt     223
Ser Ser Asp Val Lys Glu Phe Leu Ala Lys Ala Lys Glu Asp Phe Leu
 5                  10                  15                  20 aaa aaa tgg gaa agt ccc gct cag aac aca gcc cac ttg gat cag ttt     271
Lys Lys Trp Glu Ser Pro Ala Gln Asn Thr Ala His Leu Asp Gln Phe
                25                  30                  35 gaa cga atc aag acc ctc ggc acg ggc tcc ttc ggg cgg gtg atg ctg     319
Glu Arg Ile Lys Thr Leu Gly Thr Gly Ser Phe Gly Arg Val Met Leu
            40                  45                  50
```

```
gtg aaa cac aag gag acc ggg aac cac tat gcc atg aag atc ctc gac    367
Val Lys His Lys Glu Thr Gly Asn His Tyr Ala Met Lys Ile Leu Asp
         55                  60                  65 aaa cag aag gtg gtg aaa ctg aaa cag atc gaa cac acc ctg aat gaa    415
Lys Gln Lys Val Val Lys Leu Lys Gln Ile Glu His Thr Leu Asn Glu
 70                  75                  80 aag cgc atc ctg caa gct gtc aac ttt ccg ttc ctc gtc aaa ctc gag    463
Lys Arg Ile Leu Gln Ala Val Asn Phe Pro Phe Leu Val Lys Leu Glu
 85                  90                  95                 100 ttc tcc ttc aag gac aac tca aac tta tac atg gtc atg gag tac gtg    511
Phe Ser Phe Lys Asp Asn Ser Asn Leu Tyr Met Val Met Glu Tyr Val
             105                 110                 115 ccc ggc ggg gag atg ttc tca cac cta cgg cgg atc gga agg ttc agt    559
Pro Gly Gly Glu Met Phe Ser His Leu Arg Arg Ile Gly Arg Phe Ser
         120                 125                 130 gag ccc cat gcc cgt ttc tac gcg gcc cag atc gtn                    595
Glu Pro His Ala Arg Phe Tyr Ala Ala Gln Ile Val
             135                 140
```

<210> SEQ ID NO 43
<211> LENGTH: 144
<212> TYPE: PRT
<213> ORGANISM: Homo sapiens

<400> SEQUENCE: 43

```
Met Ala Ser Asn Ser Ser Asp Val Lys Glu Phe Leu Ala Lys Ala Lys
 1               5                  10                  15

Glu Asp Phe Leu Lys Lys Trp Glu Ser Pro Ala Gln Asn Thr Ala His
             20                  25                  30

Leu Asp Gln Phe Glu Arg Ile Lys Thr Leu Gly Thr Gly Ser Phe Gly
         35                  40                  45

Arg Val Met Leu Val Lys His Lys Glu Thr Gly Asn His Tyr Ala Met
     50                  55                  60

Lys Ile Leu Asp Lys Gln Lys Val Val Lys Leu Lys Gln Ile Glu His
 65                  70                  75                  80

Thr Leu Asn Glu Lys Arg Ile Leu Gln Ala Val Asn Phe Pro Phe Leu
                 85                  90                  95

Val Lys Leu Glu Phe Ser Phe Lys Asp Asn Ser Asn Leu Tyr Met Val
             100                 105                 110

Met Glu Tyr Val Pro Gly Gly Glu Met Phe Ser His Leu Arg Arg Ile
         115                 120                 125

Gly Arg Phe Ser Glu Pro His Ala Arg Phe Tyr Ala Ala Gln Ile Val
     130                 135                 140
```

<210> SEQ ID NO 44
<211> LENGTH: 622
<212> TYPE: DNA
<213> ORGANISM: Mus musculus
<220> FEATURE:
<221> NAME/KEY: CDS
<222> LOCATION: (191)...(622)
<221> NAME/KEY: misc_feature
<222> LOCATION: (1)...(622)
<223> OTHER INFORMATION: n = A,T,C or G

<400> SEQUENCE: 44

```
gggttctatc tgcccctacc ctgcacccat tagtctgcag gttgagtttc tcttcctgtt     60
cccaccctat cactccctgg ctccctctac aggcagggct cccccccagg actggcagcc    120
aaactgctgc agcagatctt atgaggcttc cgagccaccg taatgctagt gccctgagaa    180
```

```
agactgagtg atg gct tcc agc tcc aac gat gtg aaa gag ttc cta gcc         229
           Met Ala Ser Ser Ser Asn Asp Val Lys Glu Phe Leu Ala
            1               5                  10 aaa gcc aag gaa gat ttc ctg aaa aaa tgg gag acc cct tct cag aat         277
Lys Ala Lys Glu Asp Phe Leu Lys Lys Trp Glu Thr Pro Ser Gln Asn
 15              20                  25 aca gcc cag ttg gat cag ttt gat aga atc aag acc ctt ggc acc ggc         325
Thr Ala Gln Leu Asp Gln Phe Asp Arg Ile Lys Thr Leu Gly Thr Gly
 30              35                  40                  45 tcc ttt ggg cga gtg atg ctg gtg aag cac aag gag agt ggg aac cac         373
Ser Phe Gly Arg Val Met Leu Val Lys His Lys Glu Ser Gly Asn His
                 50                  55                  60 tac gcc atg aag atc tta gac aag cag aag gtg gtg aag cta aag cag         421
Tyr Ala Met Lys Ile Leu Asp Lys Gln Lys Val Val Lys Leu Lys Gln
             65                  70                  75 atc gag cac act ctg aat gag aag cgc atc ctg cag gcc gtc aac ttc         469
Ile Glu His Thr Leu Asn Glu Lys Arg Ile Leu Gln Ala Val Asn Phe
         80                  85                  90 ccg ttc ctg ctc aaa ctt gaa ttc tcc ttc aag gac aac tca aac ctg         517
Pro Phe Leu Leu Lys Leu Glu Phe Ser Phe Lys Asp Asn Ser Asn Leu
     95                 100                 105 tac atg gtc atg gag tat gta gct ggt ggc gag atg ttc tcc cac cta         565
Tyr Met Val Met Glu Tyr Val Ala Gly Gly Glu Met Phe Ser His Leu
110                 115                 120                 125 cgg cgg att gga agg ttc agc gag ccc cat gcc cgt ttc tac gcg gcg         613
Arg Arg Ile Gly Arg Phe Ser Glu Pro His Ala Arg Phe Tyr Ala Ala
                130                 135                 140 cag atc gtn                                                             622
Gln Ile Val <210> SEQ ID NO 45
<211> LENGTH: 144
<212> TYPE: PRT
<213> ORGANISM: Mus musculus

<400> SEQUENCE: 45

Met Ala Ser Ser Ser Asn Asp Val Lys Glu Phe Leu Ala Lys Ala Lys
 1               5                  10                  15

Glu Asp Phe Leu Lys Lys Trp Glu Thr Pro Ser Gln Asn Thr Ala Gln
             20                  25                  30

Leu Asp Gln Phe Asp Arg Ile Lys Thr Leu Gly Thr Gly Ser Phe Gly
         35                  40                  45

Arg Val Met Leu Val Lys His Lys Glu Ser Gly Asn His Tyr Ala Met
     50                  55                  60

Lys Ile Leu Asp Lys Gln Lys Val Val Lys Leu Lys Gln Ile Glu His
 65                  70                  75                  80

Thr Leu Asn Glu Lys Arg Ile Leu Gln Ala Val Asn Phe Pro Phe Leu
                 85                  90                  95

Leu Lys Leu Glu Phe Ser Phe Lys Asp Asn Ser Asn Leu Tyr Met Val
            100                 105                 110

Met Glu Tyr Val Ala Gly Gly Glu Met Phe Ser His Leu Arg Arg Ile
        115                 120                 125

Gly Arg Phe Ser Glu Pro His Ala Arg Phe Tyr Ala Ala Gln Ile Val
    130                 135                 140

<210> SEQ ID NO 46
<211> LENGTH: 6
<212> TYPE: PRT
<213> ORGANISM: Homo sapiens
```

-continued

```
<400> SEQUENCE: 46

Ala Ser Asn Ser Ser Asp
  1               5

<210> SEQ ID NO 47
<211> LENGTH: 6
<212> TYPE: PRT
<213> ORGANISM: Mus musculus

<400> SEQUENCE: 47

Ala Ser Ser Ser Asn Asp
  1               5

<210> SEQ ID NO 48
<211> LENGTH: 18
<212> TYPE: DNA
<213> ORGANISM: Homo sapiens

<400> SEQUENCE: 48
gcttccaact ccagcgat                                                   18

<210> SEQ ID NO 49
<211> LENGTH: 18
<212> TYPE: DNA
<213> ORGANISM: Mus musculus

<400> SEQUENCE: 49
gcttccagct ccaacgat                                                   18

<210> SEQ ID NO 50
<211> LENGTH: 23
<212> TYPE: RNA
<213> ORGANISM: Homo sapiens

<400> SEQUENCE: 50 cgugggugg gagcaggaag aga                                              23

<210> SEQ ID NO 51
<211> LENGTH: 25
<212> TYPE: DNA
<213> ORGANISM: Homo sapiens

<400> SEQUENCE: 51 ucuguccca gaacccugcc ugcag                                            25

<210> SEQ ID NO 52
<211> LENGTH: 10
<212> TYPE: RNA
<213> ORGANISM: Homo sapiens

<400> SEQUENCE: 52
ggacugagug                                                            10

<210> SEQ ID NO 53
<211> LENGTH: 10
<212> TYPE: RNA
<213> ORGANISM: Homo sapiens

<400> SEQUENCE: 53
gcccugagaa                                                            10

<210> SEQ ID NO 54
<211> LENGTH: 10
```

```
<212> TYPE: RNA
<213> ORGANISM: Homo sapiens

<400> SEQUENCE: 54
cucaugagcc                                                          10

<210> SEQ ID NO 55
<211> LENGTH: 51
<212> TYPE: DNA
<213> ORGANISM: Mus musculus

<400> SEQUENCE: 55
taatgctagt gccctgagaa gactgagtga tggcttccag ctccaacgat g            51

<210> SEQ ID NO 56
<211> LENGTH: 51
<212> TYPE: DNA
<213> ORGANISM: Homo sapiens

<400> SEQUENCE: 56
tgccggtgcc ctgagaacag gactgagtga tggcttccaa ctccagcgat g            51
```

SPERM ASSOCIATED PROTEIN KINASE POLYPEPTIDES, CORRESPONDING NUCLEIC ACIDS, AND METHODS OF USE

CROSS REFERENCE TO RELATED APPLICATION

This application claims priority from U.S. Provisional Application Ser. No. 60/099,771, filed Sep. 10, 1998, which is incorporated herein by reference in its entirety.

STATEMENT AS TO FEDERALLY SPONSORED RESEARCH

This invention was made with government support under NIH grant number HD23858 awarded by the National Institutes of Health. The government may have certain rights in the invention.

FIELD OF THE INVENTION

The invention relates to compositions and methods for altering fertility and more specifically to sperm-specific forms of the catalytic subunit (referred to as "C") of cAMP-dependent protein kinases.

BACKGROUND OF THE INVENTION

The cAMP-dependent protein kinase (PKA) is a major enzyme in cellular signal transduction and is thought to mediate most of the physiological responses to cAMP in eukaryotic cells. Below a cAMP threshold concentration, PKA exists as an inactive tetramer of two catalytic (C) subunits and two regulatory (R) subunits that together can be represented as $CR_2C$. The two R subunits form a dimer with each protomer attaching to the substrate-binding site of a C subunit. Some isoforms of R also associate with binding proteins collectively termed A-kinase anchoring proteins; it is believed that through these interactions PKA is targeted to specific subcellular compartments.

Activation of adenylate cyclase by extracellular signals raises the intracellular concentration of cAMP, and at a certain threshold concentration cAMP binds to the R subunits of the PKA tetramer, releasing C to phosphorylate its substrates.

There are three known genes encoding mammalian C. The Cα gene appears to be expressed in most tissues, including the brain, while Cβ gene expression is detected mainly in the brain. Cγ is a transcribed retroposon that has been found in primates and whose expression is detected only in testis. Proteins expressed from recombinant clones of Cα, Cβ, and Cγ have been shown to have distinct biochemical properties.

cAMP-dependent signaling has an important role in the control of sperm movement. Mammalian sperm are nonmotile in the testis, but as they pass through the epididymis they acquire the capacity for motility. This process is known as "epididymal maturation" and is essential for the sperm to fertilize an egg. Several studies have shown that changes in sperm cAMP levels are involved in epididymal maturation. The mechanisms by which alterations in cAMP levels lead to epididymal maturation are largely unknown.

SUMMARY OF THE INVENTION

The invention is based in part on the discovery of a novel sperm-specific form of the catalytic subunit of cAMP-dependent protein kinase referred to herein as $C_s$ polypeptide, or just $C_s$, which is an alternatively spliced transcript of the Cα gene. $C_s$ is unique in that it has an acetylated amino terminus with an N-terminal amino acid sequence of six amino acids, which differs from the N-terminal sequence of all other previously described forms of C. The remainder of the amino acid sequence of $C_s$ is identical to that of Cα1, another protein encoded by the Cα gene, which was formerly referred to as the Cα protein.

The region of identity begins with the amino acids encoded by the beginning of the second exon of Cα. Thus, $C_s$ arises as a result of testis-specific splicing of an exon encoding the novel N-terminus to the remaining Cα exons. The sequence identity of the amino acids beginning with the second exon holds true in a wide variety of mammals. For example, the remainder of the sequence of ovine $C_s$ is identical to that of ovine Cα1, and the remainder of the sequence of human $C_s$ is identical to that of human Cα1.

Because $C_s$ is expressed only in testis cells (i.e., male cells), it provides a unique target for the diagnosis and therapy of fertility disorders, as well as a basis for novel male contraceptives and fertility enhancers. Thus, for example, nucleic acids encoding $C_s$ polypeptides, and agents based on these sequences, can be used for diagnosing and treating conditions associated with spermatocyte function, e.g., in the promotion or inhibition of fertility.

In general, the invention features isolated nucleic acids encoding $C_s$ polypeptides. For example, an isolated nucleic acid may encode a polypeptide comprising a first peptide linked to a second peptide, wherein the first peptide has the sequence $Xaa_1$, Ser $Xaa_2$ $Xaa_3$ $Xaa_4$ Asp (SEQ ID NO:1), where Xaa can be any amino acid, and wherein the second peptide is at least 85%, 90%, 95%, 98%, 99% or even 100% identical to a peptide having the amino acid sequence of the predicted human Cα1 amino acid sequence beginning at exon 2 (SEQ ID NO:2). This sequence is shown in FIG. 1A as part of the full amino acid sequence of the human Cα1 polypeptide (SEQ ID NO:4). The amino acid sequence corresponding to SEQ ID NO:2 begins after the "/". The nucleic acid can also encode the amino acid sequence of SEQ ID NO:2 wherein $Xaa_1$ is Ala, $Xaa_2$ is Asn or Ser, $Xaa_3$ is Ser or Pro, and $Xaa_4$ is Asn or Ser.

FIG. 1B shows the full nucleic acid sequence of human Cα (SEQ ID NO:5), including the portion beginning at exon 2 (after the "/") and ending with nucleotide 1133 (SEQ ID NO:3). Both the amino acid and nucleotide sequences of human Cα are available from GenBank at Accession No. X07767.

In other embodiments, the second peptide is at least 75% or more, e.g., 100%, identical to the Cα1 amino acid sequence beginning at exon 2 of other animals, e.g., mammalian, species of interest, such as dog, cat, horse, cow, or pig. Thus, the $C_s$ polypeptide can be designed to be species-specific, and can then be used to treat that particular species.

The amino acid sequence of the first peptide can include, e.g., Ala Ser Asn Pro Asn Asp (SEQ ID NO:6), which corresponds to the amino terminal amino acid sequence in mature ovine $C_s$, Pro Ser Ser Ser Asn Asp (SEQ ID NO:7), which corresponds to a predicted amino acid sequence encoded by a mouse pseudogene. The amino acid sequence of the first peptide can also include, e.g., Ala Ser Asn Ser Ser Asp (SEQ ID NO:46) or Ala Ser Ser Ser Asn Asp (SEQ ID NO:47). The latter sequences correspond to the amino terminal amino acid sequence in processed human and mouse $C_s$, respectively.

The nucleic acid encoding the first peptide can optionally encode the amino acid Met at the amino terminus, i.e., Met Xaa Ser Xaa Xaa Asn Asp (SEQ ID NO:24), Met Ala Ser Asn Pro Asn Asp (SEQ ID NO:8), Met Pro Ser Ser Ser Asn Asp (SEQ ID NO:9), Met Ala Ser Asn Ser Ser Asp (SEQ ID NO:36), or Met Ala Ser Ser Ser Asn Asp (SEQ ID NO:40).

The first peptide can thus be encoded by, e.g., 5'-GCTTCCAACCCCAACGAT-3' (SEQ ID NO:10), 5'-CCTTCCAGCTCCAATGAT3' (SEQ ID NO:11), 5'-ATGGCTTCCAACCCCAACGAT-3' (SEQ ID NO:12), and 5'-ATGCCTTCCAGCTCCAATGAT-3' (SEQ ID NO:13), 5'-GCTTCCAACTCCAGCGAT-3' (SEQ ID NO:48), 5'-GCTTCCAGCTC-CAACGAT-3' (SEQ ID NO:49), 5'-ATGGCTTCCAACTCCAGCGAT-3' (SEQ ID NO:37), and 5'-ATGGCTTCCAGCTCCAACGAT-3' (SEQ ID NO:41), which encode the amino acids of SEQ ID NOS: 6–9, 46–47, 36, and 40, respectively.

The isolated nucleic acid can also include a nucleic acid encoding ovine $C_s$ (SEQ ID NO:14) as shown in FIGS. 2A–C. The predicted amino acid sequence of ovine $C_s$ (SEQ ID NO:15) is also shown in FIGS. 2A–C.

In other embodiments, an isolated nucleic acid can encode a polypeptide comprising a first peptide linked to a second peptide, wherein the first peptide has the sequence Met Ala Ser Asn Ser Ser Asp (SEQ ID NO:36) or Ala Ser Asn Ser Ser Asp (SEQ ID NO:46), and the second peptide is at least 85%, 90%, 95%, 98%, 99% or even 100% identical to a peptide having the amino acid sequence of the predicted human Cα1 amino acid sequence beginning at exon 2 (SEQ ID NO:2). An example of such a nucleic acid is a nucleic acid encoding the human $C_s$ polypeptide (SEQ ID NO:34), e.g., the nucleic acid of SEQ ID NO:35.

An "isolated nucleic acid" is a nucleic acid that is not immediately contiguous with both of the coding sequences with which it is immediately contiguous (one on the 5' end and one on the 3' end) in the naturally occurring genome of the organism from which it is derived. Thus, a recombinant nucleic acid could include some or all of the 5' non-coding (e.g., promoter) sequences that are immediately contiguous to the coding sequence. The term therefore includes, for example, a recombinant DNA which is incorporated into a vector, into an autonomously replicating plasmid or virus, such as a retrovirus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA which is part of a hybrid gene encoding additional polypeptide sequence. The term "isolated $C_s$ nucleic acid" does not include $C_s$ nucleic acid mixed or otherwise associated with other, closely related C nucleic acids, e.g., those that migrate at a similar rate as $C_s$ on an electrophoresis gel.

By "linked" is meant that a first portion, e.g., a peptide, is connected to a second portion, e.g., another peptide, by a covalent bond, e.g., a peptide bond, or by a non-covalent or other type of bond.

In some embodiments, the nucleic acid encoding a $C_s$ polypeptide hybridizes under stringent conditions to a sequence complementary to 5'-ATGGCTTCCAACCCCAACGAT-3' (SEQ ID NO:12), 5'-ATGCCTTCCAGCTCCAATGAT-3' (SEQ ID NO:13), 5'-ATGGCTTCCAACTCCAGCGAT-3' (SEQ ID NO:37), and 5'-ATGGCTTCCAGCTCCAACGA-3' (SEQ ID NO:41).

Hybridization under "stringent conditions" using short $C_s$-specific oligonucleotide probes, e.g., probes having the nucleotide sequence of, or the sequence complementary to, the nucleic acids encoding the first peptide in $C_s$, e.g., of SEQ ID NOs. 1, 4, 7–9, 36, 38, 40, 46, or 47 is hybridization at 37° C. in 4×SSPE, 0.2% SDS, 0.5% non-fat dry milk and washing at 37° C. in 2×SSC, 0.2% SDS after hybridization. Such $C_s$-specific oligonucleotide probes are used under stringent conditions to determine whether a sample or unknown nucleic acid is a $C_s$ nucleic acid, i.e., a nucleic acid that encodes a $C_s$ polypeptide. If the probe hybridizes to an unknown nucleic acid under stringent conditions, then the unknown nucleic acid is a $C_s$ nucleic acid. Such $C_s$ nucleic acids encode polypeptides having some or all of the biological activities possessed by naturally-occurring $C_s$. The biological activity can be measured using one of the assays described herein.

Nucleic acids with even closer matches to the probe sequence can be identified by performing post-hybridization washes in 2×SSC, 0.2% SDS at 42° C., 45° C., 50° C., 55° C., or even 65° C.

The "identity" of a nucleic acid or amino acid sequence can be measured using sequence analysis software (Sequence Analysis Software Package of the Genetics Computer Group, University of Wisconsin Biotechnology Center, 1710 University Avenue, Madison, Wis. 53705) set to the default parameters therein. By "substantially identical" is meant a polypeptide or nucleic acid having a sequence that is at least 85% identical to the sequence of the reference amino acid or nucleic acid sequence as measured using the sequence analysis software Package set to default parameters. Other polypeptides or nucleotide sequences can be more or less "identical," e.g., 90%, 95%, 98%, or even 99% or 100% identical.

For polypeptides, the length of the reference polypeptide sequence will generally be at least 16 amino acids, preferably at least 20 amino acids, more preferably at least 25 amino acids, and most preferably 35 amino acids. For nucleic acids, the length of the reference nucleic acid sequence will generally be at least 50 nucleotides, preferably at least 60 nucleotides, more preferably at least 75 nucleotides, and most preferably 110 nucleotides.

A suitable antisense oligo for mouse $C_s$ is one that corresponds to nucleotides −187 to +16 of the nucleic acid encoding mouse $C_s$, and an antisense oligo for human $C_s$ is one that corresponds to nucleotides −140 to +16 of the nucleic acid sequence encoding human $C_s$.

In another aspect, the invention features an isolated nucleic acid comprising a nucleotide sequence complementary to all or a portion of the nucleotide sequence encoding a $C_s$ polypeptide, e.g., a nucleic acid complementary to the nucleic acid encoding the peptide of SEQ ID NO:1, SEQ ID NO:36, SEQ ID NO:40, or SEQ ID NO:46. Also included is an isolated nucleic acid complementary to a region of the 5' untranslated region (UTR) of the $C_s$ specific exon, e.g., nucleotides −29 to +22 (SEQ ID NO:20) in FIGS. 2A–C, which contains ovine 5'UTR sequences and exon 1 coding sequences, or nucleotides −29 to −1 (SEQ ID NO:21) in FIGS. 2A–C, which contains only 5'UTR sequences. Alternatively, the isolated nucleic acid may be complementary to a region including both 5' UTR and exon 1, e.g., nucleotides −20 to +22 (SEQ ID NO:22) or nucleotides −5 to +15 (SEQ ID NO:23) of FIGS. 2A–C. Also included is an isolated nucleic acid complementary to the nucleic acid encoding the polypeptide of SEQ ID NO:1 with a Met on its amino terminal end, i.e., Met Xaa$_1$ Ser Xaa$_2$ Xaa$_3$ Xaa$_4$ Asn Asp (SEQ ID NO:2). Thus, the nucleic acid can include a nucleic acid of SEQ ID NOs:16–19, which are nucleic acids complementary to the nucleic acids of SEQ ID NOS: 10–13, respectively.

In another aspect, the invention features a nucleic acid having at least 12, preferably at least 15, 18, 25, or 50 contiguous nucleotides that are at least 85% identical to nucleotides in the sequence complementary to nucleotides −29 to +22 of ovine $C_s$ (SEQ ID NO:20), murine $C_s$ (SEQ ID NO:55), or human $C_s$ (SEQ ID NO:56).

The invention also features an isolated enzymatic RNA molecule, e.g., a ribozyme, that specifically cleaves $C_s$ RNA.

In another aspect, the invention includes a vector, e.g., an expression vector, that includes a nucleic acid molecule encoding a $C_s$ polypeptide. The vector can be, for example, a plasmid or a virus. The vector may optionally include a regulatory element.

The invention also includes a host cell, e.g., a non-human mammalian cell, which contains the nucleic acid encoding a $C_s$ polypeptide. Thus, the host cell can include a vector having a nucleic acid encoding $C_s$.

The invention also features substantially pure $C_s$ polypeptides. By "polypeptide" is meant any chain of amino acids, regardless of length, and thus includes polypeptides, proteins, and peptides. A $C_s$ polypeptide must include at least an acetylated N-terminal end, and the six amino acid peptide of SEQ ID NOs:1, 6, 8, 9, 24, 36, 40, 46, or 47 at its N-terminal end.

By "substantially pure" is meant a preparation which is at least 60% by weight (dry weight) the compound of interest, i.e., a $C_s$ polypeptide, and which does not include any non-$C_s$ polypeptides that have essentially the same molecular weight as $C_s$, e.g., $C\alpha1$ polypeptides. Thus, a substantially pure $C_s$ polypeptide is not mixed or otherwise associated with proteins, such as other C proteins, that migrate at a similar position in an SDS-acrylamide gel. A preparation of a substantially pure $C_s$ polypeptide is also substantially free of an antibody or any other compound that binds to a $C_s$ polypeptide.

In the case of polypeptide sequences that are less than 100% identical to a reference sequence, the non-identical positions can be conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine. The resulting substituted polypeptide should have some or all of the function of the non-substituted polypeptide. The substitutions are preferably in the second peptide in the full-length $C_s$ polypeptide.

Preferably the preparation is at least 75%, more preferably at least 90%, and most preferably at least 99%, by weight of the $C_s$ polypeptide. Purity can be measured by any appropriate standard method, e.g., column chromatography, polyacrylamide gel electrophoresis, MALDI-TOF mass spectrometry (MS), or HPLC analysis.

The polypeptides of the invention include, but are not limited to, full-length $C_s$ proteins or polypeptides, e.g., a polypeptide having the amino acid sequence of human $C_s$ (SEQ ID NO:34), murine $C_s$, (SEQ ID NO:38), ovine $C_s$ (SEQ ID NO:15), as well as modified forms of these polypeptides wherein the encoded amino terminal methionine is absent, and forms in which the amino terminal methionine is absent and the resulting amino terminal amino acid is acetylated.

Also included in the invention are peptides, e.g., a peptide having the amino acid sequence of SEQ ID NO:1, such as the peptides of SEQ ID NOS:6, 7, 8, 9, 24, 36, 40, 46, and 47. The invention also includes modified forms of these peptides in which the amino terminus is acetylated. Some of these peptides have, or can have, an amino terminal methionine residue.

The invention further includes recombinant polypeptides, natural polypeptides, and synthetic polypeptides, as well as polypeptides which are preproteins or proproteins.

Also included in the invention are modified forms of $C_s$ polypeptides or $C_s$ peptides, e.g., an acetylated or phosphorylated $C_s$ polypeptide or peptide.

The $C_s$ polypeptides of the invention can be expressed fused to another polypeptide, e.g., a marker polypeptide or fusion partner. For example, the polypeptide can be fused to a hexa-histidine tag to facilitate purification of bacterially expressed protein or a hemagglutinin tag to facilitate purification of protein expressed in eukaryotic cells.

By "mature $C_s$" is meant a polypeptide having the sequence of full-length, wild type $C_s$ of a specific animal species, e.g., the ovine $C_s$ polypeptide of SEQ ID NO:15 or human $C_s$ polypeptide of SEQ ID NO:34.

Also within the invention are soluble fusion proteins in which a full-length form of $C_s$ or a portion (e.g., one or more domains) thereof is fused to an unrelated protein or polypeptide (i.e., a fusion partner) to create a fusion protein. The $C_s$ polypeptide may be recombinantly produced, e.g., from expression of an isolated $C_s$ nucleic acid.

In other embodiments, the invention features a substantially pure polypeptide which includes a first portion linked to a second portion, the first portion including a $C_s$ polypeptide and the second portion including a detectable marker.

The invention further features an antibody (e.g., a monoclonal or polyclonal antibody) that specifically binds to a $C_s$ polypeptide. The antibody can be raised against full-length $C_s$ polypeptides, or $C_s$ peptides such as one including an amino acid sequence corresponding to those at the amino terminus of the $C_s$ polypeptide, e.g., peptides including the amino acid sequences of SEQ ID NO: 6, 7, 46, or 47. The antibody can also be raised to an acetylated peptide, e.g., an acetylated peptide including the amino acid sequences of SEQ ID NO: 6, 7, 8, 9, 24, 36, 40, 46, or 47. A $C_s$-specific antibody is useful as a specific marker for detecting testis (germ) cells and so can be used, e.g., to identify tumor tissue as derived from testis cells, e.g., metastasized from the testes.

The invention further includes a pharmaceutical composition comprising, e.g., a $C_s$ polypeptide or peptide or $C_s$ nucleic acid.

In another aspect, the invention includes a method for producing a $C_s$ polypeptide by culturing a host cell containing a $C_s$ nucleic acid molecule under conditions in which the nucleic acid molecule is expressed.

Also included in the invention is a method for detecting a $C_s$ polypeptide in a sample by obtaining a biological sample, contacting the biological sample with an antibody that specifically binds to $C_s$ under conditions that allow the formation of $C_s$-antibody complexes, and detecting the complexes (if any) as an indication of the presence or activity of $C_s$ in the sample.

An antibody that "specifically binds" to an antigen is an antibody that recognizes and binds to a particular antigen, e.g., a $C_s$ polypeptide, but that does not substantially recognize or bind to other molecules or proteins in a sample, e.g., a biological sample, which includes $C_s$.

The invention features a method of identifying a compound that modulates the expression or activity of $C_s$ by comparing the expression or level of activity of $C_s$ in a cell in the presence and absence of a selected compound, wherein a difference in the level of activity in the presence and absence of the selected compound indicates that the selected compound modulates the activity of $C_s$.

In addition, the invention features a method of treating a patient suffering from a disorder associated with aberrant expression or function of $C_s$ (e.g., excessive expression or activity of $C_s$, or insufficient expression or activity of $C_s$) by administering to the patient a compound which modulates the activity or expression of $C_s$ (e.g., inhibits expression or activity of $C_s$ in a patient having excessive expression or activity of $C_s$, or increases the expression or activity in a patient having insufficient $C_s$ expression or activity). Disorders associated with aberrant expression of $C_s$ can include, e.g., fertility disorders as described herein.

The invention also includes a method of diagnosing a disorder associated with aberrant (e.g., decreased) expression or activity of $C_s$ by obtaining a biological sample from a patient and measuring $C_s$ expression in the biological sample. Increased or decreased $C_s$ expression or activity in the biological sample compared to a control indicates that the patient suffers from a disorder associated with aberrant expression or activity of $C_s$.

Another aspect of the invention includes a method of inhibiting fertility by administering to a male in need thereof an effective amount of an antagonist of a $C_s$ polypeptide or an antagonist of a $C_s$ nucleic acid. For example, the invention includes a method of reducing levels of $C_s$, by administering to a male in need thereof an antibody to $C_s$, or an antibody to a $C_s$ peptide. As another example, the invention includes a method of inhibiting fertility by administering to a male in need thereof an effective amount of an antisense oligonucleotide that inhibits expression of $C_s$. The antisense oligonucleotide is complementary to a nucleic acid sequence encoding Xaa Ser Xaa Xaa Asn Asp (SEQ ID NO:1), e.g., nucleic acid sequences of SEQ ID NOs:16–19, 41, 48, and 49. In other embodiments, the antisense oligonucleotide is complementary to the nucleic acid of SEQ ID NO:37 or SEQ ID NO:39.

The invention also includes a method of reducing levels of $C_s$ by administering to a male in need thereof an enzymatic RNA molecule which specifically cleaves $C_s$ RNA, e.g., in the portion of the nucleic acid sequence encoding SEQ ID NOs: 1, 6, 46, and 47, and others described herein.

In another aspect, the invention includes method of promoting fertility by administering an effective amount of a $C_s$ polypeptide or a biologically active $C_s$ peptide to a male in need thereof.

Also included is a method of promoting sperm motility by administering an effective amount of a $C_s$ polypeptide or a biologically active fragment of a $C_s$ polypeptide to a male in need thereof.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict in terminology, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIGS. 1A and 1B are schematic representations of the predicted amino acid sequence (SEQ ID NO:4) and nucleotide sequence (SEQ ID NO:5), respectively, of human Cα1 polypeptide and Cα gene. The "/" indicates the beginning of exon 2 in the nucleic acid sequence and the encoded amino acids beginning with exon 2 in the predicted amino acid sequence. The nucleic acid sequence beginning with exon 2 and ending at 1133 is SEQ ID NO:3, and the amino acid sequence beginning after the "/" is SEQ ID NO:2.

FIGS. 2A to 2C are separate sheets of a schematic representation of the nucleotide (SEQ ID NO:14) and predicted amino acid sequence (SEQ ID NO:15) of ovine $C_s$.

FIG. 3 is a schematic representation of a partial nucleotide sequence (SEQ ID NO:42) and predicted partial amino acid sequence (SEQ ID NO:43) of a human $C_s$ cDNA.

FIGS. 4A and 4B are schematic representations of a predicted full length human $C_s$ cDNA (SEQ ID NO:35) and its predicted amino acid sequence (SEQ ID NO:34).

FIG. 5 is a schematic representation of a partial nucleotide sequence (SEQ ID NO:44) and predicted partial amino acid sequence (SEQ ID NO:45) of a mouse $C_s$ cDNA.

FIGS. 6A to 6D are separate sheets of a schematic representation of a predicted full length mouse $C_s$ cDNA (SEQ ID NO:39) and its predicted amino acid sequence (SEQ ID NO:38). The nucleotides and amino acids unique to $C_s$ (compared to Cα1) are highlighted.

FIG. 7A is a schematic comparison of the nucleotide sequences of murine, ovine, and human $C_s$ exon 1s (nucleotides −29 to +22).

FIG. 7B is a schematic comparison of the amino acid sequences of murine, ovine, and human $C_s$ exon 1s (amino acids 1 to 7).

DETAILED DESCRIPTION

The present invention provides $C_s$ polypeptides and nucleic acids encoding $C_s$. $C_s$ was originally identified in purified preparations of ovine sperm. Ovine sperm $C_s$ was purified and found by mass spectrometry (MS) to be ~890 Da smaller than Cα1, the predominant somatic isoform. Partial internal amino acid sequence from ovine sperm $C_s$ was an exact match to that of bovine Cα1, but differed from the predicted sequences for the Cβ and Cγ isoforms. Mass spectrometry analysis of the fragments of $C_s$ polypeptide resulting from cleavage by 2-nitro-5-thiocyanatobenzoic (NTCB) showed that the mass difference between $C_s$ and Cα1 originated in the amino-terminal region. A unique blocked amino-terminal fragment was isolated from $C_s$ and sequenced by a combination of tandem mass spectrometry and Edman degradation of a subfragment.

The results revealed that the N-terminal myristate and first 14 amino acids of Cα1 are replaced by an N-terminal acetate and six different amino acids in $C_s$. The predicted mass difference due to these changes is 899 Da. The region of homology between $C_s$ and Cα1 begins at the exon 1/exon 2 boundary in Cα1, which indicates that $C_s$ results from use of an alternative exon 1 in the Cα gene, i.e., $C_s$ is an alternatively spliced transcript of the Cα gene. The different N-terminus of $C_s$ may be related to a unique requirement for localization of the "free" C subunit within the sperm flagellum.

$C_s$ polypeptides are found in various mammals, but only in testis tissue.

$C_s$ Nucleic Acids, and Vectors and Cells Containing $C_s$ Nucleic Acids

The new $C_s$ nucleic acid molecules can be cDNA, genomic DNA, synthetic DNA, or RNA, and can be double-stranded or single-stranded (i.e., either sense or antisense strands). Fragments of these molecules are also considered within the scope of the invention, and can be produced, for example, by the polymerase chain reaction (PCR), generated by treatment with one or more restriction endonucleases, or synthesized by standard techniques. A ribonucleic acid (RNA) molecule can be produced by in vitro transcription.

The nucleic acid molecules of the invention can contain naturally occurring sequences, or sequences that differ from those that occur naturally, but, due to the degeneracy of the genetic code, encode the same polypeptide. In addition, these nucleic acid molecules are not limited to sequences that encode only polypeptides, and thus, can include some or all of the non-coding sequences that lie upstream or downstream from a coding sequence.

The new nucleic acid molecules can be synthesized (for example, by phosphoramidite-based synthesis) or obtained from a biological cell, such as the cell of a mammal. Thus, the nucleic acids can be those of a human, mouse, rat, guinea pig, cow, sheep, horse, pig, rabbit, monkey, dog, or cat, or other wild or domesticated animals. Combinations or modifications of the nucleotides within these types of nucleic acids are also encompassed.

In the event the new nucleic acid molecules encode or act as antisense molecules, they can be used, for example, to regulate translation of $C_s$ mRNA.

The invention also encompasses nucleic acid molecules that hybridize under stringent conditions to a nucleic acid molecule encoding the first peptide (e.g., SEQ ID NO:1) of a $C_s$ polypeptide. The cDNA sequences described herein can be used to identify these nucleic acids, which include, for example, nucleic acids that encode homologous $C_s$ polypeptides in other species. Accordingly, the invention features methods of detecting and isolating these nucleic acid molecules. Using these methods, a sample (for example, a nucleic acid library, such as a cDNA or genomic library) is contacted (or "screened") with a $C_s$-specific probe (for example, a nucleic acid fragment encoding SEQ ID NO:1, SEQ ID NO:6, SEQ ID NO:7, SEQ ID NO:37, SEQ ID NO:41, SEQ ID NO:48, or SEQ ID NO:49, that is at least 15 nucleotides long). The probe will hybridize under stringent conditions to nucleic acids encoding related polypeptides (or to complementary sequences thereof).

The probe, which can contain at least 15 nucleotides, can be produced using any of several standard methods (see, for example, Ausubel et al., "Current Protocols in Molecular Biology, Vol. I," Green Publishing Associates, Inc., and John Wiley & Sons, Inc., NY, 1989). For example, the probe can be generated using PCR amplification methods in which oligonucleotide primers are used to amplify a $C_s$-specific nucleic acid sequence that can be used as a probe to screen a nucleic acid library and thereby detect nucleic acid molecules (within the library) that hybridize to the probe.

One single-stranded nucleic acid is said to hybridize to another if a duplex forms between them. This occurs when one nucleic acid contains a sequence that is the reverse and complement of the other (this same arrangement gives rise to the natural interaction between the sense and antisense strands of DNA in the genome and underlies the configuration of the "double helix"). Complete complementarity between the hybridizing regions is not required for a duplex to form; it is only necessary that the number of paired bases is sufficient to maintain the duplex under the hybridization conditions used.

Typically, hybridization conditions are of low to moderate stringency. Stringent conditions are described in the Summary of the Invention above. These conditions favor specific interactions between completely complementary sequences, but allow some non-specific interaction between less than perfectly matched sequences to occur as well. After hybridization, the nucleic acids can be "washed" under moderate or high stringency conditions to dissociate duplexes that are bound together by some non-specific interaction (the nucleic acids that form these duplexes are thus not completely complementary).

Once detected, the nucleic acid molecules can be isolated by any of a number of standard techniques (see, for example, Sambrook et al., "Molecular Cloning, A Laboratory Manual," 2nd Ed. Cold Spring Harbor Laboratory Press, Cold Spring Harbor, N.Y., 1989).

The invention also encompasses: (a) expression vectors that contain any of the foregoing $C_s$-related coding sequences and/or their complements (that is, "antisense" sequences); (b) expression vectors that contain any of the foregoing $C_s$-related coding sequences operatively associated with a regulatory element (examples of which are given below) that directs the expression of the coding sequences; (c) expression vectors containing, in addition to sequences encoding a $C_s$ polypeptide, nucleic acid sequences that are unrelated to nucleic acid sequences encoding $C_s$, such as molecules encoding a reporter or marker; and (d) genetically engineered host cells that contain any of the foregoing expression vectors and thereby express the nucleic acid molecules of the invention in the host cell.

Recombinant nucleic acid molecules can contain a sequence encoding a soluble $C_s$ polypeptide, mature $C_s$, or $C_s$ including a trafficking sequence, e.g., a signal sequence that allows for secretion of the $C_s$ polypeptide. The full length $C_s$ polypeptide, a domain of $C_s$, or a fragment such as the acetylated amino terminal domain found in $C_s$ but not Cα1, may be fused to additional polypeptides, as described below. Similarly, the nucleic acid molecules of the invention can encode the mature form of $C_s$ or a form that encodes a polypeptide which facilitates uptake by cells or secretion. In the latter instance, the polypeptide is typically referred to as a preprotein, which can be converted into an active form by removal of the signal sequence, for example, within the host cell. Preproteins can be converted into the active form of the protein by removal of the inactivating sequence.

The regulatory elements referred to above include, but are not limited to, inducible and non-inducible promoters, enhancers, operators and other elements, which are known to those skilled in the art, and which drive or otherwise regulate gene expression. Such regulatory elements include, but are not limited to, the cytomegalovirus (hCMV) immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

Similarly, the nucleic acid can form part of a hybrid gene encoding additional polypeptide sequences, for example, sequences that function as a marker or reporter. Examples of marker or reporter genes include β-lactamase, chloramphenicol acetyltransferase (CAT), adenosine deaminase (ADA), aminoglycoside phosphotransferase ($neo^r$, $G418^r$), dihydrofolate reductase (DHFR), hygromycin-B-phosphotransferase (HPH), thymidine kinase (TK), lacZ (encoding β-galactosidase), green fluorescent protein (GFP), and xanthine guanine phosphoribosyltransferase (XGPRT). As with many of the standard procedures associated with the practice of the invention, skilled artisans will be aware of additional useful reagents, for example, of additional sequences that can serve the function of a marker or reporter. Generally, the hybrid polypeptide will include a first portion and a second portion; the first portion being a $C_s$ polypeptide and the second portion being, for example, the reporter described above or an immunoglobulin constant region.

The expression systems that may be used for purposes of the invention include, but are not limited to, microorganisms such as bacteria (for example, E. coli and B. subtilis) transformed with recombinant bacteriophage DNA, plasmid DNA, or cosmid DNA expression vectors containing the nucleic acid molecules of the invention; yeast (for example, Saccharomyces and Pichia) transformed with recombinant yeast expression vectors containing the nucleic acid molecules of the invention (preferably containing the nucleic acid sequence encoding $C_s$ (SEQ ID NO:6 or SEQ ID NO:7); insect cell systems infected with recombinant virus expression vectors (for example, baculovirus) containing the nucleic acid molecules of the invention; plant cell systems infected with recombinant virus expression vectors (for example, cauliflower mosaic virus (CaMV) and tobacco mosaic virus (TMV)) or transformed with recombinant plasmid expression vectors (for example, Ti plasmid) containing $C_s$ nucleotide sequences; or mammalian cell systems (for example, COS, CHO, BHK, 293, VERO, HeLa, MDCK, WI38, and NIH 3T3 cells) harboring recombinant expression constructs containing promoters derived from the genome of mammalian cells (for example, the metallothionein promoter) or from mammalian viruses (for example, the adenovirus late promoter and the vaccinia virus 7.5K promoter).

In bacterial systems, a number of expression vectors may be advantageously selected depending upon the use intended for the gene product being expressed. For example, when a large quantity of such a protein is to be produced, e.g., for the generation of pharmaceutical compositions containing $C_s$ polypeptides or for raising antibodies to those polypeptides, vectors that are capable of directing the expression of high levels of fusion protein products that are readily purified may be desirable. Such vectors include, but are not limited to, the *E. coli* expression vector pUR278 (Ruther et al., *EMBO J.*, 2:1791, 1983), in which the coding sequence of the insert may be ligated individually into the vector in frame with the lacZ coding region so that a fusion protein is produced; pIN vectors (Inouye and Inouye, *Nucleic Acids Res.*, 13:3101–3109, 1985; Van Heeke and Schuster, *J. Biol. Chem.*, 264:5503–5509, 1989); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhidrosis virus (AcNPV) can be used as a vector to express foreign genes. The virus grows in *Spodoptera frugiperda* cells. The coding sequence of the insert may be cloned individually into non-essential regions (for example the polyhedrin gene) of the virus and placed under control of an AcNPV promoter (for example the polyhedrin promoter). Successful insertion of the coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (for example, see Smith et al., *J. Virol.*, 46:584, 1983; Smith, U.S. Pat. No. 4,215,051).

In mammalian host cells, a number of viral-based expression systems may be utilized. In cases where an adenovirus is used as an expression vector, the nucleic acid molecule of the invention may be ligated to an adenovirus transcription/translation control complex, for example, the late promoter and tripartite leader sequence. This chimeric gene may then be inserted in the adenovirus genome by in vitro or in vivo recombination. Insertion in a non-essential region of the viral genome (for example, region E1 or E3) will result in a recombinant virus that is viable and capable of expressing a $C_s$ gene product in infected hosts (for example, see Logan and Shenk, *Proc. Natl. Acad. Sci. USA*, 81:3655–3659, 1984). Specific initiation signals may also be required for efficient translation of inserted nucleic acid molecules. These signals include the ATG initiation codon and adjacent sequences.

In cases where an entire gene or CDNA, including its own initiation codon and adjacent sequences, is inserted into the appropriate expression vector, no additional translational control signals may be needed. However, in cases where only a portion of the coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.*, 153:516–544, 1987).

In addition, a host cell strain may be chosen that modulates the expression of the inserted sequences, or modifies and processes the gene product in the specific fashion desired. Such modifications (for example, glycosylation) and processing (for example, cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used.

For long-term, high-yield production of recombinant proteins, stable expression is preferred. For example, cell lines which stably express the $C_s$ sequences described above may be engineered. Rather than using expression vectors which contain viral origins of replication, host cells can be transformed with DNA controlled by appropriate expression control elements (for example, promoter, enhancer sequences, transcription terminators, and polyadenylation sites), and a selectable marker. Following the introduction of the foreign DNA, engineered cells may be allowed to grow for 1–2 days in an enriched media, and then switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express $C_s$. Such engineered cell lines may be particularly useful in screening and evaluation of compounds that affect the endogenous activity of the gene product.

A number of selection systems can be used. For example, the herpes simplex virus thymidine kinase (Wigler, et al., *Cell*, 11:223, 1977), hypoxanthine-guanine phosphoribosyltransferase (Szybalska and Szybalski, *Proc. Natl. Acad. Sci. USA*, 48:2026, 1962), and adenine phosphoribosyltransferase (Lowy, et al., *Cell*, 22:817, 1980) genes can be employed in tk$^-$, hgprt$^-$ or aprt$^-$ cells, respectively. Also, anti-metabolite resistance can be used as the basis of selection for the following genes: dhfr, which confers resistance to methotrexate (Wigler et al., *Proc. Natl. Acad. Sci. USA*, 77:3567, 1980; O'Hare et al., *Proc. Natl. Acad. Sci. USA*, 78:1527, 1981); gpt, which confers resistance to mycophenolic acid (Mulligan and Berg, *Proc. Natl. Acad. Sci. USA*, 78:2072, 1981); neo, which confers resistance to the aminoglycoside G-418 (Colberre-Garapin et al., *J. Mol. Biol.*, 150:1, 1981); and hygro, which confers resistance to hygromycin (Santerre et al., *Gene*, 30:147, 1984).

Alternatively, any fusion protein may be readily purified by utilizing an antibody specific for the fusion protein being expressed. For example, a system described by Janknecht et al. allows for the ready purification of nondenatured fusion proteins expressed in human cell lines (*Proc. Natl. Acad. Sci. USA*, 88:8972–8976, 1991). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto Ni$^{2+}$. nitriloacetic acid-agarose columns and histidine-tagged proteins are selectively eluted with imidazole-containing buffers.

$C_s$ nucleic acid molecules are useful for diagnosis of disorders associated with aberrant expression of $C_s$. $C_s$ nucleic acid molecules are also useful in genetic mapping and chromosome identification.

$C_s$ Polypeptides

The $C_s$ polypeptides described herein are those encoded by any of the nucleic acid molecules described herein and include $C_s$ peptides, mutants, truncated forms, and fusion proteins. These polypeptides can be prepared for a variety of uses, including, but not limited to, the generation of antibodies, as reagents in diagnostic assays, for the identification of other cellular gene products or compounds that can modulate the activity or expression of $C_s$, for the identification of substrates on which the $C_s$ protein acts, and as pharmaceutical reagents useful for the treatment of disorders associated with aberrant expression or activity of naturally occurring $C_s$ protein. These disorders include male fertility disorders such as azoospermia, necrospermia, oligozoospermia, asthenozoospermia, teratozoospermia, oligoasthenospermia, oligoasthenoteratozoospermia, globozoospermia, immotile cilia syndrome, primary ciliary dyskinesia, ideopathic infertility, and others.

$C_s$ polypeptides can include substantially pure $C_s$ polypeptides, including those that correspond to the polypeptide with an intact signal sequence, and $C_s$ that are soluble or insoluble under normal physiological conditions.

The invention also encompasses polypeptides that are functionally equivalent to $C_s$. These polypeptides are equivalent to $C_s$ in that they are capable of carrying out one or more of the functions of $C_s$ protein in a biological system.

Preferred $C_s$ polypeptides have 20%, 40%, 50%, 75%, 80%, or even 90% or 100% or greater of one or more of the biological activities of the full-length, mature wild type human form of $C_s$. Such comparisons are generally based on an assay of biological activity in which equal concentrations of the polypeptides are used and compared. The comparison can also be based on the amount of the polypeptide required to reach 50% of the maximal activity obtainable with wild type $C_s$.

Functionally equivalent polypeptides can be those, for example, that contain additional or substituted amino acid residues. Substitutions may be made on the basis of similarity in polarity, charge, solubility, hydrophobicity, hydrophilicity, and/or the amphipathic nature of the residues involved. Amino acids that are typically considered to provide a conservative substitution for one another are specified in the summary of the invention.

Polypeptides that are functionally equivalent to $C_s$ polypeptides can be made using random mutagenesis techniques well known to those skilled in the art (and the resulting mutant $C_s$ polypeptides can be tested for activity). It is more likely, however, that such polypeptides will be generated by site-directed mutagenesis (again using techniques well known to those skilled in the art). These polypeptides may have increased or decreased functionality.

To design functionally equivalent polypeptides, it is useful to distinguish between conserved positions and variable positions. This can be done, e.g., by aligning the sequence of $C_s$ cDNAs obtained from various organisms. It is preferable that conserved residues are not altered.

Mutations within the $C_s$ coding sequence can be made to generate variant $C_s$ genes that are better suited for expression in a selected host cell.

The polypeptides of the invention can be expressed fused to another polypeptide, for example, a marker polypeptide or fusion partner. For example, the polypeptide can be fused to a hexa-histidine tag to facilitate purification of bacterially expressed protein or a hemagglutinin tag to facilitate purification of protein expressed in eukaryotic cells.

The polypeptides and peptides of the invention can be chemically synthesized (for example, see Creighton, "Proteins: Structures and Molecular Principles," W. H. Freeman & Co., NY, 1983), or, perhaps more advantageously, produced by recombinant DNA technology as described herein. For additional guidance, skilled artisans may consult Ausubel et al. (supra), Sambrook et al. ("Molecular Cloning, A Laboratory Manual," Cold Spring Harbor Press, Cold Spring Harbor, N.Y., 1989), and, particularly for examples of chemical synthesis Gait, M. J. Ed. ("Oligonucleotide Synthesis," IRL Press, Oxford, 1984).

The invention also features polypeptides that interact with $C_s$ (and the genes that encode them) and thereby alter the function of $C_s$. Interacting polypeptides can be identified using methods known to those skilled in the art. One suitable method is the "two-hybrid system," which detects protein interactions in vivo (Chien et al., *Proc. Natl. Acad. Sci. USA*, 88:9578, 1991), as described in further detail below. A kit for practicing this method is available from Clontech (Palo Alto, Calif.).

Transgenic Animals $C_s$ polypeptides can also be expressed in transgenic animals. These animals represent a model system for the study of disorders that are caused by or exacerbated by overexpression or underexpression of $C_s$, and for the development of therapeutic agents that modulate the expression or activity of $C_s$.

Transgenic animals can be farm animals (pigs, goats, sheep, cows, horses, rabbits, and the like) rodents (such as rats, guinea pigs, and mice), non-human primates (for example, baboons, monkeys, and chimpanzees), and domestic animals (for example, dogs and cats). Transgenic mice are especially preferred for research.

Several techniques known in the art can be used to introduce a $C_s$ transgene into animals to produce the founder lines of transgenic animals. Such techniques include, but are not limited to, pronuclear microinjection (U.S. Pat. No.

4,873,191); retrovirus mediated gene transfer into germ lines (Van der Putten et al., *Proc. Natl. Acad. Sci., USA*, 82:6148, 1985); gene targeting into embryonic stem cells (Thompson et al., *Cell*, 56:313, 1989); and electroporation of embryos (Lo, *Mol. Cell. Biol.*, 3:1803, 1983).

The present invention provides for transgenic animals that carry a $C_s$ transgene in all their cells, as well as animals that carry a transgene in some, but not all of their cells. That is, the invention provides for mosaic animals. Mosaic animals can include those in which a $C_s$ transgene is present in only the germ cells, e.g., sperm cells, or cells from which sperm cells are derived. The transgene can be integrated as a single transgene or in concatamers, e.g., head-to-head tandems or head-to-tail tandems. The transgene can also be selectively introduced into and activated in a particular cell type (Lasko et al., *Proc. Natl. Acad. Sci. USA*, 89:6232, 1992). The regulatory sequences required for such a cell-type specific activation will depend upon the particular cell type of interest, and will be apparent to those of skill in the art.

When it is desired that the $C_s$ transgene be integrated into the chromosomal site of the endogenous $C_s$, gene targeting is preferred. Briefly, when such a technique is to be used, vectors containing some nucleotide sequences homologous to an endogenous $C_s$ gene are designed for the purpose of integrating, via homologous recombination with chromosomal sequences, into and disrupting the function of the nucleotide sequence of the endogenous gene. The transgene also can be selectively introduced into a particular cell type, thus inactivating the endogenous $C_s$ gene in only that cell type (Gu et al., *Science*, 265:103, 1984). The regulatory sequences required for such a cell-type specific inactivation will depend upon the particular cell type of interest, and will be apparent to those of skill in the art. These techniques are useful for preparing "knock out" animals having no functional $C_s$ gene.

Because $C_s$ appears to be expressed specifically in testis cells, disruption of the $C_s$ gene in the exon specific for $C_s$ prevents $C_s$ expression without affecting any critical aspect of mouse development or function except reproduction.

One way to create a mouse $C_s$ knockout is to disrupt the $C_s$ specific exon in mouse embryonic stem (ES) cells by means of a gene replacement vector containing both positive and negative selection markers, and then to introduce the genetically modified ES cells into mouse embryos by blastocyst injection. The resulting chimeric mice are then backcrossed to wild-type animals to obtain a mouse in which the germ cells are derived from the modified ES line.

A probe derived from the ovine $C_s$ specific exon is used to screen a mouse genomic library for a genomic DNA clone containing a $C_s$-specific exon. The genomic clone is mapped with regard to restriction sites and sequenced. The clone is also checked to ensure that it does not contain the alternate exon 1 used in the $C\alpha1$ isoform.

A gene replacement vector is then constructed by inserting a positive marker (neomycin cassette) in the $C_s$ exon coding sequence. A negative selection marker (the herpes simplex thymidine cassette) is inserted at one or both ends of the mouse genomic sequence.

The vector is introduced into ES cells by electroporation, and the cells are grown under positive and negative conditions using G418, an antibiotic to which resistance is conferred by the neomycin gene, and FIAU, a nucleoside analog recognized by the viral thymidine kinase but not the cellular enzyme, respectively. Clones of ES cells that have undergone proper homologous recombination at the $C_s$ exon are identified by a PCR-based assay using one primer specific for the neomycin gene and a second primer specific for mouse genomic sequence just outside of the region inserted into the targeting vector.

The ES cells are injected into blastocyst-stage embryos, which are then surgically implanted into the uterus of pseudopregnant mice. These mice will give rise to chimeric mice. The chimeras are then bred to wild-type mice to produce F1 heterozygotes carrying the disrupted $C_s$ exon ($\Delta C_s$).

Once transgenic animals have been generated, the expression of the recombinant $C_s$ gene can be assayed utilizing standard techniques. Initial screening may be accomplished by Southern blot analysis or PCR techniques to determine whether integration of the transgene has taken place. The level of mRNA expression of the transgene in the tissues of the transgenic animals can also be assessed using techniques which include, but are not limited to, Northern blot analysis of tissue samples obtained from the animal, in situ hybridization analysis, and RT-PCR. Samples of $C_s$ gene-expressing tissue can also be evaluated immunocytochemically using antibodies specific for the $C_s$ transgene product.

For a review of techniques that can be used to generate and assess transgenic animals, skilled artisans can consult Gordon (*Intl. Rev. Cytol.*, 115:171–229, 1989), and may obtain additional guidance from, for example: Hogan et al. "Manipulating the Mouse Embryo" (Cold Spring Harbor Press, Cold Spring Harbor, N.Y., 1986; Krimpenfort et al., *Bio/Technology*, 9:86, 1991; Palmiter et al., *Cell*, 41:343, 1985; Kraemer et al., "Genetic Manipulation of the Early Mammalian Embryo," Cold Spring Harbor Press, Cold Spring Harbor, N.Y., 1985; Hammer et al., *Nature*, 315:680, 1985; Purcel et al., *Science*, 244:1281, 1986; Wagner et al., U.S. Pat. No. 5,175,385; and Krimpenfort et al., U.S. Pat. No. 5,175,384.

Anti-$C_s$ Antibodies $C_s$ polypeptides and peptides, such as an acetylated peptide corresponding to the first exon of the ovine or human (or other species) $C_s$ gene (or immunogenic fragments or analogs) can be used to raise antibodies; such polypeptides and peptides can be produced by recombinant techniques or synthesized as described above (see, for example, "Solid Phase Peptide Synthesis," supra; Ausubel et al., supra). In general, the peptides can be coupled to a carrier protein, such as keyhole limpet hemocyanin (KLH), as described in Ausubel et al., supra, mixed with an adjuvant, and injected into a host mammal. Antibodies can be purified by peptide antigen affinity chromatography. Certain antibodies that specifically bind to the $C_s$ polypeptide of one animal species can also bind specifically to $C_s$ polypeptides of one or more other animal species.

In particular, various host animals can be immunized by injection with a $C_s$ protein or polypeptide. Host animals include rabbits, chickens, mice, guinea pigs, and rats. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin (KLH), and dinitrophenol. Potentially useful human adjuvants include BCG (bacille Calmette-Guerin) and *Corynebacterium parvum*.

Antibodies within the invention therefore include polyclonal and monoclonal antibodies, humanized or chimeric antibodies, single chain antibodies, Fab fragments, F(ab')$_2$ fragments, and molecules produced using a Fab expression library.

Polyclonal antibodies are heterogeneous populations of antibody molecules that are contained in the sera of the immunized animals. Monoclonal antibodies are homogeneous populations of antibodies to a particular antigen, and can be prepared using the $C_s$ polypeptides described above and standard hybridoma technology (see, for example, Kohler et al., *Nature*, 256:495, 1975; Kohler et al., *Eur. J. Immunol.*, 6:511, 1976; Kohler et al., *Eur. J. Immunol.*, 6:292, 1976; Hammerling et al., "Monoclonal Antibodies and T Cell Hybridomas," Elsevier, N.Y., 1981; Ausubel et al., supra).

In particular, monoclonal antibodies can be obtained by any technique that provides for the production of antibody molecules by continuous cell lines in culture such as described in Kohler et al., *Nature*, 256:495 1975, and U.S. Pat. No. 4,376,110; the human B-cell hybridoma technique (Kosbor et al., *Immunology Today*, 4:72, 1983; Cole et al., *Proc. Natl. Acad. Sci. USA*, 80:2026, 1983), and the EBV-hybridoma technique (Cole et al., "Monoclonal Antibodies and Cancer Therapy," Alan R. Liss, Inc., pp. 77–96, 1983). Such antibodies can be of any immunoglobulin class including IgG, IgM, IgE, IgA, IgD and any subclass thereof.

The hybridoma producing the mAb of this invention may be cultivated in vitro or in vivo. The ability to produce high titers of mAbs in vivo makes this a particularly useful method of production.

Once produced, polyclonal or monoclonal antibodies are tested for specific $C_s$ recognition by Western blot or immunoprecipitation analysis by standard methods, e.g., as described in Ausubel et al., supra. Antibodies that specifically recognize and bind to $C_s$ polypeptides are useful in the invention. For example, such antibodies can be used in an immunoassay to monitor the level of $C_s$ produced by a mammal (for example, to determine the amount or subcellular location of $C_s$). Furthermore, such antibodies can be used to detect male testis, e.g., germ, cells in other parts of the body, such as the lymph nodes, to determine whether a cancer, such as a testicular cancer, has metastasized.

Antibodies of the invention are produced using the full length $C_s$ protein, or polypeptide fragments including the unique N-terminal end of the $C_s$ protein. In one specific example, such fragments are generated by standard techniques of PCR, and are then cloned into the pGEX expression vector (Ausubel et al., supra). Fusion proteins are expressed in *E. coli* and purified using a glutathione agarose affinity matrix as described in Ausubel, et al., supra.

In some cases it may be desirable to minimize the potential problems of low affinity or specificity of antisera. In such circumstances, two or three fusions can be generated for each protein, and each fusion can be injected into at least two rabbits. Antisera can be raised by injections in a series, preferably including at least three booster injections.

Antisera are also checked for their ability to immunoprecipitate recombinant $C_s$ proteins or control proteins, such as glucocorticoid receptor, CAT, or luciferase.

The antibodies can be used, for example, in the detection of the $C_s$ in a biological sample as part of a diagnostic assay. Antibodies also can be used in a screening assay to measure the effect of a candidate compound on expression or localization of $C_s$. Additionally, such antibodies can be used in conjunction with the gene therapy techniques need to, for example, evaluate the normal and/or engineered $C_s$-expressing cells prior to their introduction into a patient. Such antibodies additionally can be used therapeutically in a method for inhibiting male fertility or treating abnormal $C_s$ activity.

In addition, techniques developed for the production of "chimeric antibodies" (Morrison et al., *Proc. Natl. Acad. Sci. USA*, 81:6851, 1984; Neuberger et al., *Nature*, 312:604, 1984; Takeda et al., *Nature*, 314:452, 1984) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. Nos. 4,946,778, 4,946,778, and 4,704,692) can be adapted to produce single chain antibodies against a $C_s$ protein or polypeptide. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments include but are not limited to F(ab')$_2$ fragments that can be produced by pepsin digestion of the antibody molecule, and Fab fragments that can be generated by reducing the disulfide bridges of F(ab')$_2$ fragments. Alternatively, Fab expression libraries can be constructed (Huse et al., *Science*, 246:1275, 1989) to allow rapid and easy identification of monoclonal Fab fragments with the desired specificity.

Antibodies to $C_s$ can, in turn, be used to generate anti-idiotype antibodies that resemble a portion of $C_s$ using techniques well known to those skilled in the art (see, e.g., Greenspan et al., *FASEB J.*, 7:437, 1993; Nissinoff, *J. Immunol.*, 147:2429, 1991). For example, antibodies that bind to $C_s$ and competitively inhibit the binding of a binding partner of $C_s$ can be used to generate anti-idiotype antibodies that resemble a binding partner binding domain of $C_s$ and, therefore, bind to and neutralize a binding partner of $C_s$. Such neutralizing anti-idiotype antibodies or Fab fragments of such anti-idiotype antibodies can be used in therapeutic regimens.

Antibodies can be humanized by methods known in the art. For example, monoclonal antibodies with a desired binding specificity can be commercially humanized (Scotgene, Scotland; Oxford Molecular, Palo Alto, Calif.). Fully human antibodies, such as those expressed in transgenic animals are also features of the invention (Green et al., *Nature Genetics*, 7:13–21, 1994; see also U.S. Pat. Nos. 5,545,806 and 5,569,825, both of which are hereby incorporated by reference).

The methods described herein in which anti-$C_s$ antibodies are employed may be performed, for example, by utilizing pre-packaged diagnostic kits comprising at least one specific $C_s$ nucleotide sequence or antibody reagent described herein, which may be conveniently used, for example, in clinical settings, to diagnose patients exhibiting symptoms of the disorders described below.

Antisense Nucleic Acids

Treatment regimes based on an "antisense" approach involve the design of oligonucleotides (either DNA or RNA) that are complementary to $C_s$ mRNA. These oligonucleotides bind to the complementary $C_s$ mRNA transcripts and prevent translation. Absolute complementarity, although preferred, is not required. A sequence "complementary" to a portion of an RNA, as referred to herein, means a sequence having sufficient complementarily to be able to hybridize with the RNA, forming a stable duplex under normal in vivo conditions; in the case of double-stranded antisense nucleic acids, a single strand of the duplex DNA may be tested, or triplex formation may be assayed. The ability to hybridize will depend on both the degree of complementarily and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides complementary to $C_s$ RNA, e.g., the 5' non-coding region and 3' non-coding regions, the $C_s$ coding sequences (e.g., the oligonucleotides described in Example 8), or oligonucleotides complementary to a sequence spanning either a non-coding region and the coding sequences, can be used, and in particular, the nucleotide sequence encoding the unique N-terminal end of the wild type $C_s$ protein. Alternatively, sequences complementary to the 5' noncoding regions can also be used to inhibit $C_s$ expression. Whether designed to hybridize to the 5' non-coding or coding region of $C_s$ mRNA, antisense nucleic acids should be at least 15 nucleotides in length, and can be oligonucleotides up to 50 nucleotides or more in length. In specific examples, the oligonucleotide is at least 15, 18, 25, or at least 50 nucleotides in length. The oligonucleotides can comprise the complementary sequences in the ovine or human $C_s$-specific exon and can be complementary to the 5'UTR, coding sequences, or nucleotides spanning both the 5'UTR and the coding sequences. For the ovine $C_s$ sequence, antisense oligonucleotides can be made based on the −29 to +22 region shown in FIGS. 2A–C. Antisense oligonucleotides based on the human $C_s$ sequence include oligos that are complementary to nucleotide locations −140 to −118: 5'-CGUGGGGUGGGAGCAGGAAGAGA-3" (SEQ ID NO:50), and complementary to nucleotides −102 to −78: 5'-UCUGUCCCCAGAA-CCCUGCCUGCAG-3' (SEQ ID NO:51).

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein.

Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, and can be single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (as described, e.g., in Letsinger et al., *Proc. Natl. Acad. Sci. USA*, 86:6553, 1989; Lemaitre et al., *Proc. Natl. Acad. Sci. USA*, 84:648, 1987; or PCT Publication No. WO 88/09810), or hybridization-triggered cleavage agents (see, for example, Krol et al., *BioTechniques*, 6:958, 1988), or intercalating agents (see, for example, Zon, *Pharm. Res.*, 5:539, 1988). To this end, the oligonucleotide can be conjugated to another molecule, e.g., a peptide, hybridization triggered cross-linking agent, transport agent, or hybridization-triggered cleavage agent.

The antisense oligonucleotides can include at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethyl-aminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-theouracil, 2-thiouracil, 4-thiouracil, 5-methyluracil, uracil-5-oxyacetic acid methylester, uracil-5-oxyacetic acid (v), 5-methyl-2-thiouracil, 2-(3-amino-3-N-2-carboxypropl) uracil, (acp3)w, and 2,6-diaminopurine.

The antisense oligonucleotides can also include at least one modified sugar moiety selected from the group including, but not limited to, arabinose, 2-fluoroarabinose, xylulose, and hexose.

The antisense oligonucleotides can further include at least one modified phosphate backbone, such as a phosphorothioate, a phosphorodithioate, a phosphoramidothioate, a phosphoramidate, a phosphordiamidate, a methylphosphonate, an alkyl phosphotriester, and a formacetal, or an analog of any of these backbones.

In another alternative form, the antisense oligonucleotides can be α-anomeric oligonucleotides. An α-anomeric oligonucleotide forms specific double-stranded hybrids with complementary RNA in which, contrary to the usual β-units, the strands run parallel to each other (Gautier et al., *Nucl. Acids. Res.*, 15:6625, 1987). The oligonucleotide is a 2'-0-methylribonucleotide (Inoue et al., *Nucl. Acids Res.*, 15:6131, 1987), or a chimeric RNA-DNA analog (Inoue et al., *FEBS Lett.*, 215:327, 1987).

Antisense oligonucleotides of the invention can be synthesized by standard methods known in the art, e.g., by use of an automated DNA synthesizer (such as are commercially available from Biosearch, Applied Biosystems, etc.). As examples, phosphorothioate oligonucleotides can be synthesized by the method of Stein et al. (*Nucl. Acids Res.*, 16:3209, 1988), and methylphosphonate oligonucleotides can be prepared by use of controlled pore glass polymer supports (Sarin et al., *Proc. Natl. Acad. Sci. USA*, 85:7448, 1988).

While antisense nucleotides complementary to the $C_s$ coding region sequence could be used, those complementary to the transcribed untranslated region are most preferred, e.g., the −29 to +1 nucleic acid sequence shown in FIGS. 2A–C.

The antisense molecules should be delivered to cells that express $C_s$ in vivo. A number of methods have been developed for delivering antisense DNA or RNA to cells. For example, antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

Recombinant DNA constructs in which the antisense oligonucleotide is placed under the control of a strong pol III or pol II promoter can be used to transfect target cells in the patient. This will result in the transcription of sufficient amounts of single stranded RNAs that will form complementary base pairs with the endogenous $C_s$ transcripts and thereby prevent translation of the $C_s$ mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA.

Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include, but are not limited to: the SV40 early promoter region (Bernoist et al., *Nature*, 290:304, 1981); the promoter contained in the 3' long terminal repeat of Rous sarcoma virus (Yamamoto et al., *Cell*, 22:787–797, 1988); the herpes thymidine kinase promoter (Wagner et al., *Proc. Natl. Acad. Sci. USA*, 78:1441, 1981); or the regulatory sequences of the metallothionein gene (Brinster et al., *Nature*, 296:39, 1988).

Ribozymes

Ribozyme molecules designed to catalytically cleave $C_s$ mRNA transcripts can be used to prevent translation of $C_s$ mRNA and expression of $C_s$ (for basic ribozyme methodology see, e.g., PCT Publication WO 90/11364; Saraver et al., *Science*, 247:1222, 1990). While various ribozymes that cleave mRNA at site-specific recognition sequences can be used to destroy $C_s$ mRNAs, hammerhead ribozymes are particularly useful. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art (Haseloff et al., *Nature*, 334:585, 1988). There are numerous examples of potential hammerhead ribozyme cleavage sites, e.g, sites within the nucleotide sequence are predicted by the ovine $C_s$ mRNA, such as 5'-AGACUGAGUG-3' (SEQ ID NO:25) (for nucleotides −10 to −1), 5'-UGAGUGAUGG-3' (SEQ ID NO:26)(for nucleotides −6 to +4), and 5'-CGGGUGCUUU-3' (SEQ ID NO:27)(for nucleotides −27 to −18), or sites within the nucleotide sequence of the human $C_s$ mRNA, such as 5'-GGACUGAGUG-3' (SEQ ID NO:52) (nucleotides −10 to −1), 5'-GCCCUGAGAA-3' (SEQ ID NO:53)(nucleotides −22 to −13), and 5'-CUCAUGAGCC-3' (SEQ ID NO:54)(nucleotides −55 to −46). The ribozyme can also be engineered so that the cleavage recognition site is located near the 5' end of the $C_s$ mRNA, e.g., 5'-GUGAUGGCUU-3' (SEQ ID NO:28) in the ovine sequence. This increases efficiency and minimizes the intracellular accumulation of non-functional mRNA transcripts.

The ribozymes of the present invention also include RNA endoribonucleases (hereinafter "Cech-type ribozymes"), such as the one that occurs naturally in *Tetrahymena thermophila* (known as the IVS or L-19 IVS RNA), and which has been extensively described by Cech and his collaborators (Zaug et al., *Science*, 224:574, 1984; Zaug et al., *Science*, 231:470, 1986; Zug et al., *Nature*, 324:429, 1986; PCT Application No. WO 88/04300; and Been et al., *Cell*, 47:207, 1986). The Cech-type ribozymes have an eight base-pair sequence that hybridizes to a target RNA sequence, whereafter cleavage of the target RNA takes place. The invention encompasses those Cech-type ribozymes that target eight base-pair active site sequences present in $C_s$.

As in the antisense approach, the ribozymes can be composed of modified oligonucleotides (e.g., for improved stability, targeting, etc.), and should be delivered to cells which express the $C_s$ in vivo. A preferred method of delivery involves using a DNA construct "encoding" the ribozyme under the control of a strong constitutive pol III or pol II promoter, so that transfected cells will produce sufficient quantities of the ribozyme to destroy endogenous $C_s$ messages and inhibit translation. Because ribozymes, unlike antisense molecules, are catalytic, a lower intracellular concentration is required for efficiency.

Methods of Promoting and Inhibiting Fertility $C_s$-based compounds for promoting or inhibiting fertility can be administered systemically or locally to a male. Systemic administration can be achieved parenterally (e.g., intravenous injection, subcutaneous injection, or by implantation of a sustained release formulation), orally, by inhalation, or transdermally (e.g., iontophoretic patch). Local administration to a male can be achieved by subcutaneous injection, implantation of a sustained release formulation, or transdermal administration at the scrotum.

The dose of the compound varies depending upon the manner of administration and the condition of the male to be treated, and ultimately will be decided by the attending physician or veterinarian. Such amount of compound as determined by the attending physician or veterinarian to promote or inhibit sperm motility is referred to herein as an "effective amount."

While it is possible for the compound to be administered as the pure or substantially pure compound, it may also be presented as a pharmaceutical formulation or preparation. The formulations to be used, for both humans and animals, comprise any of the $C_s$ compounds described herein, together with one or more pharmaceutically acceptable carriers thereof, and optionally other therapeutic ingredients.

The carrier must be physiologically as well as pharmaceutically acceptable and compatible with the active ingredient(s) of the formulation (e.g., capable of stabilizing peptides) and not deleterious to the subject to be treated. The formulation should not include oxidizing agents or other substances known to be incompatible with peptides. For example, highly oxidative conditions can lead to the formation of cysteine sulfoxide and to the oxidation of tryptophane. Consequently, it is important to carefully select the carrier.

The formulations may conveniently be presented in unit dosage form and may be prepared by any of the methods well known in the art of pharmacy. All methods include the step of bringing the active ingredient(s) into association with the carrier which constitutes one or more accessory ingredients.

In general, the formulations for tablets or powders are prepared by uniformly and intimately blending the active ingredient(s) with finely divided solid carriers, and then, if necessary, as in the case of tablets, forming the product into the desired shape and size.

Formulations suitable for parenteral (e.g., intravenous) administration, on the other hand, conveniently comprise sterile aqueous solutions of the active ingredient(s). Preferably, the solutions are isotonic with the blood of the subject to be treated. Such formulations may be conveniently prepared by dissolving solid active ingredient(s) in water to produce an aqueous solution, and rendering said solution sterile. The formulation may be presented in unit or multi-dose containers, for example, sealed ampoules or vials.

Formulations suitable for sustained release parenteral administrations (e.g., biodegradable polymer formulations) are also well known in the art. See, e.g., U.S. Pat. Nos. 3,773,919 and 4,767,628 and PCT Publication No. WO 94/15587.

The compounds may also be administered with other compounds capable of stimulating or inhibiting fertility. Examples of spermatogenesis stimulating agents include follicle stimulating hormone (FSH), testosterone, and agonists thereof. Examples of spermatogenesis inhibitory agents include luteinizing hormone-releasing hormone, androgen inhibitors, ethane dimethanesulfonate, and flutamide.

Proteins which form pores in the plasma membrane may additionally be used to permeabilize sperm membranes. These proteins include pore-forming toxins such as those described in Bhakidi et al., Med. Microbol. 182:167–75, 1993, or Fernandez et al., Nature Biotech. 16:418, 1998. The poreforming toxins can be used to deliver $C_s$ polypeptides or nucleic acids encoding $C_s$ polypeptides into a cell in this method, or in any other method described herein requiring the presence of a $C_s$ polypeptide or a nucleic acid encoding a $C_s$ polypeptide.

In addition, $C_s$-based compounds also can be administered to cells by fusing the compounds in-frame to a membrane translocation or nuclear localization signaling protein, e.g., the HIV-1 Trans-Activating (TAT) protein, which can enter cells by passing directly through the lipid bilayer component of the cell membrane. Because such a fusion protein can pass directly through the plasma membrane, it will be able to cross the blood-testis barrier. Such fusion compounds can be delivered in their native form, or in denatured form, in which case they will renature once in side the cell. See, e.g., Strauss, *Science*, 285:14661467, 1999, and Schwarze et al., *Science*, 285:1569–1572, 1999.

Gene therapy techniques, such as chimeraplasty, could also make use of the new $C_s$ nucleic acid sequences. DNA/RNA hybrids that contain a correct sequence of $C_s$ nucleotides can be used to repair point mutations in the $C_s$ gene. See, e.g., Gura, *Science*, 285:316 (1999).

Methods of Promoting and Inhibiting $C_s$-Dependent Cell Division cAMP-dependent protein kinases (PKA) have been implicated in the metaphase-anaphase spindle checkpoint of the cell cycle (Kotani et al., *Mol. Cell*, 1:371–380, 1998). In particular, PKA has been reported to phosphorylate the anaphase promotion complex ("APC"). As long as this complex is phosphorylated at PKA-specific sites, the cell cannot proceed from metaphase to anaphase. Dephosphorylation of the APC, along with phosphorylation of the APC at other sites, leads to release of the metaphase-to-anaphase spindle checkpoint, allowing the cell to progress through cell division.

Accordingly, administration of $C_s$, or $C_s$ agonists, can be used to inhibit cell division in cells having undesired proliferation, e.g., in neoplastic cells such as seminoma cells. Preferably, the $C_s$ agonists do not also inhibit $C_\alpha$ expression or function.

Structure and Function of Unique $C_s$ Amino-terminal Residues

The facts that $C_s$ is present in a wide range of mammals and has been conserved throughout mammalian evolution suggest that its unique amino-terminus has an important role in the structure, assembly or function of the subunit. $C_s$ is not released from demembranated ovine sperm in the presence of cAMP, indicating that it is attached to structures within the sperm even when activated. It is possible that the unique sequence of $C_s$ is responsible for this behavior. In $C\alpha1$, the exon-la-encoded residues form the first two turns of a long α-helix that extends across the surface of the catalytic core of the enzyme. This helix is anchored to the hydrophobic core by the amino-terminal myristate. In the absence of this myristate, the $C\alpha1$ exon-1a residues are unstructured.

In contrast to the situation in $C\alpha1$, the residues encoded by exon 1s of $C_s$ form a shorter domain, are not predicted to form an α-helix, and most importantly, lack a myristate to serve as an anchor. Therefore, the amino-terminal portion of $C_s$ encoded by exon 1s is likely to be unstructured. A short, structureless version of this domain would expose the catalytic subunit's hydrophobic core and possibly allow $C_s$ to bind to hydrophobic sites within the sperm. Alternatively, a flexible amino-terminal tail might itself bind to a structure within the sperm and tether $C_s$ to that structure. In either case, the attachment of $C_s$ to the sperm tail by non-cAMP-dependent bonds would explain the inability of cAMP to release $C_s$ from demembranated sperm.

Such anchoring of activated $C_s$ in the sperm could have several advantages. First, the phosphorylation of its substrates could be accomplished more efficiently. This would be particularly true in the sperm tail, where most of the proteins, including potential target substrates, are assembled into structures such as the axoneme, mitochondrial sheath, fibrous sheath and outer dense fibers. A protein the size of $C_s$ might not readily diffuse through or around such large and generally dense structures. By positioning the activated catalytic subunit in close proximity to its target substrates, rapid phosphorylation of these proteins upon activation of $C_s$ would be ensured without the need for $C_s$ to diffuse long distances. Conversely, if cAMP levels decreased, $C_s$ would be able to rapidly rebind to R, which itself would be anchored in the same general vicinity by AKAPs.

Finally, by limiting the distance that activated $C_s$ can travel, promiscuous phosphorylation of other flagellar proteins and its potentially deleterious effects would be avoided. This type of spatial arrangement is also observed in other signal transduction complexes, where the components of the signaling pathway are assembled on scaffold proteins for more effective physical interaction between enzyme and substrate, and for enhanced specificity.

AKAPs have been shown to be located specifically in the mitochondrial sheath and the fibrous sheath of the mammalian sperm tail. If the unique amino terminus of $C_s$ has evolved to anchor $C_s$ to these accessory structures, this could account for the absence of $C_s$ in cilia, which lack these structures.

EXAMPLES

The invention will be further described in the following examples, which do not limit the scope of the invention described in the claims.

Example 1

Identification of Ovine $C_s$

To characterize ovine $C_s$(sperm-associated catalytic subunit of cAMP dependent protein kinase), demembranated ram sperm models, which retain more than 90% of protein kinase A activity, were analyzed using protein kinase blots.

Ejaculated sperm were -collected and washed and demembranated as described in San Agustin et al., *Cell Motl. Cytoskel*., 24:264–73, 1993. Samples of demembranated sperm were dissolved in SDS-PAGE sample buffer (10% glycerol, 3% SDS, 0.03% bromphenol blue, 50 mM DTT, 62.5 mM Tris-HCl, pH 6.8), and then electrophoresed in a 1.5-mm thick gradient gel (5–15%, 12×14 cm). Protein kinases were renatured on the blot and incubated in the presence of [γ-$^{32}$P]ATP using a protocol adapted from Ferrell and Martin, *Methods Enzymol.*, 200:430–35, 1991 and described in San Austin et al., *Methods Cell Biol.*, 47:135–40, 1995. Under these condition, bound kinases phosphorylated themselves or the blocking reagent. In some experiments, 1% poly(Glu,Tyr) 4:1, a tyrosine kinase substrate, was used as blocking solution in place of 5% BSA.

Six to eight putative kinase bands were observed in the demembranated sperm. Two prominent bands at ~$M_r$ 40,000 and 39,000 migrated slightly faster than porcine C (41 kDa). To determine if either of these was $C_s$, the incubation with [γ-$^{32}$P]ATP was carried out in the presence of PKI(5–24), a potent inhibitor of C, including ram $C_s$, activity. The inhibitor completely and specifically blocked the labeling of porcine C and the ~$M_r$ 40,000 band from sperm, indicating that the latter is likely to represent $C_s$. Labeling of the other bands was not affected by PKI(5–24).

To confirm that the sperm protein kinase inhibited by PKI(5–24) is the catalytic subunit of PKA, the proteins of demembranated ram sperm were probed in Western blots with a polyclonal antibody against bovine C.

Samples were dissolved in SDS-PAGE sample buffer, electrophoresed in 0.75-mm thick 10% minigels (4.5×8 cm), and blotted to PVDF membranes (TE 22 transfer apparatus, Hofer Scientific, 28 V for 5 minutes followed by 84 V for 20 min). The transfer buffer composition was 50 mM Tris base, 192 mM glycine, 20% methanol, and 0.01% SDS. After transfer, the membrane was blocked with TBS-Tween-20 (30 mM Tris-HCl, pH 7.4, 150 mM NaCl, 0.05% Tween-20) for 20 min, incubated with anti-bovine C (in TBS-Tween-20, 1:200 dilution) for 1 hour, then washed four times (5 minutes each wash) with 200 ml TBS-Tween-20. Incubation with the secondary antibody (alkaline phosphatase-labeled goat anti-rabbit IgG in TBS-Tween-20, 1:800 dilution) was for 1 hour, followed by washing twice, 10 minutes each wash, with 200 ml TBS-Tween-20. Final wash was 200 ml 30 mM Tris-HCl, pH 7.4, 150 mM NaCl, 0.5% Triton X-100 for 20 min. The blot was then exposed to BCIP/NBT (1 tablet dissolved in 10 ml water) to reveal cross-reacting proteins.

The antibody reacted with a single sperm protein that migrated slightly faster than porcine C in the SDS-polyacrylamide gels. This protein could be extracted from sperm flagella by treatment with cAMP in the presence of Triton X-100, in agreement with a previous observation that much of the PKI(5–24)-inhibitable protein kinase activity could be released from sperm by this same treatment (San Agustin et al., Cell Motil. Cytoskel. 27:206–18, 1994). These results provided independent evidence that the ~$M_r$ 40,000 band from sperm is an isoform of C, referred to herein as $C_s$.

Example 2

Identification of $C_s$ as a Tissue-Specific Variant of $C_\alpha$

The unusual mobility of ram $C_s$ could have been due to species (porcine vs. ovine) or tissue (somatic vs. sperm) variation. To clarify the source of the anomalous $C_s$ mobility, ram skeletal muscle C ($C_{sm}$) was partially purified and compared directly to the sperm isoform. Because the predominant isoform of C in skeletal muscle is $C_\alpha$ (Uhler et al., *J. Biol. Chem.*, 261:15360–63, 1986), the isoform purified from muscle is presumed to be predominantly or entirely Cα1.

The PKA catalytic subunit from ovine skeletal muscle ($C_{sm}$) was isolated with a procedure adapted from Okuno and Fujisawa (*Biochim. Biophys. Acta*, 1038:204–08, 1990) for the isolation of bovine heart C. Working at 4° C., about 600 to 800 g of skeletal muscle tissue from the hind legs and back of a ram were stripped of fat and connective tissue and then passed through a meat grinder (coarse setting). The ground tissue was mixed with 1.5 l of homogenization buffer (10 mM potassium phosphate, pH 6.8, 1 mM EDTA, 0.1 mM DTT) and further processed to a smooth consistency in a Waring blender. The homogenized mass was then centrifuged at 18,000×g for 30 minutes and the supernatant was collected, filtered through glass wool, and applied to a packed DE 52 column (5×15 cm) equilibrated with the homogenization buffer.

About 8 l of wash buffer (55 mM potassium phosphate, pH 6.8, 1 mM EDTA, 0.1 mM DTT) were then passed through the column, followed by about 2 l of the DE 52 equilibration buffer (45 mM potassium phosphate, pH 6.8, 0.1 mM EDTA, 1 mM DTT, 0.1% v/v Tween 20). The PKA holoenzyme was bound to the DE 52 resin; $C_{sm}$ was released by washing with DE 52 equilibration buffer containing 100 μM cAMP/DE 52 sequestered cAMP, so that $C_{sm}$ was eluted only after about twice the bed volume of the elution buffer was applied. The fractions containing $C_{sm}$ were identified by SDS-PAGE, and then applied to a CM Fast Flow column (1×8.5 cm, equilibrated with DE 52 equilibration buffer). The column was washed with 20 mM potassium phosphate, pH 6.8, 1 mM EDTA, 50 mM NaCl, 0.1% w/v β-octylglucoside, 1 mM DTT and then subjected to a linear salt gradient of 50 mM to 300 mM NaCl (total volume of gradient, 50 ml; flow rate 0.4 ml/min). $C_{sm}$ eluted between 160 and 280 mM NaCl. The resulting $C_{sm}$ preparation was about 95% pure, with a yield of about 400 μg $C_{sm}$/600 g skeletal muscle. It was made 40% in glycerol and stored at −20° C. Homogeneous $C_{sm}$ was obtained by applying an aliquot of the glycerol-stabilized preparation (2–3 ml, 40–60 μg $C_{sm}$) to a Source 15S column (0.5×5 cm, equilibrated with buffer A) and eluting with a linear NaCl gradient (buffer A plus buffer B, total volume of 7 ml, flow rate 0.4 ml/min). $C_{sm}$ eluted as a sharp peak between 250 and 265 mM.

The skeletal muscle subunit had the same mobility as porcine C, and both migrated slightly slower than the sperm subunit. When purified ram $C_{sm}$ and ram sperm flagella were mixed together, two distinct, nonmerging bands were observed. These results clearly demonstrate that the unusual mobility of $C_s$ is tissue specific.

Example 3

Localization of $C_s$ Within Sperm

The relative distribution of $C_s$ in demembranated sperm, isolated sperm heads, and tails was also investigated.

Demembranated sperm were isolated as described above. Isolated sperm heads were prepared in the same way except that flagella were separated from the demembranation medium by centrifugation through 40% Percoll, and heads were separated from the demembranation medium by centrifugation through 70% Percoll.

The vast majority of $C_s$ was located in the flagella, although some $C_s$ was detectable in the sperm heads. Similar results were obtained with intact sperm heads and intact sperm tails. These results are consistent with previous reports that PKA is located primarily in the sperm flagella.

Example 4

Effect of Epididymal Processing on $C_s$ Mobility

Some sperm proteins undergo processing during epididymal maturation (Dacheux et al., *Biol. Reprod.*, 29:1033–46, 1983; Jones et al., *J. Cell Sci.*, 109:2561–70, (1996; Lakoski et al., *Gamete Res.*, 23:21–37, 1989). To determine if such processing was responsible for the unusual mobility of $C_s$, sperm were isolated from the testis and regions of the epididymis, and the relative mobilities of their PKA catalytic subunits compared in Western blots. $C_s$ from demembranated ram testicular sperm, demembranated epididymal sperm (cauda, corpus and caput), and demembranated ejaculated sperm flagella, and its relative mobility in these tissues compared. The mobility of $C_s$ was identical in sperm from all stages, and in all cases was slightly faster than that of somatic C. These results indicate that the apparently smaller size of $C_s$ is not due to processing during sperm maturation.

Example 5

Purification of Ovine $C_s$

Ovine $C_s$ was removed from purified sperm flagella in a near homogeneous state by a two-step procedure consisting of extraction with Triton X-100 (0.5%, 5 ml per $1.5 \times 10^9$ sperm, 30 minutes) in the presence of 150 mM NaCl to remove the detergent- and salt-soluble proteins, followed by extraction with cAMP (10 $\mu$M, 20 minutes) in the absence of detergent to remove $C_s$.

Extraction was performed at 4° C., and preparations at following various steps in the procedure were examined using SDS-polyacrylamide gel electrophoresis. Sperm flagella (in PBSI) were centrifuged (1750×g, 15 minutes) and resuspended for 30 minutes in a Triton X-100/NaCl buffer (5 mM potassium phosphate, pH 6.5, 0.5% v/v Triton X-100, 150 mM NaCl, 1 mM EDTA, 25 $\mu$M leupeptin, 1 mM DTT), at a concentration of $3 \times 10^8$ flagella /ml. This treatment removed the plasma membrane and most of the soluble flagellar proteins that otherwise would coextract with $C_s$ upon subsequent treatment with cAMP; $C_s$ itself remained bound to the demembranated flagella. Inclusion of 150 mM NaCl in the Triton X-100 extraction of some proteins that otherwise would be removed by the cAMP buffer and thus contaminate the $C_s$.

The suspension was then centrifuged (1750×g, 30 minutes), the supernatant discarded, and the pellet dispersed in KPNELD wash buffer (5 mM potassium phosphate, pH 6.5, 50 mM NaCl, 1 mM EDTA, 25 $\mu$M leupeptin, 1 mM DTT, 0.22 ml buffer/$10^8$ flagella) and centrifuged (1750×g, 10 minutes). This was repeated with 0.167 ml buffer/$10^8$ flagella. The washed pellet was then extracted for 20 minutes with KPNELD +10 $\mu$M cAMP, 0.167 ml/$10^8$ flagella. The cAMP extract, which contained $C_s$, was transferred to a polypropylene tube that had been treated with Triton X-100 to minimize nonspecific binding of $C_s$, and then centrifuged at 27,000×g for 15 minutes to remove residual flagella.

After two washes with buffer, the flagella were exposed to 10 $\mu$M cAMP, which removed nearly pure $C_s$ from the flagella. In some preparations, the cAMP extract also contained small amounts of a 20-kDa protein. This protein apparently was not a proteolytic fragment of $C_s$, as it was not recognized by polyclonal antibodies to C$\alpha$1.

$C_s$ was further purified by passing the cAMP extract through a CM Fast Flow column. This step removed any trace of a 20-kDa protein, which eluted later than $C_s$. Using this procedure, 20–25 $\mu$g of purified $C_s$ was obtained from ~6 ml of semen (~$10^{10}$ sperm).

Example 6

Mass Differences Between $C_s$ and $C_{sm}$

MALDI TOF mass spectrometry (MS) was used to determine if the difference in the electrophoretic mobility of $C_s$ and $C_{sm}$ was due to a difference in their respective masses. MALDI TOF MS was performed on a Perseptive Biosystems linear Voyager BioSpectrometry Workstation. Electrospray MS/MS was performed using a Perkin Elmer Sciex API 365 benchtop triple quadrupole mass spectrometer equipped with MicroIonSpray and the BioToolBox™ software package. Product-ion MS/MS experiments were carried out using nitrogen as the dissociating gas at a collision cell pressure of $2.2 \times 10^{-3}$ Torr and a collision energy of 40 eV. Scans were obtained in the positive-ion mode from m/z 30 to 1500 with a step size of 0.25 amu and a dwell time of 0.75 msec. To increase sensitivity, the first MS was operated using low resolution (full width, half height ~3 amu). Additionally, samples were infused at a flow rate of 200 nl/min using the MicroIonSpray source, thus allowing 140 scans to be signal averaged to improve signal-to-noise ratio The MALDI TOF mass spectra for $C_s$ had a single peak corresponding to a mass of ~39.9 kDa, whereas those for $C_{sm}$ had a single peak of ~40.8 kDa. The spectrum for an equimolar mixture of $C_s$ and $C_{sm}$, revealed two well separated peaks with masses of 39,832 Da and 40,722 Da. Although some error is to be expected for the estimated masses of proteins of this size, the mass difference obtained by comparing two proteins in the same spectrum is quite accurate. Therefore, $C_s$ is ~890 Da smaller than $C_{sm}$, confirming the apparent difference in mass observed by SDS-PAGE. The results also confirm the purity of the $C_s$ and $C_{sm}$ preparations. The observed mass for ovine $C_{sm}$ was reasonably close to that predicted for bovine somatic C$\alpha$1 with a myristylated glycine at the amino-terminus (40,858 Da).

Example 7

$C_s$ is an Isoform Distinct from C$\gamma$

Because of the size and tissue location of $C_s$, it was possible that $C_s$ corresponds to C$\gamma$, which was originally described as a human cDNA isolated from testes mRNA. When expressed and purified from transfected cells c$\gamma$ migrates in SDS-PAGE at 39–40 kDa, which is close to the 41–42 kDa size reported for C$\alpha$1 (Beebe et al., *J. Biol. Chem.* 267:25505–12, 1992). However, unlike $C_s$, C$\gamma$ reportedly is not sensitive to PKI. Moreover, the predicted amino acid sequence of C$\gamma$ differs at 74 amino acid residues from C$\alpha$1. Thus, the ovine homologs of these two isoforms should be distinguished by a comparison of even partial amino acid sequences between the two proteins. Accordingly, $C_s$ was digested with trypsin, and the resulting fragments were sequenced and compared to published sequences for C$\alpha$1 and C$\gamma$. To generate trypsin fragments, $C_s$ was first blotted onto PVDF membrane as described above. The membrane was next cut into small pieces (1×1 mm) and submerged under 50 $\mu$l of Digest Buffer (10% acetonitrile, 1% hydrogenated Triton X-100, 100 mM ammonium bicarbonate, pH 8.2). One $\mu$g of trypsin in 4 $\mu$l of 50 mM acetic acid was added to the sample, which was then incubated overnight at 37° C. followed by direct injection of the supernatant onto the HPLC. Tryptic peptides were separated on a 1 mm×25 cm Applied Biosystems (Aquapore RP-300) $C_8$ column using a linear gradient from 100% solvent A (0.1% TFA) to 55% solvent B (0.08% TFA in acetonitrile/water: 70/30) in 30 minutes, then from 55% solvent B to 85% solvent B in 10 minutes at a flow rate of 150 $\mu$l/min. The eluent was monitored at 210 nm and fractions were collected manually.

A comparison of the sequences of the trypsin fragments revealed that the ovine $C_s$ sequence exactly matched that of the published bovine C$\alpha$1 (78 out of 78 residues). Moreover, in 17 out of 18 positions where human C$\alpha$1 differed from human Cγ, ovine $C_s$ was identical to human Cα1. Therefore, $C_s$ is not Cγ. Similarly, ovine $C_s$ was identical to bovine Cα1 at 5 out of 5 positions where bovine Cα1 differed from bovine Cβ, indicating that $C_s$ is not Cβ. These results strongly suggested that $C_s$ is a short variant of Cα1.

The amino acid sequence of single CNBr-generated fragments of purified ram $C_s$ and $C_{sm}$ was also determined. To generate CNBr-fragments about 2 µg each of $C_{sm}$ and $C_s$ in 50 µl of buffer A was first lyophilized. To each lyophilized sample was added 12.5 µl of 100 mM DTT, and the mixture then was allowed to stand at room temperature for 1 hour. 37.5 µl of 47 mM CNBr (in 88% formic acid) were added to start the cleavage reaction, and the reaction mixture was incubated overnight (about 19 hours) at room temperature in the dark. To stop the reaction, 100 µl of water was added, and the resulting solution was lyophilized to remove the formic acid and unreacted CNBr. The pellet was resuspended in 100 µl of water and lyophilized again. Afterwards, 15 µl of SDS-sample buffer (50 mM Tris-HCl, pH 6.8, 15% glycerol, 5% SDS, 0.003% bromphenol blue) was added to the lyophilized sample. The sample was electrophoresed in a 0.75-mm thick 13% Tris-tricine SDS-polyacrylamide gel (Schägger et al., Methods Enzymol. 126:224–37, 1986); the gel was silver stained to reveal the fragments.

For sequencing of CNBr-generated fragments, the starting sample contained about 10–15 µg of protein. The cleavage products were separated by electrophoresis in a 1.5 mm gel and transferred to a PVDF membrane according to the protocol of Otter et al., Anal. Biochem., 162:370–77, 1987, except that the transfer time was shortened from 17 hours to 12 hours. The blot was stained with amido black and the fragments excised and sequenced.

A CNBr fragment of $C_{sm}$ was found to have a sequence identical to a sequence of bovine Cα1. This result is consistent with the presumption that $C_{sm}$ is the conventional Cα1 isoform.

Example 8

Localization of Amino Acid Sequence Differences Between $C_s$ and $C_\alpha$

To delimit the regions that differ between $C_s$ and $C_{sm}$, the purified proteins were treated with a variety of peptidases, and the resulting digestion products analyzed.

The proteins were first digested with 2-nitro-5 thiocyanatobenzoic (NTCB), which cleaves at cysteinyl residues, using a procedure adopted from Jacobson et al., J. Biol. Chem., 248:6583–91, 1973). The concentration of $C_{sm}$ and $C_s$ (in fresh buffer A) was adjusted to 40 µg/ml and 50 µl of each was then lyophilized. The dried samples were redissolved in 125 µl of denaturation buffer (100 mM HEPES, pH 8.5, 8.1 M urea) and allowed to stand for 30 minutes at room temperature. A 15-µl aliquot of freshly prepared NTCB (66.5 mM) was added and allowed to react for 20 minutes. The amount of NTCB added gave about a tenfold excess of NTCB over the combined sulfhydryl groups of DTT (present in buffer A) and $C_{sm}$ or $C_s$ (presumed to be two, as with bovine Cα1). NTCB (15 mg) was first dissolved in 0.333 ml ethanol and then made up to 1 ml with the denaturation buffer. The pH of the reaction mixture after the addition of NTCB was about 8.4. The cleavage reaction was initiated by the addition of 4.8 µl of 1 N NaOH, which brought the pH up to about 11.6. The reaction was allowed to proceed for about 16 hours. The mixture was then transferred to a Centriplus 10 concentrator (Amicon) and washed with buffer A until the urea and excess NTCB were reduced about 3000 fold and the final volume was reduced to about 200 µl. The concentrate was then mixed with an equal volume of 2×Schägger sample buffer and electrophoresed in a 10% Tris-tricine SDS-polyacrylamide gel (Schägger et al., Methods Enzymol., 126:224–37, 1986)). The fragments were revealed by silver staining.

Preparation of NTCB fragments for mass spectrometry was the same, except that 30 µg each of $C_{sm}$ and $C_s$ were used as starting material. The Tris-tricine gel was transferred to nitrocellulose (Otter et al., Anal. Biochem., 162:370–77, 1987) at 28 V for 5 minutes and then at 84 V for 20 minutes. The bands were revealed by staining with Ponceau S and then cut out for MALDI TOF MS.

Because there are only 2 cysteinyl residues (Cys-199 and Cys-343) out of a total of 350 amino acids in either bovine or human Cα1, three fragments result from a complete cleavage of Cα1 by NTCB. Based on the Cα1 amino acid sequence, these fragments are predicted to have masses of 0.9 kDa (residues 343–350), 16.6 kDa (residues 199–342), and 23.0 kDa (residues 1–198).

Three major bands were observed when the NTCB fragments of $C_s$ and $C_{sm}$ were electrophoresed in a Tristricine SDS-polyacrylamide gel. The largest band corresponded to the intact polypeptide. Based on the predicted sizes of the fragments, fragment 1 corresponded to the amino-terminal fragment, and fragment 2 corresponded to residues 199–342. Fragment 2 from $C_s$ and fragment 2 from $C_{sm}$ had identical mobilities, whereas fragment 1 of $C_s$ migrated more rapidly than fragment 1 of $C_{sm}$.

The fragments were then transferred to nitrocellulose and analyzed by MALDI TOF mass spectrometry. Fragment 2 of $C_s$ and fragment 2 of $C_{sm}$ had nearly identical masses of 17,970 and 17,967 Da, respectively. In contrast, fragment 1 of $C_s$ had a mass of ~23,620 Da, whereas fragment 1 of $C_{sm}$ had a mass of ~24,444 Da, a difference of ~824 Da. Because this difference is similar to the difference in masses between the intact polypeptides (~890 Da), most of the difference in mass must be due to structural differences in the amino-terminal halves of the proteins. When considered with sequence information obtained from the trypsin-cleaved products, much of this part of $C_s$ (residues 29–40, 72–91 and 129–133) already had been found to match the sequence of Cα1. Thus, these regions could be ruled out as being the source of the sequence difference.

A source for the sequence difference between $C_s$ and $C_{sm}$ was next examined by examining products of endoproteinase lysine-C digestions. There are 34 lysyl residues in bovine Cα1, of which 8 occur in the first 59 residues. It therefore seemed likely that digestion of $C_s$ and $C_{sm}$ with endoproteinase lysine-C would allow the detection of any dissimilar fragments.

$C_{sm}$ and $C_s$ were blotted on nitrocellulose, which was then cut into 1×1 mm pieces and submerged under 50 µl of Digest Buffer. An aliquot of endoproteinase lysine-C (0.5 µg in 0.5 µl of 25 mM sodium phosphate, pH 7.5, 1 mM EDTA) was then added and the samples were incubated overnight at 37° C. followed by direct injection of the supernatant onto the HPLC. Endoproteinase lysine-C peptides were separated on a 0.5 mm×150 mm Applied Biosystems column ($C_{18}$, 300 A) using a linear gradient from 100% solvent A to 46% solvent B in 35 minutes, then from 46% solvent B to 60% solvent B in 10 min at a flow rate of 20 µl/min. The eluent was monitored at 210 nm and fractions collected manually.

HPLC chromatograms of endoproteinase lysine-C fragments from $C_s$ and $C_{sm}$ revealed a prominent peak eluting at 26 min in the $C_s$ digest but not in the $C_{sm}$ digest. MALDI TOF MS analysis of this peak indicated that it contained a single peptide with a mass of 1474 Da. Similarly, a peak at 1475 Da was observed in a MALDI TOF mass spectrum of the endoproteinase lysine-C digest of $C_s$, but not in the $C_{sm}$ digest.

An attempt to determine the amino-terminal sequence of the 1474 Da peptide obtained by HPLC was unsuccessful, suggesting that its amino-terminus is blocked. These results indicate that this fragment contains the amino-terminus of $C_s$.

The structure of the 1474 Da peptide was solved by a combination of MS/MS analysis on a triple quadrupole mass spectrometer, and Edman sequence analysis was performed of an endoproteinase aspartate-N cleavage product. This proteinase was chosen because the MS/MS analysis indicated only a single aspartate was present in the sequence.

In product-ion MS/MS, precursor ions (or parent ions) of a particular m/z value are selected in the first quadrupole (Q1) of a triple quadrupole mass spectrometer and allowed to enter the second quadrupole (Q2). The second quadrupole acts as a collision cell and is filled with a neutral gas (in this case nitrogen). The parent ions undergo fragmentation through collisions with this neutral gas, a process called collisionally activated dissociation, or CAD. These product ions (or daughter ions) are then analyzed in the third quadrupole (Q3). For peptide ions, fragmentation specifically at the amide bonds results in a series of ions with charge retention on either the carboxy terminus ("y-ions") or amino terminus ("b-ions"). The sequence of the peptide can be deduced from these, as well as other fragment ions in the daughter ion spectrum.

The doubly charged ion (m/z 738.3) was selected and fragmented. Initial interpretation of the spectrum confirmed an amino-terminally blocked residue (acetyl-AS) and provided much of the carboxy-terminal sequence (DV[K/Q]EF[I/L]AK). Leucine and isoleucine have identical masses and lysine and glutamine have nearly identical masses and so could not be distinguished.

The blocked amino-terminal peptide isolated from the endoproteinase lysine-C digest of $C_s$ was dissolved in 25 μl of 100 mM ammonium bicarbonate, and 0.12 μg of endoproteinase aspartate-N in 3 μl of 10 mM Tris-HCl, pH 7.5 was added. Digestion proceeded overnight at 37° C. The digested peptide was desalted in a $C_{18}$ micro cartridge (0.8 mm×5 mm, LC packing, San Francisco, Calif.) prior to direct application to Edman sequence analysis.

As predicted, a single Edman sequence (DVKEFLAK; SEQ ID NO:29) was obtained. This indicated that the residue following valine was lysine, and confirmed the rest of the carboxy-terminal sequence.

The data were consistent with either glycine-glycine or asparagine on either side of the proline, because glycine-glycine and asparagine have identical masses. To resolve this uncertainty, a series of synthetic peptides were made containing permutations of asparagine and glycine-glycine.

Four peptides were synthesized to compare their MS/MS ion spectra to the MS/MS product ion spectrum of the amino-terminally blocked endoproteinase lysine-C peptide derived from $C_s$: (1) acetyl-SANPNDVQEFLAK (SEQ ID NO:30), (2) acetyl-ASNPNDVKEFLAK (SEQ ID NO:31), (3) acetyl-ASGGPNDVKEFLAK (SEQ ID NO:32), and (4) acetyl-ASNPGGDVKEFLAK (SEQ ID NO:33). Peptides were synthesized on a Perkin Elmer 432A Synergy Peptide Synthesizer using HBTU activation and the FMOC protecting strategy. Crude peptide mixtures were purified by reversed phase HPLC using an Aquapore OD-300 $C_{18}$ column (1×100 mm) and a water/acetonitrile/TFA gradient at 40 μl/min and 37° C.

The tandem mass spectrum of only one of these peptides, acetyl-ASNPNDVKEFLAK (SEQ ID NO:31), was virtually identical to that of the 1474 Da amino-terminal peptide isolated from $C_s$, indicating that this is the correct sequence.

Although the 1474 Da peptide was derived from an endoproteinase lysine-C digest, the appearance of an internal lysine in the fragment is not completely unexpected because this lysine is followed carboxy-terminally by a glutamic acid. It has been suggested that this enzyme may be hindered at glutamic acid residues (Jekel et al., *Anal. Biochem.*, 134:347–54, 1983).

A comparison of this sequence to the amino-terminal portion of bovine Cα1 showed that residues 7–13 of $C_s$ (VKEFLAK; SEQ ID NO:32) are identical to residues 15–21 of Cα1. Residues 1–6 of $C_s$ are completely different from residues 1–14 (SEQ ID NO:33) of Cα1. The homology between $C_s$ and somatic Cα1 begins precisely at the site (Val-15 in Cα1) of the exon 1/exon 2 junction in the mouse Cα gene. The residues carboxyl terminal to this site match exactly the sequence of bovine Cα1. Thus, these results indicate that $C_s$ is a splice variant of Cα1 resulting from the use of an alternate 5' exon.

The calculated mass difference between the amino-terminal sequence of bovine Cα1 (including an amino-terminal myristyl group) and that of $C_s$ (including an amino-terminal acetyl group) is 899.2 Da, in excellent agreement with the difference in mass determined by MALDI TOF MS.

Example 9

Determination of the Ovine $C_s$ Nucleic Acid Sequence

The nucleotide sequence of a $C_s$ cDNA was determined from mRNA prepared from ovine testis. Testis mRNA was isolated using standard procedures (Ausubel et al., 1989), and first-strand cDNA was synthesized using reverse transcriptase and oligo-dT as a primer. cDNA was amplified in a polymerase chain reaction (PCR) using two sets of gene-primers based on the bovine Cα sequence (Wiemann et al., 1992). Sense primers corresponded to nucleotides 7–26 and 947–928, whereas anti-sense primers were complementary to nucleotides 800–782 and 947–928. Primer 7–26 included nucleotides upstream of the exon 1/exon 2 junction and thus was specific for $C_s$. PCR products were ligated into pBluescript II KS (Stratagene), subcloned and sequenced. One of the clones obtained using the $C_s$ specific primer had a 5' sequence (exclusive of the primer) that predicted residues matching Gly-10 to Ser-15 of conventional bovine somatic Cα.

Knowledge of the exact ovine Cα sequence from these clones then made it possible to carry out 5' and 3' RACE reactions to extend the sequence in both directions. ovine testis poly-$A^+$ mRNA was isolated from total RNA using an oligo(dT)-cellulose spin column (Clontech), and double-stranded cDNA synthesized from the poly-$A^+$ mRNA. 5'-RACE reactions were carried out using a gene-specific primer complementary to nucleotides 955–929 of ovine Cα, and the products subcloned and sequenced. Five out of five products that extended upstream of the presumptive exon 1/exon 2 junction predicted an amino-terminal amino acid sequence that exactly matched the deduced sequence for $C_s$ by MS/MS.

The nucleotide sequence downstream from the presumptive exon 1/exon 2 junction in the isolated $C_s$ cDNA clones was identical to that for the corresponding region of the ovine Cα clone. This observation confirms that $C_s$ and Cα use alternate 5' exons.

The nucleotide sequence and predicted amino acid sequence of the ovine $C_s$ polypeptide is shown in FIGS. 2A–C. Also shown in FIG. 2A are 29 nucleotides 5' of the translational start site.

Example 10

Detection of Transcripts of both $C_\alpha$ and $C_s$ Isoforms in RNA Isolated From Mammalian Tissues Total RNA isolated from brain, liver, lung, kidney, heart, testis, and skeletal muscle tissue of the mouse was examined for the presence of $C_s$ transcripts. Isolated RNA from these tissues was used as a template for RT-PCR carried out with primers specific for $C_s$. RT-PCR was also performed using primers that would identify Cα associated transcripts. The set of primers specific for $C_s$ used a sense primer corresponding to nucleotides –11 to +16 in the ovine $C_s$ sequence, while the set specific for Cα used a sense primer corresponding to nucleotides 7 to 26 in the ovine and mouse sequences, which are identical in this region. The antisense primer in both cases was complementary to nucleotides 955–929 in the ovine and mouse Cα sequence.

The $C_s$ primer yielded a product only with RNA isolated from testis. In contrast, the Cα-specific primer yielded a prominent product having the predicted size in all tissues examined, including testis. Both $C_s$ and Cα specific transcripts were similarly identified in ovine testis RNA.

These results demonstrate that $C_s$ transcripts are present in mouse testis as well as in ovine testis. To determine if $C_s$ mRNAs are present in the testes of other mammalian species, human testes tissue was tested using PCR and forward primers specific for either $C_s$ (o$C_s$(–11)=ovine $C_s$ nucleotides –11 to +16) or Cα1 (Cαa =consensus Cα1 nucleotides 7–26). In all cases, the reverse primer was CαeR (complement of consensus Cα1 nucleotides 929–955). In human tissue, as was the case in mouse and ovine tissue, the $C_s$-specific primer yielded PCR product of the same size. Therefore, $C_s$ is widespread in mammals. Cα1 transcripts also were found in the testes of all three species, confirming that both C isoforms occur in the testis. Both the Cα1 and $C_s$PCR products had very similar sizes (slightly less than 1 kb), which agrees with the calculated sizes of 949 bases for the Cα1 PCR product, and 942 bases for the $C_s$ PCR product.

In another experiment, RT-PCR was performed on mouse total RNA from brain, heart, kidney, liver, lung, ovary, oocytes, skeletal muscle, testis, and trachea to further investigate the tissue distribution of $C_s$. Two sets of gene-specific primers were used: o$C_s$(–11) and CαeR to detect the presence of $C_s$ mRNA, and Cαa and CαeR to detect Cα1 mRNA. To test for the presence of Cα1 and $C_s$ mRNA in human testis, the PCR was carried out on human testis cDNA (human testis, Marathon-Ready cDNA, Clontech Laboratories, Inc., Palo Alto, Calif.) using the above sets of primers. Thermocycler conditions were: 30 cycles (35 cycles for oocytes and human testis), annealing temperature of 59° C. for 1 minute, extension at 68° C. for 4 minutes, and a final 10-minute extension at 68° C.

As in the previous experiment, Cα1 mRNA was detected in all tissues assayed, whereas $C_s$ mRNA was detected only in testis. It is important to note that $C_s$ mRNA was not detected in ciliated tissues such as brain, lung, or trachea, indicating that $C_s$ is not a component of cilia. Moreover, $C_s$ mRNA was not detected in ovarian tissue or oocytes, indicating that $C_s$ is not expressed in the female germ line. These results strongly suggest that $C_s$ is expressed only in the testis, where the translated protein becomes integrated into the sperm tail.

Example 11

Preparation of a $C_s$-specific Antibody

An antibody specific for $C_s$ was obtained by synthesizing an octapeptide corresponding to ovine $C_s$ residues Ala-1 through Lys-8 using standard techniques (Research Genetics, Inc., Huntsville, Ala.). The octapeptide was acetylated at its amino terminus. The lysyl residue of the peptide was then coupled to keyhole limpet hemocyanin and injected into two rabbits. In Western blots, the sera from the rabbits reacted specifically with $C_s$ and did not cross react with Cα1. The sera also showed little cross-reactivity with any proteins in whole ram sperm other than $C_s$.

The crystal structure of the Cα1 protein predicts that the amino terminal region of the Cα1 is exposed on the surface of the protein. Thus, the epitopes recognized by antibodies to $C_s$ should be accessible in situ as well as in biochemical studies. The $C_s$ antibody is thus useful for biochemical, immunocytochemical, and immuno-electron microscopy studies of $C_s$.

Antibodies can be raised against human $C_s$ using the same procedures described herein.

Example 12

Diagnostic Assays Utilizing $C_s$ Hybridization Probes

A nucleic acid probe containing sequences specific for $C_s$ (e.g., SEQ ID NO:10, SEQ ID NO:11, SEQ ID NO:12, or SEQ ID NO:13) is used to detect $C_s$ mRNA in a sample of germ cells (e.g., a tissue section) suspected of being associated with reduced fertility. The probe is a single-stranded DNA (DNA is preferred because DNA binds to RNA with higher affinity than RNA, and because RNA-DNA hybrids are more stable than RNA-RNA hybrids) that is an antisense strand to the $C_s$ coding sequence. It is produced by standard synthetic methods, and labelled with a radioactive tracer. The probe includes 25 nucleotides that correspond to nucleotides –102 to –78 of human $C_s$.

The assay is carried out by standard methods of in situ hybridization or Northern analysis, using stringent hybridization conditions. Control hybridization assays are run in parallel using normal cells or tissue sections from the same type of tissue as the test sample. For in situ hybridizations, tissues are embedded in paraffin and sectioned using a microtome, or frozen and sectioned in a cryostat, as described by Ausubel et al., supra (Vol. 2, pp 14.1–14.2.8). For Northern analysis, tissues are frozen in liquid nitrogen immediately after biopsy, and total RNA extracted using the guanidinium method as described by Ausubel et al., supra (Vol. 1, pp 4.2.3–4.2.5).

Cells that exhibit a substantially decreased level of hybridization to the probe, compared to the level seen with normal germ cells, are likely to indicate fertility disorders associated with decreased levels of $C_s$ gene expression. These disorders may include, but are not limited to, azoospermia, necrospermia, oligozoospermia, asthenozoospermia, teratozoospermia, oligoasthenospermia, oligoasthenoteratozoospermia, globozoospermia, immotile cilia syndrome, primary ciliary dyskinesia, ideopathic infertility, and others. The amount of hybridization is quantitated by standard methods, such as counting the grains of radioactivity-exposed emulsion on an in situ hybridization assay of a biopsy slide, or by densitometric scan of a Northern blot X-ray film. Alternatively, comparison of the test assay results with the results of the control assays is relative rather than quantitative, particularly where the difference in levels of hybridization is dramatic.

Example 13

Diagnostic Assays Utilizing $C_s$ Antibodies

Antibodies specific for $C_s$ are generated by standard polyclonal or monoclonal methods, using as immunogen a purified, naturally-occurring $C_s$; recombinant $C_s$; or any antigenic fragment of $C_s$, e.g., the acetylated amino terminal fragment, which induces antibodies that react with naturally-occurring $C_s$. The latter fragment can be produced by synthetic or recombinant methods, or by proteolytic digestion of $C_s$. If desired, the antigenic fragment is linked by standard methods to a molecule which increases the immunogenicity of the fragment, such as keyhole limpet hemocyanin (as described above). The polyclonal or monoclonal antibodies so produced are screened using purified recombinant or naturally occurring $C_s$, or as described above, to select those which form an immunocomplex with $C_s$ specifically.

The antibodies so produced are employed in diagnostic methods for detecting cells, tissues, or biological fluids in which the presence of $C_s$ is altered relative to normal cells, as an indication that the patient has a fertility disorder due to altered levels of $C_s$. The sample tested may be a fixed section of a tissue biopsy, a preparation of cells obtained from a suspect germ cell tissue, or a sample of biological fluid, such as semen. Standard methods of immunoassay may be used, including those described above as well as sandwich ELISA. If the tested cells express lower levels of $C_s$ protein in this assay relative to normal cells of the same tissue type, the tested cells are likely to reveal a fertility disorder caused by aberrant levels of $C_s$, such as those described herein.

If a sample is a tissue biopsy, it is first homogenized in buffer supplemented with protease inhibitors, clarified, and then mixed with SDS-PAGE sample buffer. If tissue is a semen specimen, sperm are washed free of seminal plasma and then dissolved in SDS-PAGE sample buffer. The dissolved samples are resolved into their component proteins by SDS-PAGE and are then transferred to a polyvinylidine difluoride (PVDF) membrane for analysis with the $C_s$ antibody.

Example 14

Identification of Human and Mouse $C_s$ Nucleic Acid and Amino Acid Sequences

Primers based on the ovine $C_s$ sequence were used to isolate human and mouse $C_s$ nucleic acids.

To confirm that mouse and human testes have $C_s$, and to determine the degree of similarity between the amino termini of these proteins and that of ovine $C_s$, cDNAs of mouse and human $C_s$ were amplified from testis cDNA by 5'-RACE. In the mouse, adaptor oligonucleotides (Marathon, Clontech Laboratories, Inc., Palo Alto, Calif.) were ligated onto the ends of murine testis cDNAs. $C_s$ cDNA was then specifically amplified by 5'-RACE using the gene-specific primer that is the complement of murine Cα nucleotides 771 to 791, and the adaptor primer AP1 (Marathon, Clonetech). Thermocycler conditions were as follows: 40 cycles, annealing temperature of 56° C. for 1 minute, extension at 68° C. for 4 minutes, with additional 10 minutes extension at 68° C. after the 40th cycle. The product was diluted 1:250 with Tricine-EDTA (10 mM Tricine-KOH, pH 8.5, 0.1 mM EDTA) and reamplified using nested AP1 and the complement of ovine Cα nucleotides 456–482 as primers. Thermocycler conditions for the second round of PCR were annealing at 59° C. for 1 minute, extension at 68° C. for 4 minutes.

The second-round PCR product (clone 7) was ligated into pBluescript II KS(−) at its EcoR V site and subcloned as described above. The cDNAs were verified by restriction enzyme digests and sequencing.

Human $C_s$ cDNA was amplified from Marathon-Ready® human testis cDNA (Clonetech, Palo Alto, Calif.) by 5'-RACE using CαeR and AP1 primers. Thermocycler conditions were as follows: 40 cycles, annealing temperature of 59° C. for 1 minute, extension at 68° C. for 4 minutes, with additional 10 minutes extension at 68° C. after the 40 th cycle. The product of the first round of PCR was diluted 1:250 with Tricine-EDTA (10 mM Tricine-KOH, pH 8.5, 0.1 mM EDTA) and reamplified using nested AP1 and oCα482R as primers and the thermocycler conditions used for murine second round PCR.

The second round PCR product (clone 8) was ligated into the EcoR V site of pBluescript II KS(−) and subcloned as described above. The cDNAs were verified by high stringency hybridization, resistance to digestion by PstI, which digests both the murine and ovine cDNAs, and by sequencing.

FIG. 3 shows the partial nucleotide sequence (SEQ ID NO:42) and predicted partial amino acid sequence (SEQ ID NO:43) of a human $C_s$ cDNA. As was observed in ovine $C_s$, the six amino terminal amino acids differ in sequence from the corresponding Cα1 sequence, after which the predicted amino acids sequence is identical to the human Cα1 sequence.

FIGS. 4A and B are schematic representations of a predicted full length human $C_s$ cDNA (SEQ ID NO:35) and its predicted full length amino acid sequence (SEQ ID NO:34). Sequences specific to $C_s$ are shown in upper case, while sequences common to Cα1 are shown in lower case.

FIG. 5 is a schematic representation of a partial nucleotide sequence (SEQ ID NO:44) and predicted partial amino acid sequence (SEQ ID NO:45) of a mouse $C_s$ cDNA. The mouse cDNA similarly encodes a $C_s$ polypeptide that differs in its first seven amino acids from mouse Cα1, after which the sequence is identical to the mouse Cα1 sequence.

FIGS. 6A to D are a schematic representation of a predicted full length mouse $C_s$ cDNA (SEQ ID NO:39) and its predicted amino acid sequence (SEQ ID NO:38). Sequences specific to $C_s$ are highlighted, while sequences common to Cα1 and $C_s$ are not.

FIGS. 7A and B are schematic comparisons of murine, ovine, and human $C_s$ exon 1s. As shown, exon 1 of murine $C_s$ and exon 1 of human $C_s$ are very similar to the ovine $C_s$ exon 1 (FIG. 7A). The coding region of exon 1s of each of the three cDNAs differs from the others at only 2 out of 22 positions. Each of these substitutions results in the incorporation of a different amino acid residue into the $C_s$ polypeptide (FIG. 7B). The first three amino acid residues are predicted to be identical for all three species, but the next three residues are S or N at positions 4 and 6 and P or S at position 5.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid molecule comprising a nucleotide sequence that encodes a polypeptide, the amino acid sequence of which is identical to SEQ ID NO:34.

2. An isolated nucleic acid molecule comprising SEQ ID NO:35.

3. A vector comprising the nucleic acid molecule of claim 1.

4. The vector of claim 3, wherein the vector is an expression vector.

5. A host cell which contains the nucleic acid molecule of claim 1.

6. The host cell of claim 5, wherein the cell is a non-human mammalian cell.

7. A method for producing a polypeptide, the method comprising culturing the host cell of claim 5 under conditions in which the nucleic acid molecule is expressed.

8. A vector comprising the nucleic acid molecule of claim 2.

9. The vector of claim 8, wherein the vector is an expression vector.

10. A host cell which contains the nucleic acid molecule of claim 2.

11. The host cell of claim 10, wherein the cell is a non-human mammalian cell.

12. A method for producing a polypeptide, the method comprising culturing the host cell of claim 10 under conditions in which the nucleic acid molecule is expressed.

* * * * *